United States Patent [19]

Campbell et al.

[11] Patent Number: 5,686,073
[45] Date of Patent: Nov. 11, 1997

[54] POLYCLONAL AND MONOCLONAL ANTIBODIES AGAINST A 43 KDA DYSTROPHIN ASSOCIATED PROTEIN

[75] Inventors: Kevin P. Campbell, Iowa City, Iowa; Oxana B. Ibraghimov, Southboro, Mass.; James M. Ervasti, Middleton, Wis.; Cynthia J. Leveille, Iowa City, Iowa

[73] Assignee: The University of Iowa Research Foundation, Iowa City, Iowa

[21] Appl. No.: 483,278

[22] Filed: Jun. 7, 1995

Related U.S. Application Data

[63] Continuation-in-part of Ser. No. 123,161, Sep. 16, 1993, Pat. No. 5,449,616, which is a continuation-in-part of Ser. No. 946,234, Sep. 14, 1992, Pat. No. 5,308,752, which is a continuation-in-part of Ser. No. 841,654, Feb. 20, 1992, Pat. No. 5,260,209, which is a continuation-in-part of PCT/US91/03632, May 23, 1991, which is a continuation-in-part of Ser. No. 527,583, May 23, 1990, Pat. No. 5,187,063.

[51] Int. Cl.$^6$ ............... C07K 7/08; C07K 16/28; C12P 21/08
[52] U.S. Cl. ............... 424/185.1; 435/70.21; 435/172.2; 530/326; 530/388.85; 530/389.1
[58] Field of Search ............... 435/240.1, 240.27, 435/70.21, 172.2; 530/387.9, 388.1, 389.1, 326, 388.9, 389.8, 300, 350, 388.85; 424/185.1; 514/2, 8

[56] References Cited

U.S. PATENT DOCUMENTS

| | | | |
|---|---|---|---|
| 4,912,202 | 3/1990 | Campbell et al. | |
| 5,187,063 | 2/1993 | Campbell et al. | 435/7.21 |
| 5,260,209 | 11/1993 | Campbell et al. | 435/240.2 |
| 5,308,752 | 5/1994 | Campbell et al. | 435/7.21 |
| 5,449,616 | 9/1995 | Campbell et al. | 435/240.2 |

FOREIGN PATENT DOCUMENTS

| | | |
|---|---|---|
| 0 331 514 A2 | 9/1989 | European Pat. Off. |
| WO 89/06286 | 7/1989 | WIPO |
| WO 91/18107 | 11/1991 | WIPO |

OTHER PUBLICATIONS

Hoffman, et al., *Cell 51:* 919–928 (1987).
Knudson, et al., *J. Biol. Chem.* 263(17): 8480–8484 (1988).
Hoffman, et al., *N.E. J. Med.* 318(21): 1363–1368 (1988).
Campbell, et al., *Am. J. Human Gen.* 49 (4 Suppl.): 4 (1991).
Ervasti, et al., *Cell 66:* 1121–1131 (1991).
Ibraghimov–Beskrovnaya, et al., *Nature 355:* 696–702 (1992).
Zubrzycka–Gaarn, et al., *Nature 333:* 466–469 (1988).
Arahata, et al., *Nature 333:* 861–863 (1988).
Bonilla, et al., *Cell 54:* 447–452 (1988).
Cooper, et al., *Nature 334:* 154–156 (1988).
Campbell and Kahl, *Nature 338:* 259–262 (1989).
Ervasti, et al., *Nature 345:* 315–319 (1990).
Jorgensen, et al., *J. Cell Biol.* 110: 1173–1185 (1990).
Sevier, et al., *Clin. Chem.* 271: 1797–1806 (1981).

*Primary Examiner*—Christina Y. Chan
*Assistant Examiner*—F. Pierre Vander Vegt
*Attorney, Agent, or Firm*—Kevin M. Farrell

[57] ABSTRACT

Disclosed are methods for the preparation of polyclonal and monoclonal antibodies which bind specifically to a 43 kDa dystrophin-associated. The molecular weight of the 43 kDa protein is determined by electrophoretic separation under denaturing conditions, followed by transfer to a solid support and staining with wheat germ agglutinin. The method includes a step in which the peptide PKNMTPYRSPPPYVP (SEQ ID NO: 15) is administered to stimulate an immune response. Also disclosed are polyclonal and monoclonal antibodies which bind specifically to the 43 kDa dystrophin-associated protein.

6 Claims, 1 Drawing Sheet

POLYCLONAL AND MONOCLONAL ANTIBODIES AGAINST A 43 KDA DYSTROPHIN ASSOCIATED PROTEIN

RELATED APPLICATIONS

This application is a continuation-in-part of U.S. Ser. No. 08/123,161, (now U.S. Pat. No. 5,449,616), filed Sep. 16, 1993, which is a continuation-in-part of U.S. Ser. No. 07/946,234, filed Sep. 14, 1992 (now U.S. Pat. No. 5,308,752), which is a continuation-in-part of U.S. Ser. No. 07/841,654, filed Feb. 20, 1992 (now U.S. Pat. No. 5,260,209), which is a continuation-in-part of international application number PCT/US91/03632, filed May 23, 1991, which is a continuation-in-part of U.S. Ser. No. 07/527,583, filed May 23, 1990 (now U.S. Pat. No. 5,187,063).

BACKGROUND OF THE INVENTION

It has been demonstrated that Duchenne's muscular dystrophy is caused by a mutation or deletion which results in the absence of the dystrophin protein. In addition, the nucleic acid sequence encoding the dystrophin protein has been isolated and the nucleotide sequence has been determined. These discoveries have enabled new diagnostic and therapeutic approaches to Duchenne's muscular dystrophy based on recombinant DNA technology.

Dystrophin has been shown to be associated with a large oligomeric complex of sarcolemmal glycoproteins (see, e.g., Ervasti and Campbell, Cell 66:1121-1131 (1991)). Substantial reduction in selected components of the dystrophin-glycoprotein complex have also been found to correlate with disease phenotypes. The isolation and characterization of DNA encoding the various non-dystrophin components of the dystrophin-glycoprotein complex would enable diagnostic and therapeutic approaches similar to those discussed above in connection with the DNA encoding dystrophin.

SUMMARY OF THE INVENTION

The subject invention relates to purified nucleic acid corresponding to protein components of the dystrophin-glycoprotein complex. More specifically, disclosed herein are nucleic acid sequences encoding dystroglycan (which is post-translationally cleaved to generate the 43 kDa and 156 kDa components of the dystrophin-glycoprotein complex), the 50 kDa component of the complex and the 59 kDa component of the complex.

One aspect of the invention relates to substantially pure nucleic acid molecules (preferably having a length of at least about 10 nucleotides) which hybridize to the disclosed sequences, or the complement thereof, under stringent hybridization conditions. Such nucleic acids are useful, for example, as nucleic acid probes or primers for nucleic acid polymerization.

Another aspect of the invention relates to substantially pure nucleic acid molecules encoding at least a portion of a dystrophin-associated glycoprotein which is selected from the group consisting of dystroglycan, the 50 kDa dystrophin-associated protein and the 59 kDa dystrophin-associated protein. Related to this are DNA expression constructs which include the nucleic acid, and cells transformed with such constructs.

DETAILED DESCRIPTION OF THE INVENTION

Figure 1:
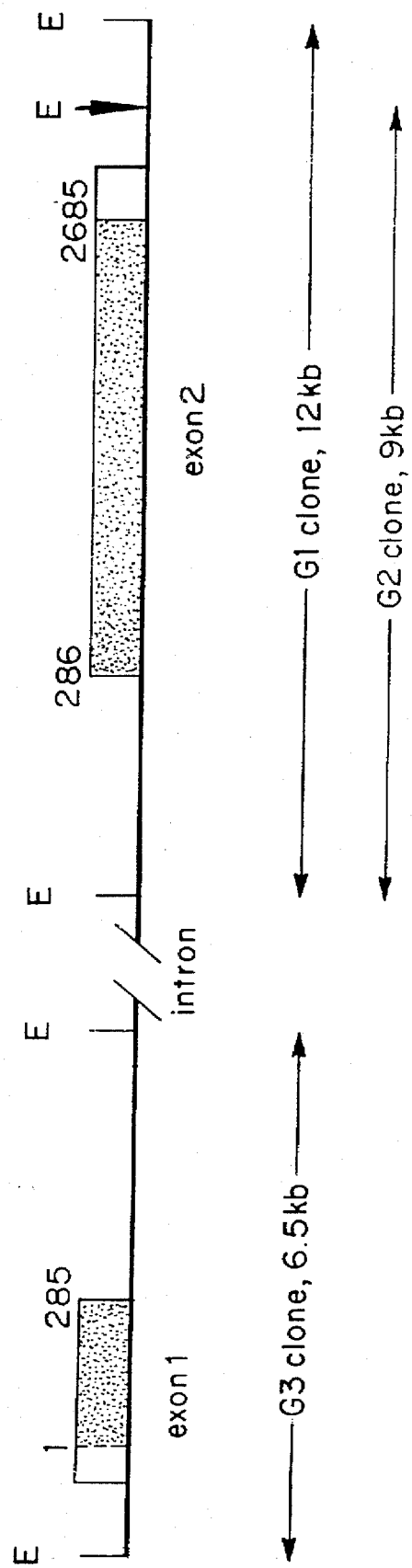
FIG. 1 is a diagram of the genomic structure of human dystroglycan. The schematic structure of the dystroglycan gene is not drawn to scale. The gene is represented by the line, interrupted at the location of the intron. Coding sequences within exons are shown by the shaded boxes. A polymorphic EcoRI site, which is present within clone G2 but not G1 is indicated by the arrowhead.

Dystrophin is a large molecular weight protein product of the defective gene responsible for Duchenne's Muscular Dystrophy. This invention is based, in part, on the discovery that dystrophin exists as a component of a large oligomeric complex in the sarcolemmal membrane of normal skeletal muscle. Proteins and glycoproteins comprise the other components of this complex which is referred to herein as the dystrophin-glycoprotein complex. Specifically, the other components comprise a 156 kDa glycoprotein, a 50 kDa glycoprotein, a 43 kDa glycoprotein, a 35 kDa glycoprotein, a 25 kDa protein and a triplet of proteins of 59 kDa molecular weight. These components are referred to as the non-dystrophin components of the dystrophin-glycoprotein complex.

Isolation of the Dystrophin-Glycoprotein Complex

The dystrophin-glycoprotein complex can be isolated from detergent solubilized skeletal muscle membranes using affinity chromatography and density gradient ultracentrifugation. Lectins are proteins or glycoproteins which bind certain sugars or oligosaccharides. This property can be used to isolate certain glycoproteins from a complex mixture and is extremely useful as a general approach to the purification of membrane proteins, many of which are glycosylated. In the present invention, the linked components of the dystrophin-glycoprotein complex can be isolated as an intact complex with lectins that bind to the glycoprotein components of the complex. The lectins are typically coupled to a solid support such as a chromatographic gel (i.e., sepharose, agarose, etc.) and a complex mixture of membrane components is passed through a chromatography column containing the gel with bound lectin. The glycoproteins of membrane components bind to the lectin while the other components of the mixture pass through the column. As described in greater detail below, a variety of lectins can be used in affinity-based methodologies to isolate the dystrophin-glycoprotein complex.

The dystrophin-glycoprotein complex can be further purified using density gradient ultracentrifugation. The eluate from the affinity column as described above is applied as a narrow band to the top of a solution in a centrifuge tube. To stabilize the sedimenting components of the eluate against convection mixing, the solution beneath the band contains an increasingly dense solution of an inert, highly soluble material such as sucrose (a density gradient). Under these conditions, the different fractions of the eluate sediment at different rates forming distinct bands that can be individually collected. The rate at which each component sediments depends on its size and shape and is normally expressed as its sedimentation coefficient or S value.

Present day ultracentrifuges rotate at speeds up to about 80,000 rpm and produce forces up to about 500,000×gravity. At these enormous forces, even relatively small macromolecules, such as tRNA molecules and simple enzymes, separate from one another on the basis of their size. Using this technique, the size of the dystrophin-glycoprotein complex was estimated to be approximately 18S by comparing its migration to that of standards of varying size.

Another form of affinity chromatography which can be used to isolate the dystrophin-glycoprotein complex is known as immunoaffinity purification. This technique utilizes the unique high specificity of polyclonal and monoclonal antibodies as well as selected lectins. Such highly specific molecules are extremely valuable tools for rapid, selective purification of antigens. In principle, the antigen is coupled (immobilized) on a column support and this is used to selectively adsorb antigen from a mixture containing many other antigens. The antigens for which the antibody has no affinity can be washed away, and the purified antigen then eluted from the bound antibody or lectin with an elution buffer. Examples of antibodies and lectin molecules which are useful for the immunopurification of the dystrophin complex components are described in detail below.

The separation and isolation of the components of the dystrophin-glycoprotein complex can be accomplished by SDS-polyacrylamide gel electrophoresis (SDS-PAGE). In this technique, proteins are reacted with the detergent sodium dodecylsulfate (SDS), to form negatively charged complexes. The amount of SDS bound by a protein, and consequently the charge on the complex, is roughly proportional to its size. Commonly, about 1.4 grams SDS is bound per 1 gram protein, although there are exceptions to this rule. The proteins are generally denatured and solubilized by their binding of SDS, and the complex forms a prolate ellipsoid or rod of a length roughly proportionate to the molecular weight of the protein. Thus, proteins of either acidic or basic isoelectric point form negatively charged complexes that can be separated on the basis of differences in charges and sizes by electrophoresis through a sieve-like matrix of polyacrylamide gel.

An alternative method for isolating the components of the dystrophin-glycoprotein complex is gel filtration high pressure liquid chromatography. This technique, in addition to taking less time than SDS gel electrophoresis, allows easier quantitation and recovery of separated proteins, and the resolution is better than that achieved by gel filtration with conventional materials.

Preparation of Antibodies Reactive with Components of the Dystrophin-Glycoprotein Complex Monoclonal and polyclonal antibodies specific for non-dystrophin components of the dystrophin-glycoprotein complex are particularly useful in the isolation and diagnostic methods of this invention. Monoclonal antibodies useful in this invention are obtained by well known hybridoma methods. An animal is immunized with a preparation containing the dystrophin-glycoprotein complex. A fused cell hybrid is then formed between antibody-producing cells from the immunized animal and an immortalizing cell such as a myeloma.

In preferred embodiments, anti-non-dystrophin component monoclonal antibodies of this invention are produced by murine hybridomas formed by fusion of: a) mouse myeloma or hybridoma which does not secrete antibody with b) murine spleen cells which secrete antibodies obtained from mice immunized against dystrophin-glycoprotein complex.

Typically, the mice are immunized with a primary injection of dystrophin-glycoprotein complex followed by a number of boosting injections of dystrophin-glycoprotein complex. During or after the immunization procedure, sera of the mice may be screened to identify those mice in which a substantial immune response to the complex has been evoked. From selected mice, the spleen cells are obtained and fusions are performed. Suitable fusion techniques are the Sendai virus technique (Kohler, G. and Milstein, C., *Nature*, 256:495 (1975)), or the polyethylene glycol method (Kennet, R. H., "Monoclonal Antibodies, Hybridomas—A New Dimension in Biological Analysis," Eds. R. H. Kennet, T. J. McKern and K. B. Bechtol, Plenum Press, NY (1980)).

The hybridomas are then screened for production of anti-non-dystrophin component antibodies. A suitable screening technique is a solid phase radioimmunoassay. A solid phase immunoadsorbent is prepared by coupling dystrophin-glycoprotein complex or non-dystrophin components to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with dystrophin-glycoprotein complexes or non-dystrophin components. The hybridoma products are then examined for their ability to react with natural and synthetic components of the dystrophin-glycoprotein complex.

The monoclonal anti-non-dystrophin component antibodies can be produced in large quantities by injecting anti-non-dystrophin component antibody producing hybridoma cells into the peritoneal cavity of mice and, after an appropriate time, harvesting acites fluid from the mice which yield a high titer of homogenous antibody. The monoclonal antibodies are isolated therefrom. Alternatively, the antibodies can be produced by culturing anti-non-dystrophin component antibody producing cells in vitro and isolating secreted monoclonal anti-non-dystrophin component antibodies from the cell culture medium directly.

Another method of forming antibody-producing cells is by viral or oncogenic transformation. For example, a B-lymphocyte which produced a non-dystrophin component specific antibody may be infected and transformed with a virus, such as the Epstein-Barr virus, to give an immortal antibody-producing cell (Kozbon and Roder, *Immunol. Today* 4:72–79 (1983)). Alternatively, the B-lymphocyte may be transformed by a transforming gene or gene product.

Polyclonal antibodies can be prepared by immunizing an animal with a crude preparation of the dystrophin-glycoprotein complex or the purified non-dystrophin components of the complex. The animal is maintained under conditions whereby antibodies reactive with the components of the complex are produced. Blood is collected from the animal upon reaching a desired titer of antibodies. The serum containing the polyclonal antibodies (antisera) is separated from the other blood components. The polyclonal antibody-containing serum Can optionally be further separated into fractions of particular types of antibodies (e.g., IgG or IgM) or monospecific antibodies can be affinity purified from polyclonal antibody containing serum.

Diagnostic Methods

An observation which is fundamental to the subject invention is that there is a strong correlation between the absence or reduction in the quantity of the non-dystrophin components of the dystrophin-glycoprotein complex and affliction by muscular dystrophy. As described in the Exemplification below, monoclonal or polyclonal antibodies can be used to detect the absence or reduction of a particular non-dystrophin component of the complex. In both mouse and human samples of dystrophic tissue, muscular dystrophy can be diagnosed by detecting reduction or absence of non-dystrophin components of the complex.

This analysis can be extended beyond the Duchenne-type muscular dystrophy (X-linked) to the detection of autosomal-based muscular dystrophy. One example of such an autosomal-based muscular dystrophy is severe childhood autosomal recessive muscular dystrophy (SCARMD). SCARMD is a disease which is prevalent in North Africa, and has also been identified in South American and European patients. This progressive muscular dystrophy shares several clinical features with Duchenne's muscular dystrophy (DMD) including, for example, mode of onset, rapid progression, hypertrophy of calves and extremely high serum creatine kinase levels during the initial stages of the disease (see, e.g., Ben Hamida et al., *J. Neurol Sci.* 107:60–64 (1992)). Fukuyama congenital muscular dystrophy is another example of such an autosomal based muscular dystrophy.

In one embodiment of the diagnostic method of the invention, a muscle biopsy sample is treated in a procedure which renders the non-dystrophin components available for complexing with antibodies directed against said components. Muscle samples are obtained from patients by surgical biopsy. The site of biopsy could be any skeletal muscle suspected of being dystrophic. Muscle groups about the shoulder and pelvic girdles, however, are the most affected, and are likely to be the most common site of biopsy. The amount of muscle obtained should be enough to extract the components of the dystrophin-glycoprotein complex from muscle membranes and detect their presence by the diagnostic methods described within this application. Alternative methods of extraction can be used.

For biopsy samples greater than 500 mg, the muscle tissue can be homogenized by mechanical disruption using apparatus such as a hand operated or motor driven glass homogenizer, a Waring blade blender homogenizer, or an ultrasonic probe. Homogenization can occur in a buffer comprising 20 mM sodium pyrophosphate, 20 mM sodium phosphate monohydrate, 1 mM magnesium chloride, 0.303 M sucrose, 0.5 mM EDTA, pH 7.1, with various protease inhibitors such as aprotinin (0.5 µg/ml), benzamidine (100 µg/ml), iodoacetamide (185 µg/ml), leupeptin (0.5 µg/ml), pepstatin A (0.5 µg/ml) and PMSF (40 µg/ml). Heavy microsomes can be prepared from homogenized skeletal muscle by the method of Mitchel, et al. (*J. Cell. Biol.*, 95: 1008–1016 (1983)). The microsomes are then washed with a physiological salt solution and solubilized in saline containing detergent and protease inhibitors. Following solubilization of the microsomes, the sample is treated with SDS. In the present case, SDS acts to dissociate the linked components of the dystrophin-glycoprotein complex, thereby allowing their separation.

For muscle biopsy samples less than 500 mg, an alternative extraction procedure can be used. Samples are frozen in liquid nitrogen and crushed using a mortar and pestle and prepared for electrophoresis by treatment with SDS as described by Hoffman et al. (*N. Eng. J. Med.* 318: 1363–1368 (1988)), hereby incorporated by reference.

The components of the SDS treated sample are then separated electrophoretically. Following electrophoretic separation, the components of the dystrophin-glycoprotein complex are transferred from the gel matrix to a solid support. The components are transferred out of the gel and onto a filter or membrane, forming an exact replica of the original protein separation, but leaving the transferred proteins accessible for further study. The detection of transferred proteins can be accomplished by the use of general protein dyes such as Amido black or Coomassie brilliant blue. Alternatively, antibodies which are specific for the known non-dystrophin components of the dystrophin-glycoprotein complex can be labeled with a detectable reporter group and used to bind to the various components. An example of this method is the well known Western blot method. In yet another alternative detection method, unlabeled antibodies specific for a component of the dystrophin-glycoprotein complex are incubated with a muscle tissue sample under conditions appropriate for binding. The specific binding of these antibodies to the muscle tissue sample is detected through the use of labeled secondary antibodies by conventional techniques.

Alternatively, tissue specimens (e.g., human biopsy samples) can be tested for the presence of the components of the dystrophin-glycoprotein complex by using monoclonal or polyclonal antibodies in an immunohistochemical technique, such as the immunoperoxidase staining procedure. In addition, immunofluorescent techniques can be used to examine human tissue specimens. In a typical protocol, slides containing cryostat sections of frozen, unfixed tissue biopsy samples are air-dried and then incubated with the anti-non-dystrophin component antibody preparation in a humidified chamber at room temperature. The slides are layered with a preparation of fluorescently labeled antibody directed against the monoclonal antibody. As mentioned above, labeled secondary antibodies are also useful for detection. The staining pattern and intensities within the sample are determined by fluorescent light microscopy.

The antibodies of the present invention can also be used in an enzyme-linked immunoadsorbant assay (ELISA) for determining the absence or presence of non-dystrophin components of the dystrophin-glycoprotein complex. Antibodies against non-dystrophin components to be measured are adsorbed to a solid support, in most cases a polystyrene microtiter plate. After coating the support with antibody and washing, a solubilized sample is added. If a non-dystrophin component is present for which the antibodies are specific, they will bind to the adsorbed antibodies. Next, a conjugate that will also bind to the non-dystrophin component is added. Conjugates are secondary antibody molecules to which an enzyme is covalently bound. After addition of a chromogenic substrate for the enzyme, the intensity of the colored reaction products generated will be proportional to the amount of conjugated enzyme and thus indirectly to the amount of bound non-dystrophin component. Since the intensity of the developed color is proportional to the amount of non-dystrophin component present, determination of the intensity of the color produced by a standard series of non-dystrophin component concentrations will allow the calculation of the amount of non-dystrophin component in an unknown sample. Many variations of this assay exist as described in Voller, A., Bidwell, D. E. and Bartlett, A., The Enzyme Linked Immunoadsorbent Assay (ELISA): A guide with abstracts of microplate applications, Dynatech Laboratories, Alexandria, Va. (1979) and are hereby incorporated by reference.

In another embodiment of the diagnostic method, antibodies specifically reactive with an extracellular component of the dystrophin-glycoprotein complex (e.g., the 156 kDa component) are labeled with a detectable reporter group and administered (e.g., intravenously) to an individual to be tested for muscular dystrophy using conventional immunodiagnostic methods. The extracellular components of the dystrophin-glycoprotein complex are exposed on the surface of an intact cell and therefore, are reactive with labeled circulating antibodies which have the ability to pass through capillary membranes to reach the muscle tissue surface. Thus, the disruption of the cell is not necessary for diagnosis.

Isolation of Nucleic Acids Encoding Dystrophin-Associated Proteins and Uses for Same Antibodies reactive with dystrophin-associated proteins can be used to isolate and purify nucleic acid which encodes the proteins. This can be accomplished in a variety of ways. For example, monospecific polyclonal antibodies, or monoclonal antibodies, can be used in affinity purification methods to isolate highly purified preparations of individual dystrophin-associated glycoproteins (DAGs). Using standard biochemical techniques (e.g., Edman degradation), the amino acid sequence of a portion of the protein can be determined. Using this protein sequence information, degenerative nucleic acid probes can be designed and synthesized. Such probes can be used to screen nucleic acid libraries (e.g., cDNA libraries from tissues known to express the dystrophin-associated proteins). DNA sequences identified by such a screening method can be used to isolate overlapping clones. This process leads ultimately to the reconstruction of the entire coding region.

Alternatively, monoclonal or polyclonal antibodies can be used to screen an expression library, such as a cDNA library prepared in the vector λgt11. The λgt11 system enables the expression of DNA fragments from a DNA library of interest (e.g., a human genomic DNA library) as a beta-galactosidase fusion protein. Recombinant phage are plated on a lawn of bacteria and the recombinants are screened immunologically using conventional techniques.

Once isolated, the DNA encoding components of the dystrophin-associated proteins can be used in a variety of ways. For example, all, or a portion of the DNA can be inserted in an expression vector which can be used to express the full-length protein, or a portion thereof. The full-length protein, or portion thereof, can also be expressed as a portion of a larger fusion protein containing amino acid residues encoded by an unrelated gene. Such vectors contain all necessary regulatory signals to promote the expression of a DNA segment of interest. Expression vectors are typically either prokaryote specific, or eukaryote specific. However, vectors have been developed which can promote the expression of a DNA sequence of interest in either a prokaryotic or eukaryotic system. Such vectors are known as shuttle vectors.

Prokaryotic expression vectors are useful for the preparation of large quantities (up to milligram quantities) of the protein encoded by a DNA sequence of interest. This protein, or immunogenic peptide portions of same, can be used for example, as a source of highly pure immunogen for the generation of antibodies specific to components of the complex. Immunogenic peptides can also by produced synthetically from the known DNA sequence. Alternatively, as discussed in detail below, some proteins may be useful for therapeutic applications.

As has been discussed previously, several of the dystrophin-associated proteins are extensively glycosylated. Because prokaryotic systems do not possess the cellular machinery necessary to reproduce this glycosylation, it may be desirable to produce the proteins in a eukaryotic system using a eukaryotic expression system.

While Duchenne and Becker muscular dystrophy are characterized by the absence, or reduction in the abundance of, dystrophin (as well as the dystrophin-associated proteins) in afflicted individuals, this is not true with all forms of muscular dystrophy. It has been observed, for example, that in patients suffering from Fukuyama congenital muscular dystrophy (FCMD), all of the dystrophin-associated glycoproteins are substantially diminished whereas the abundance of dystrophin is only mildly reduced when compared to control samples.

In studies of muscle tissue from patients afflicted with severe childhood autosomal recessive muscular dystrophy (SCARMD), it was determined that the 50 kDa dystrophin-associated protein was substantially reduced whereas levels of dystrophin and other dystrophin-associated proteins were not substantially reduced. More specifically, dystrophin and the 156 kDa, 59 kDa and 43 kDa dystrophin-associated proteins were determined to be present at normal or near normal levels. The 35 kDa dystrophin-associated protein was determined to be present at a somewhat reduced level, although not reduced to the degree observed in DMD tissue.

In addition to the two examples discussed above, it is highly likely that other autosomal mutation-based muscular dystrophies result from deleterious mutations or deletions in the genes encoding one or more of the dystrophin-associated proteins. Thus, another use for a DNA expression vector encoding a dystrophin-associated protein is to complement such a mutation. For example, an expression vector containing the DNA sequence encoding the human 50 kDa dystrophin-associated glycoprotein can be introduced into the muscle tissue of an individual afflicted with SCARMD.

The DNA expression vector can be introduced into the individual in a variety of ways. For example, myoblast cells can be isolated from the afflicted individual by biopsy, transformed with the expression construct in vitro and reintroduced to the afflicted individual by intramuscular injection. Alternatively, the DNA expression construct can be administered directly to the afflicted individual, for example, by intramuscular injection.

A variety of techniques can be employed to ensure that the DNA encoding the dystrophin-associated protein is taken up by cells following intramuscular injection. For example, the expression vector employed can be a defective animal virus having the ability to infect human cells (e.g., adenovirus or retrovirus derivatives). In addition, liposome technology has been developed in which the expression construct is encapsulated in a membrane having the ability to fuse with mammalian cell membranes thereby allowing the transfer of the liposome contents into the mammalian cell. Liposomes can be targeted to muscle cells specifically through the use of specific membrane markers.

In addition to the use of expression vectors to mediate gene therapy, the administration dystrophin-associated protein, or portions thereof, to an afflicted individual may also offer a viable therapeutic alternative. Because of the difficulties associated with introducing a protein into a cell across the cell membrane, this therapeutic approach is would be most useful for muscular dystrophies characterized by the absence or reduction in abundance of an extracellular protein. The 156 kDa dystrophin-associated protein is such a protein.

In addition, the 156 kDa dystrophin-associated protein is characterized by other properties which suggest that this type of therapy would be effective. For example, as reported in the Exemplification section which follows, the 156 kDa protein binds laminin which is one of the major components of the extracellular matrix. In fact, it appears to be a high affinity laminin binding protein. Although the mechanism underlying the fact that dystrophin deficiency causes the muscle cell necrosis characteristic of muscular dystrophy is unknown, experiments suggest that dystrophin functions to link the subsarcolemmal membrane cytoskeleton through a transmembrane complex to an extracellular glycoprotein which binds laminin. Although the exact function of the 156 kDa protein is not known, muscle cells do interact with the extracellular matrix via specific cell surface receptors and thus it is likely that the 156 kDa protein is involved in the interactions between sarcolemma and extracellular matrix.

In a therapeutic method, the 156 kDa protein, or a laminin binding domain thereof, would be administered (preferably intravenously) to an afflicted individual. At the surface of the muscles tissue, the 156 kDa protein, or the laminin binding portion thereof, is expected to interact with the sarcolemma and extracellular matrix thereby stabilizing the tissue. The progress of therapy can be monitored, for example, by a combination of muscle strength measurement and muscle biopsy analysis.

In addition to the use of the nucleic acid sequence encoding a dystrophin-associated protein in an expression construct, the DNA sequence of the dystrophin-associated proteins disclosed herein is also useful in the design of molecular probes for detection of substantially complementary nucleic acid sequences, or primers for polymerization from nucleic acid templates which are substantially complementary. Substantially complementary, as used in this context, includes sequences which hybridize to the probe or primer under stringent hybridization conditions; such conditions have been described elsewhere in this application.

In such applications, a portion of the nucleotide sequence encoding the dystrophin-associated protein is selected, on the basis of its specific sequence, to selectively hybridize to the DNA encoding the dystrophin-associated protein. Probes selected in this manner are useful in a variety of conventional detection/diagnostic techniques. For example, probes can be labeled with a detectable reporter group and used to detect complementary sequences in hybridization assays such as Southern or Northern analysis.

Primers selected in this manner are useful, for example, as a substrate for the initiation of nucleic acid polymerization reactions (e.g., in DNA sequencing reactions by the dideoxy chain termination technique). In addition, pairs of such primers are useful in the well known polymerase chain reaction (PCR) technique for nucleic acid amplification. In this method, the primers are selected to be complementary to anti-parallel strands of a double stranded DNA molecule. The PCR product produced by such an amplification reaction will have a characteristic size which is dependent upon the distance (as expressed in base pairs) between the hybridization positions of the two primers to anti-parallel strands of a nucleic acid molecule. PCR primers designed using the sequence information disclosed herein are useful in a wide array of diagnostic contexts which will be apparent to one skilled in the art.

Such diagnostic applications are particularly important in this context since, as discussed above, many of the autosomal mutation-based muscular dystrophies are likely to result from mutations in the DNA encoding a dystrophin-associated protein. Thus, one method for diagnosing autosomal muscular dystrophy involves identifying mutations in the DNA sequence encoding a dystrophin-associated protein which correlates with the disease phenotype. This can be done, for example, using immunohistochemical techniques as described in the Examples which follow. DNA encoding a dystrophin-associated protein can be isolated from an individual whose affliction has been demonstrated in such a manner. The DNA sequence of the gene from an afflicted individual can be compared with the DNA sequence of the gene from a non-afflicted individual. Using this technique, particular mutations are identified which correlate with the disease phenotype. Using this information, synthetic oligonucleotide probes can be synthesized which facilitate the rapid detection of such mutations in a DNA sample from an individual to be tested for autosomal muscular dystrophy.

For example, if the mutation which correlates with the disease phenotype is found to be a point mutation in the gene encoding the 156 kDa dystrophin-associated protein, a synthetic peptide of about 10–15 base pairs in length can be synthesized. The sequence of the synthetic peptide should have a sequence which is perfectly complementary to the appropriate region of either the normal gene or the mutant gene. Using conventional hybridization techniques it is possible to rapidly identify the presence of either the normal sequence or the mutant sequence in a sample of DNA from an individual to be tested.

The invention is now further and specifically illustrated by the following examples.

EXEMPLIFICATION

Example 1

Isolation and Characterization of Dystrophin-Glycoprotein Complex

Isolation of complex by density centrifugation

Heavy microsomes were prepared from rabbit skeletal muscle by the method described in Mitchell, et al. (*J. Cell. Biol.* 95:1008–1016 (1983)). The microsomes were washed twice with 0.6 M KCl in 50 mM tris-HCl, pH 7.4, 0.165 M sucrose, 0.1 mM PMSF and 0.75 mM benzamidine to remove contractile proteins. One gram of KCl-washed membranes were solubilized in 1.0% digitonin, 0.5 M NaCl, and protease inhibitors as previously described in Campbell, K. P. and Kahl, S. D., *Nature*, 338:259–262 (1989). After removal of the ryanodine receptor by immunoaffinity chromatography as described in Imagawa et al. (*J. of Biol. Chem.*, 262:16636–16643 (1987)), the digitonin-solubilized membranes were circulated overnight in a 40 ml WGA-sepharose column, washed extensively, then eluted with three column volumes of 0.3 M N-acetyl-glucosamine.

Eluted fractions containing dystrophin were applied to a 3 ml DEAE cellulose column and sequentially eluted with the following NaCl concentrations in buffer A (0.1% digitonin, 50 mM tris-HCl, pH 7.4, 0.75 mM benzemidine, 0.1 mM PMSF): 0 mM, 25 mM, 50 mM, 75 mM, 100 mM, 110 mM and 175 mM. Sucrose gradients (12.5 ml linear 5% to 20% sucrose) containing 0.5 M NaCl and 0.01% NaN$_3$ in buffer A were prepared using a Beckman density gradient former. Dystrophin-glycoprotein complex, which eluted in fraction two (3 ml) from the DEAE-column 175 mM NaCl wash was concentrated to 0.5 ml in a centricon-100 (Amicon), layered on a sucrose gradient, and overlaid with 0.5 ml of buffer A containing 175 mM NaCl and 0.01% NAN$_3$. Gradients were centrifuged at 4° C. in a Beckman VTi 65.1 vertical rotor for 90 minutes at 200,000XG. Fractions (0.6 ml) were collected from the top of the gradients using an ISCO Model 640 density gradient fractionator.

Affinity characterization of dystrophin-glycoprotein complex

Gradient fractions were separated by SDS-PAGE (3% to 12% gradient gel) and stained with Coomassie Blue (300 µl of fractions concentrated to 50 µl with a centricon-100) or transferred to nitrocellulose and stained with various antibodies. Gel lanes were scanned with a Hoefer GS300 scanning densitometer and analyzed using GS-360 data analysis software.

Polyclonal antisera against a chemically synthesized decapeptide representing the C-terminal of dystrophin was raised in New Zealand white rabbits as previously described in Strynadka, N. C. J., et al., *J. of Virol.*, 62: 3474–3483 (1988). Hybridomas were obtained from female balb/C mice which were immunized with rabbit skeletal muscle membranes and boosted with WGA eluate as described in Jorgensen, A. O., et al., *Cell Motility and Cytoskeleton*, 9: 164–174 (1988).

It was evident from the Coomassie Blue-stained gel of sequential gradient fractions that the dystrophin-glycoprotein complex was clearly separated from the voltage-sensitive sodium channel and the dihydropryidine receptor. The size of the dystrophin-glycoprotein complex was estimated to be approximately 18 S by comparing its migration to that of the standards B-galactosidase (15.9 S), thyroglobulin (19.2 S) and the dihydropryidine receptor (20 S). Densitometric scanning of the peak dystrophin-glycoprotein containing gradient fractions revealed several proteins which co-purified with dystrophin: a broad, diffusely staining component with an apparent $M_r$ of 156 kDa, 88 kDa protein, a triplet of proteins centered at 59 kDa, 50 kDa protein, a protein doublet at 43 kDa, 35 kDa protein and a 25 kDa protein.

In order to identify the glycoprotein constituents of the dystrophin-glycoprotein complex, sucrose gradient fractions were electrophoretically separated, transferred to nitrocellulose, and stained with peroxidase-conjugated WGA. Four WGA-binding proteins with apparent $M_r$ of 156 k, 50 k, 43 k and 35 k were found to strictly copurify with dystrophin. All four of the WGA-binding proteins were also stained with peroxidase-conjugated concanavalin A. In addition, the lower $M_r$ component of the 43 kDa protein doublet, apparent with Coomassie Blue staining was also stained with concanavalin A. The dystrophin-glycoprotein complex was further characterized with antibodies raised against various components of the complex. Antisera from a rabbit which was immunized with a chemically synthesized decapeptide representing the predicted C-terminal amino acid sequence of human dystrophin was found to stain a single $M_r$ protein. This protein comigrated with the predominant isoform of dystrophin stained by sheep polyclonal anti-dystrophin antibodies.

A library of monoclonal antibodies against muscle proteins eluted from WGA-sepharose was also screened for reactivity against components of the dystrophin-glycoprotein complex. Of six hybridomas which showed immunofluorescence staining only on the sarcolemma monoclonal antibodies XIXC2 and VIA4$_2$ were found to stain dystrophin on immunoblots. Both dystrophin monoclonal antibodies are IgM subtypes, and recognized both native and denatured dystrophin. Monoclonal antibody XIXC2 also recognized the minor lower $M_r$ isoform of dystrophin which appears to copurify with the more abundant isoform.

Two of the other sarcolemma-specific monoclonal antibodies were specific for components of the dystrophin-glycoprotein complex. The 50 kDa glycoprotein stained with monoclonal antibody IVD3$_1$. Monoclonal IVD3$_1$ recognized only the nonreduced form of the 50 kDa glycoprotein and it is not highly crossreactive. Monoclonal antibody VIA4$_1$ stained the 156 kDa glycoprotein which copurified with dystrophin. Monoclonal antibody VIA4$_1$ recognized the denatured form of the 156 kDa glycoprotein and is highly crossreactive.

Immunolocalization of components of the dystrophin-glycoprotein complex in rabbit muscle The indirect immunofluorescence labeling of fixed 8 µm transverse cryostat sections from rabbit gastronimious was carried out as described in Jorgensen, A. O., et al., supra. Sections were preincubated for 20 minutes with 5% normal goat antiserum in phosphate buffered saline, followed by a two hour incubation at 37° C. with the primary antibody (hybridoma supernatants or 1:1000 diluted antiserum). After washing in PBS, the sections were further incubated for 30 minutes at 37° C. in PBS with a 1:50 dilution of FITC-labeled goat F(ab')$_2$ anti-mouse IgG or anti-rabbit IgG and subsequently examined in a Leitz fluorescence microscope. Staining of cryostat sections was not observed with non-immune serum, nor was there any nonspecific binding to the tissue by fluorescein-labeled secondary antibody.

The antisera to the C-terminal amino acid sequence of human dystrophin showed immunofluorescence staining only on the cell periphery which indicates a restricted localization of dystrophin to the sarcolemma of rabbit skeletal muscle. This observation was confirmed by staining rabbit skeletal muscle with monoclonal antibody XIXC2 against dystrophin and, again, localization was observed in the sarcolemma of the rabbit skeletal muscle. The 50 kDa glycoprotein, stained with monoclonal IVD3$_1$, has been localized exclusively to the sarcolemmal membrane of rabbit skeletal muscle. Monoclonal antibody VIA4$_1$ exhibited weak, but specific, immunofluorescent staining of the sarcolemmal membrane consistent with its low affinity for the native 156 kDa glycoprotein. In agreement with immunofluorescence results, a rabbit membrane preparation greatly enriched in sarcolemmal proteins also exhibits a substantial enrichment in dystrophin, the 156 kDa and 50 kDa glycoproteins. Immunofluorescence staining for dystrophin, 50 kDa glycoprotein or the 156 kDa glycoprotein was equally distributed in fast and slow muscle fibers.

Immunoadsorption of the dystrophin-glycoprotein complex

Immunoaffinity beads prepared as described in Campbell, K. P., et al., *J. of Biol. Chem.*, 262:6460–6463 (1987), were equilibrated with buffer A containing 0.5 M NaCl and then incubated overnight (12 hours) with 0.75 ml of fraction 2 from the 1.75 mM NaCl wash of the DEAE-cellulose column as described above. After pelleting, the supernatants were decanted (voids) and the affinity beads were washed with 5×0.7 ml aliquots of buffer A containing 0.5 M NaCl. The void from each affinity column and the five washes were pooled and concentrated to 375 µl in a centricon 100 (Amicon). In addition, 0.75 ml of fraction 2 was diluted to 4.2 ml with buffer A, concentrated to 375 µl and used as control. Column voids were analyzed by SDS-PAGE and immunoblotted as described above.

The voids from the XIXC2 (anti-dystrophin) and the IVD3$_1$ (anti-50 kDa glycoprotein) immunoaffinity beads contained no dystrophin, 59 kDa triplet, 50 kDa glycoprotein, 43 kDa doublet or 35 kDa proteins as detected by Coomassie Blue staining. It was apparent that both the XIXC2 (anti-dystrophin) and IVD3$_1$ (anti-50 kDa glycoprotein) immunoaffinity beads quantitatively removed dystrophin from the starting material. Analysis of the voids for the 156 kDa glycoprotein and the 50 kDa glycoprotein revealed that both the XIXC2 and the IVD3$_1$ immunoaffinity beads selectively adsorbed all but a trace of each of these glycoproteins from the voids while the voltage-sensitive sodium channel, and the alpha$_1$ and alpha$_2$ subunits of the dihydropyridine receptor remained in the voids. As detected by peroxidase-conjugated WGA, the 43 kDa and 35 kDa glycoproteins were also adsorbed from the voids. Immunoblots of immunoaffinity beads separated on gels indicated that dystrophin, the 156 kDa and 50 kDa glycoproteins were retained by the beads and not selectively proteolyzed. Initial experiments with monoclonal VIA4$_1$ (anti-156 kDa glycoprotein) have indicated that it has too low an affinity for the native 156 kDa glycoprotein to be successful in this type of an experiment.

Example 2

Reduction or Absence of 156 kDa Glycoprotein in Dystrophic Mammals

Immunoblot analysis of control and dystrophic mouse muscle membranes

Membranes from control and dystrophic mice (mdx) were prepared in 10% sucrose, 76.8 mM aprotinin, 0.83 mM benzamidine, 1 mM iodoacetamide, 1.1 μM leupeptin, 0.7 μM pepstatin A, 0.23 mM PMSF, 20 mM tris-maleate, pH 7.0, by centrifuging muscle homogenates for 15 minutes for 14,000 XG and subsequently pelleting the supernatant for 30 minutes at 125,000 ×g followed by KCl washing as described above. Control and dystrophic mouse muscle membranes were analyzed by SDS-PAGE and immunoblotting as described above. The amount of 156 kDa glycoprotein in each preparation was estimated densitometrically from autoradiographs of identical blots incubated with $^{125}$I-labeled sheep anti-mouse secondary antibody.

Staining with polyclonal antisera against the C-terminal decapeptide of dystrophin revealed that dystrophin was completely absent from dystrophic mouse membranes. In addition, comparison of normal and dystrophic mouse with immunostaining by monoclonal antibody VIA4$_1$ against the 156 kDa glycoprotein revealed that the 156 kDa glycoprotein was absent or greatly reduced in dystrophic mouse membranes. Staining of identical transfers with sheep polyclonal antisera against either the ryanodine receptor, or the dihydropyridine receptor, did not differ between control and dystrophic mouse muscle membranes. Monoclonal antibody IVD3$_1$ against the 50 kDa glycoprotein did not crossreact with normal mouse membranes and, thus, could not be evaluated. The absence of the 156 kDa glycoprotein was also confirmed using SDS muscle extracts instead of isolated membranes from control and dystrophic mice. Estimation of the 156 kDa glycoprotein remaining in the dystrophic muscle membranes using $^{125}$I-labeled secondary antibodies and total membrane preparations from four different control and four different dystrophic mice revealed an average reduction of 85% in dystrophic muscle.

Immunoblot analysis of normal and dystrophic human muscle biopsies

Frozen muscle biopsy samples (50 mg) were crushed in liquid nitrogen using a mortar and a pestle and then prepared for electrophoresis as described by Hoffman, et al., *N. Eng. J. of Med.*, 318:1363–1368 (1988). The pulverized muscle samples were transferred to ten volumes of SDS-PAGE sample buffer (10% SDS, 2 M sucrose, 4% 2-mercaptoethanol, 0.002% bromophenyl blue, 260 mM tris-HCl, pH 6.8), vortexed, and precipitated material allowed to settle. Aliquots (50 μl) of the SDS-extracted muscle samples were analyzed by SDS-PAGE and immunoblotting and the amount of 156 kDa glycoprotein was estimated.

The dystrophic samples exhibited no staining with antibodies against dystrophin by indirect immunofluorescence microscopy and immunoblotting. In contrast to the normal muscle extract, the 3 DMD samples showed greatly reduced staining for the 156 kDa glycoprotein. On the other hand, identical immunoblots stained with monoclonal antibodies against the $Ca^{2+}$—dependent ATPase revealed no difference in the staining intensity between normal and dystrophic muscle samples. Again, the amount of 156 kDa glycoprotein was estimated to be reduced by approximately 90% in DMD samples.

Example 3

Characterization of Dystrophin-Glycoprotein Complex with Guinea Pig Antisera

Polyclonal antisera reactive with dystrophin-glycoprotein complex

Polyclonal antisera specific for various components of the dystrophin-glycoprotein complex were prepared by two methods. In the first method, (see Sharp, A. H. and Campbell, K. P., *J. Biol. Chem.* 266:9161–9165 (1989)), individual components of the dystrophin-glycoprotein complex (~500 μg) were separated by SDS-PAGE in the presence of 1% 2-mercaptoethanol. The gels were stained for 10 min with Coomassie Blue in 10% acetic acid, 25% isopropanol and destained in distilled water. Individual bands were cut from the gel and frozen in 1 ml of PBS until being used for immunization of guinea pigs. Alternatively, 50 μg of dystrophin-glycoprotein complex in buffer A (0.1% digitonin, 50 mM Tris-HCl, pH 7.4, 0.75 mM benzamidine, 0.1 mM PMSF) was used as immunogen. Animals were boosted on day 14 with 5 μg of the appropriate antigen and monthly thereafter. Antisera were collected weekly after sufficient titers had been achieved. Antisera specific for each component of the dystrophin-glycoprotein complex were affinity-purified using Immobilon-P transfers of individual proteins separated by SDS-PAGE.

Antisera from guinea pigs immunized with purified dystrophin-glycoprotein complex as described by Ervasti et al. (*J. Biol. Chem.* 266:9161–9165 (1991)), showed immunoreactivity to all components of the complex with the exception of the 50 kDa dystrophin-associated glycoprotein. Immobilon-P transfer strips containing individual components of the dystrophin-glycoprotein complex separated by SDS-polyacrylamide gel electrophoresis were used to affinity purify antibodies specific of the 156 kDa, 59 kDa, 43 kDa and 35 kDa dystrophin-associated proteins. Antibodies to the 50 kDa dystrophin-associated glycoprotein were affinity-purified from antisera obtained by immunizing a guinea pig with SDS polyacrylamide gel slices containing the reduced 50 kDa dystrophin-associated glycoprotein. Immunoblot staining of skeletal muscle microsomes, sarcolemma and purified dystrophin-glycoprotein complex demonstrated that each of the affinity-purified antibodies recognized only proteins of the same molecular weight to which they were raised an affinity purified against. This data suggests that the 156 kDa, 59 kDa, 50 kDa, 43 kDa and 35 kDa dystrophin-associated proteins are not proteolytic fragments of larger proteins or dystrophin.

Stoichiometric relationship between complex components

Densitometric analysis of Coomassie Blue-stained SDS-polyacrylamide gels containing the electrophoretically separated components of six different preparations of dystrophin-glycoprotein complex demonstrated that the 59 kDa, 50 kDa, 43 kDa, 35 kDa and 25 kDa dystrophin-associated proteins exhibited average stoichiometric ratios of 1.6±0.22, 0.82±0.11, 0.95±0.14, 1.8±0.19 and 0.36±0.12 relative to dystrophin. However, the stoichiometry of the 156 kDa dystrophin-associated glycoprotein relative to dystrophin has not been determined because it stains poorly with Coomassie Blue. Therefore, the antibody staining intensity was quantitated from autoradiograms of the immunoblots after incubation with [$^{125}$I]-Protein A and was compared to the Coomassie Blue staining intensity of dystrophin in sarcolemma and purified dystrophin-glycoprotein complex. These comparisons indicated that all components of the dystrophin-glycoprotein complex quantitatively coenrich and that the 156 kDa dystrophin-associated glycoprotein is stoichiometric with dystrophin.

Immunolocalization of dystrophin-associated proteins

The cellular localization of the dystrophin-associated proteins was determined by indirect immunofluorescence labeling of transverse cryostat sections of rabbit skeletal muscle. The affinity-purified polyclonal antibodies specific for the 156 kDa, 59 kDa, 50 kDa, 43 kDa and 35 kDa dystrophin-associated proteins exhibited immunofluorescent staining of the sarcolemmal membrane, demonstrating the unique association of these proteins with the muscle fibre plasma membrane or the intracellular cytoskeleton subjacent to the surface membrane. All five polyclonal antibodies against dystrophin-associated proteins illustrated an equal distribution between fast and slow fibers and showed enriched staining at the neuromuscular junction.

Example 4

Characterization of Integral Membrane Components

Alkaline extraction of the dystrophin-glycoprotein complex

Consistent with predictions that it is a cytoskeletal protein, dystrophin can be extracted from skeletal muscle membranes and membranes isolated from the electric organ of *Torpedo californica* in the absence of detergents by simple alkaline treatment. To evaluate which components of the dystrophin-glycoprotein complex are integral membrane proteins, alkaline-treated rabbit skeletal muscle membranes were pelleted (100,000×g) and the soluble supernatant and insoluble membrane pellet analyzed by SDS-polyacrylamide gel electrophoresis and immunoblotting. The supernatant of alkaline-treated membranes contained greater than 90% of all dystrophin while the remaining pellet-associated dystrophin could by extracted with a second alkaline treatment. The 59 kDa dystrophin-associated protein was also extracted by alkaline treatment. On the other hand, dystrophin and the 59 kDa dystrophin-associated protein remained associated with the pellet in membranes diluted in identical buffers which were not titrated to pH 11. The 156 kDa, 50 kDa, 43 kDa, and 35 kDa glycoproteins were retained in the membrane pellet after alkaline treatment. The supernatants obtained from skeletal muscle membranes titrated to pH 11, and pelleted at 100,000×g were also enriched in non- or peripheral membrane proteins such as calsequestrin, the 53- and 160 kDa glycoproteins of the sarcoplasmic reticulum and actin, while the sarcoplasmic reticulum ryanodine receptor, an integral membrane protein, was retained in the pellet. That dystrophin and the 59 kDa dystrophin-associated protein can be extracted from skeletal muscle membranes by alkaline treatment in the absence of detergents demonstrates that these proteins are not integral membrane proteins and suggests both are elements of the cytoskeleton. These data further suggest that the 156 kDa, 50 kDa, 43 kDa and 35 kDa dystrophin-associated glycoproteins are integral membrane proteins.

Incorporation of [$^{125}$I] TID into purified dystrophin-glycoprotein complex

To further asses the hydrophobic nature of the components of the dystrophin-glycoprotein complex, the hydrophobic probe [$^{125}$I] TID was photoincorporated into purified dystrophin-glycoprotein complex. Hydrophobic segments (presumably transmembrane domains) of proteins can be specifically labeled with [$^{125}$I] TID. Dystrophin and the 59 kDa dystrophin-associated protein were not labeled with [$^{125}$I] TID while the 50 kDa, 43 kDa and 35 kDa dystrophin-associated glycoproteins demonstrated roughly equal incorporation of the probe. The large amount of [$^{125}$I] TID incorporation into the 25 kDa dystrophin-associated protein indicates that it is the most hydrophobic component of the complex and may explain why we have been unsuccessful in raising antibodies to it. It is not clear why the 156 kDa dystrophin-associated glycoprotein was not labeled with [$^{125}$I] TID but one explanation may be the occlusion of its transmembrane domain(s) by the other hydrophobic components of the complex.

Effect of alkaline treatment on immunoprecipitation of the dystrophin-glycoprotein complex It has been demonstrated that the components of the purified dystrophin-glycoprotein complex no longer co-sediment on sucrose density gradients after alkaline dissociation. While dystrophin, the 156 kDa and 59 kDa dystrophin-associated proteins exhibited distinct sedimentation peaks after alkaline dissociation, the 50 kDa, 43 kDa and 35 kDa dystrophin-associated glycoproteins appeared to cosediment as a complex. To determine whether the 50 kDa, 43 kDa and 35 kDa dystrophin-associated glycoproteins remains complexed after immunoprecipitation by mAb XIXC2 (dystrophin)-Sepharose or mAb IVD3$_1$ (50 kDa glycoprotein)-Sepharose was analyzed by SDS-polyacrylamide gel electrophoresis and immunoblotting. Both the dystrophin-and 50 kDa dystrophin-associated glycoprotein-antibody matrices were effective in immunoprecipitating greater than 99% of dystrophin and 96% of the 59 kDa, 50 kDa, 43 kDa and 35 kDa dystrophin-associated proteins form untreated dystrophin-glycoprotein complex. Dystrophin- and 50 kDa dystrophin-associated glycoprotein- antibody matrices immunoprecipitated 63% and 85% of the 156 kDa dystrophin-associated glycoprotein. The dystrophin-antibody matrix immunoprecipitated greater than 99% of the dystrophin from the alkaline-treated dystrophin-associated proteins and only 51% of the 59 kDa dystrophin-associated protein indicating that the interaction between dystrophin and the complex was disrupted by alkaline treatment. The 50 kDa dystrophin-associated glycoprotein-antibody matrix immunoprecipitated less than 25%, 32% and 43% of dystrophin-associated proteins from the alkaline-treated complex. However, 96% of the 50 kDa, 43 kDa and 35 kDa dystrophin-associated glycoproteins were immunoprecipitated from the alkaline-treated complex using the 50 kDa dystrophin-associated glycoprotein antibody matrix. Thus, these data demonstrate that the 50 kDa, 43 kDa and 35 kDa dystrophin-associated proteins alone form a tightly-associated complex. Since the 50 kDa dystrophin-associated glycoprotein-antibody matrix immunoprecipitates more of the 156 kDa dystrophin-associated glycoprotein that the dystrophin-antibody matrix, these data further suggest that the 156 kDa dystrophin-associated glycoprotein is directly linked to the 50 kDa, 43 kDa and 35 kDa glycoprotein complex rather than to dystrophin.

Example 5

Dystrophin-Associated Protein Expression in Normal and Dystrophic Murine Skeletal Muscle Isolation of skeletal and cardiac muscle membranes Skeletal and cardiac muscle membranes were prepared from age-matched normal control mice and mdx mice.

During the isolation procedure, membrane preparations from different mice were not combined but kept separate for comparative purposes. Hind leg and back muscle were dissected as quickly as possible and homogenized in 7.5 volumes of homogenization buffer by a Polytron (Kinematic GmbH, Luzern, Switzerland) in the presence of a protease inhibitor cocktail to minimize protein degradation (see Ohlendieck et al., *J. Cell. Biol.* 112:135–148 (1991)). Homogenates were centrifuged for 15 min at 3,000×g and the supernatant filtered through 4 layers of cheese cloth. The pellets from this initial centrifugation step were rehomogenized and centrifuged as above and the supernatants of four repeated homogenization cycles combined. Membrane pellets were obtained by centrifugation of the combined supernatants for 35 min at 140,000×g and the final preparation was KCl-washed as described by Ohlendieck et al., *J. Cell Biol.* 112:135–148 (1991). Cardiac membranes from control and dystrophic dy/dy mice (C57BL/6J-dy; Jackson Laboratory, Bar Harbor, Me.) were prepared as described for control and mdx mouse muscle.

A newly established wheat germ agglutination procedure was employed to isolate purified skeletal muscle sarcolemma (see Ohlendieck et al. *J. Cell Biol.* 112:135–148 (1991)) and dystrophin-glycoprotein complex was prepared from rabbit skeletal muscle as described by Ervasti et al., (*Nature* 345:315–319 (1990)). Protein was determined as described by Peterson (*Anal. Biochem.* 83:346–356 (1977)) using bovine serum albumin as a standard.

Preparation of sheep antisera using native complex immunogen

Monospecific antibodies against the different components of the dystrophin-glycoprotein complex were produced by injecting the native dystrophin-glycoprotein complex purified as described herein into sheep. After testing the crude sheep antisera for the presence of antibodies against the dystrophin-glycoprotein complex, monospecific antibodies to 35 kDa glycoprotein, 43 kDa glycoprotein, 50 kDa glycoprotein and 59 kDa protein were affinity purified from individual immobilon strips of the various components of the dystrophin-glycoprotein complex as described by Sharp et al., (*J. Biol. Chem.* 264:2816–2825 (1989)). Specificity of affinity-purified antibodies was subsequently determined by immunoblot analysis with rabbit sarcolemma and rabbit dystrophin-glycoprotein complex.

Monoclonal antibodies XIXC1 to dystrophin, VIA4$_1$ to 50 kDa glycoprotein, McB2 to Na/K-ATPase (Urayama et al., *J. Biol. Chem.* 264:8271–8280 (1989)) and IID8 to cardiac Ca$^{2+}$-ATPase (Jorgensen et al., *Cell Motil Cytoskel.* 9:164–174 (1988)) were previously characterized by extensive immunofluorescence and immunoblot analysis (Ohlendieck et al., *J. Cell Biol.* 112:135–148 (1991)). Rabbit polyclonal antibodies against the C-terminal sequences of human dystrophin and human dystrophin-related protein (DRP) were affinity-purified and characterized as described (Ervasti et al., *J. Biol. Chem.* 266:9161–9165 (1991)). Monoclonal antibody SB-SP-1 against spectrin was purchased from Sigma Chemical Company (St. Louis, Mo.).

Gel electrophoresis and immunoblot analysis

Proteins were fractionated on 3–12% gradient SDS polyacrylamide gels and protein bands were visualized by Coomassie-blue staining and also analyzed by Stainsall staining. Proteins were transferred to nitrocellulose and immunoblot staining with antibodies and densitometric scanning was carried out as described above. Both protein A and protein G did not label primary sheep antibody sufficiently. Therefore, after primary labeling with sheep antibody, immunoblots of mouse muscle membranes were incubated with rabbit anti-sheep secondary antibody followed by incubation with $^{125}$I-labeled protein A (Amersham Corporation). This procedure gave reproducibly a very strong signal in autoradiography and enabled densitometric scanning of DAP antibody binding to control and mdx mouse muscle membranes.

Lectin-staining of immunoblots was carried out under optimized conditions as described (Campbell et al., *Nature* 338:259–262 (1989); Ohlendieck et al., *J. Cell Biol.* 112:135–148 (1991)). Blots were incubated for 1 hr with 1:1,000 diluted peroxidase-labeled wheat germ agglutinin, concanavalin A and jacalin (Vector Laboratories, Burlingame, Calif.) and developed in 20 mM Tris-Cl, pH 7.5, 200 mM NaCl using 4-chloro-1-napthol as substrate (Jorgensen et al., *J. Cell Biol.* 110:1173–1185 (1990)).

Immunofluorescence microscopy

Immunofluorescence microscopy of 8 μm transverse cryosections from control, mdx and dy/dy mouse skeletal muscle was performed as described by Ohlendieck et al. (*J. Cell Biol.* 112:135–148 (1991)). Following preincubation for 20 min with 5% normal goat antiserum in PBS (50 mM sodium phosphate, pH 7.4, 0.9% NaCl), cryosections were incubated for 1 hr at 37° C. with primary antibodies (1:1,000 dilution of crude antisera or 1:100 dilution of hybridoma supernatant or 1:50 dilution of affinity-purified antibodies). After extensive washing in PBS the sections were labeled with 1:100 diluted affinity-purified fluorescein-labeled goat anti-mouse IgG or goat anti-rabbit IgG (Boehringer-Mannheim) and subsequently examined in a Zeiss Axioplan fluorescence microscope. In the case of mouse monoclonal antibodies used on mouse cryosections, a biotin-streptavidin system was employed for immunodetection. Affinity-purified primary antibodies were biotinylated according to the instructions in the commercially available biotinylation kit from Amersham Corporation. Cryosections were incubated with biotinylated primary antibody as already described for unlabeled primary antibody and subsequently extensively washed in PBS. Finally, sections were fluorescently labeled by incubation with 1:100 diluted affinity-purified fluorescein-conjugated avidin (Sigma Chemical Company).

For labeling of skeleton muscle specimen with wheat germ agglutinin (WGA), cryosections were incubated with 1:2,000 diluted fluorescein-conjugated WGA (Sigma Chemical Company) for 30 min in the presence and absence of 0.3 M N-acetyl-glucosamine. Sections were intensively washed in PBS and then examined for specific labeling in a fluorescence microscope. Histochemical examination of control, mdx and dy/dy mouse skeletal muscle cryosections was performed by haematoxylin and eosin staining as described by Dubowitz (*Muscle Biopsy—A Practical Approach*, London:Bailliere Tindall, 1985, 2nd edition).

Immunofluorescence microscopy of biopsy specimens from patients afflicted with neuromuscular disorders was performed under identical conditions. Cryosections from healthy normal humans of varying age and sex and cryosections from patients suffering from a variety of different neuromuscular disorders (Duchenne muscular dystrophy, Becker's muscular dystrophy, limb girdle dystrophy, congenital muscular dystrophy and spinal muscular atrophy) were placed on the same microscopy slide and the samples therefore treated in an identical manner during all incubation and washing steps. Human muscle biopsy specimen were obtained from the Departments of Pediatrics and Neuropathology, University of Iowa Clinics and Hospitals.

Immunoblot analysis of antibodies to dystrophin-associated proteins

Sheep antiserum raised against the native dystrophin-glycoprotein complex was used to affinity-purify monospecific antibodies to the individual components of the tightly associated dystrophin-glycoprotein complex. The high specificity of the eluted, affinity-purified antibodies was demonstrated by immunoblot. Sheep antibodies to 35 kDa glycoprotein, 43 kDa glycoprotein, 50 kDa glycoprotein and 59 kDa protein exhibited strong labeling of their respective antigen in sarcolemma and isolated dystrophin-glycoprotein complex from rabbit skeletal muscle. These results indicate monospecificity of the affinity-purified antibodies for the different components of the dystrophin-glycoprotein complex and this is a crucial prerequisite for the characterization of components of the complex in control, mdx and dy/dy muscle. Sheep antibodies to 156 kDa glycoprotein did not exhibit strong labeling in immunoblotting and furthermore the affinity-purification of sheep antibodies to 156 kDa glycoprotein is complicated due to contaminating fragments from degraded dystrophin molecules. We therefore used the already previously characterized monoclonal antibody VIA4$_1$ for the analysis of 156 kDa glycoprotein, which is a highly specific probe and exhibits strong labeling in immunoblotting.

Dystrophin-associated proteins in skeletal muscle membranes from mdx mouse

After characterization, the affinity-purified sheep antibodies were used in an extensive immunoblot analysis to compare the expression of components of the dystrophin-glycoprotein complex in skeletal muscle membranes from control and mdx mouse. Mdx mouse is a possible animal model from Duchenne muscular dystrophy which is missing dystrophin due a point mutation in the dystrophin gene. Skeletal muscle fibers from mdx mouse undergo cycles of degeneration and regeneration and it is therefore of considerable interest to examine the status of dystrophin-deficient mdx skeletal muscle. Coomassie-blue and "Stainsall" staining reveals that membrane preparations from control and mdx mouse skeletal muscle are similar in composition. Crude skeletal muscle membranes from mdx mouse are characterized by the absence of dystrophin but contain dystrophin-related protein in normal size and abundance as already previously described for purified sarcolemma.

Prior to the examination of the dystrophin-associated glycoproteins in mdx mouse muscle the general status of glycoproteins and sarcolemma components in the membrane preparation of mdx muscle used in this study was evaluated. It is important to account for possible secondary effects to proteins caused by the ongoing degeneration and regeneration cycles in mdx skeletal muscle fibers. Lectin-staining with wheat germ agglutinin-concanavalin A and jacalin showed that the glycoprotein composition with respect to these three lectins is very comparable in control and mdx mouse muscle membranes. Furthermore, plasma membrane marker Na/K-ATPase was found to be equally distributed in both membrane preparations. These results indicate that the general glycoprotein and sarcolemma protein composition is not severely affected in mdx mouse muscle.

Identical immunoblots were examined for the relative expression of dystrophin-associated proteins in skeletal muscle membranes from control and mdx mouse. The relative abundance of dystrophin-associated proteins of apparent 35 kDa, 43 kDa, 50 kDa, 59 kDa and 156 kDa proteins is greatly reduced in mdx muscle membranes. Densitometric scanning of $^{125}$I-protein A-labeled immunoblots, carried out as described above, revealed a 84%±3 reduction for 35 kDa glycoprotein, 80%±5% reduction for 43 kDa glycoprotein, 83%±5 reduction for 50 kDa glycoprotein, 86%±6 reduction for 59 kDa protein and approximately 80–90% reduction for 156 kDa glycoprotein in mdx muscle membranes when compared to control membranes. The comparative densitometric scanning was performed with individually isolated from five 10-week old control mice and five-week old mdx mice. A similarly reduced expression of dystrophin-associated proteins was also observed in membranes isolated from 5, 20 and 30-week old mdx mice as compared to age-matched control mice. The same results were obtained with crude skeletal muscle membranes, which had not been washed with 0.6 M KCl, and also with microsomal membranes prepared as described by Ohlendieck et al., *J. Cell. Biol.* 112:135–148 (1991). These findings indicate that mdx mouse skeletal muscle are not only deficient in dystrophin, but that in addition the density of the dystrophin-associated glycoproteins is greatly reduced in mdx mouse muscle.

Dystrophin-associated proteins in skeletal muscle membranes from dy/dy mouse

Dystrophic skeletal muscle fibers from the animal model dy/dy mouse have a similar histochemical appearance to skeletal muscle fibers in human muscular dystrophy. However, the genetic locus for the neuromuscular disorder dystrophia muscularis was assigned to mouse chromosome 10. Muscle membranes from dy/dy mouse contain dystrophin of normal size and abundance making this animal model a very good control for the status of dystrophin-associated proteins in necrotic, but dystrophin-containing muscle tissue. Coomassie-blue staining revealed no apparent differences between membranes isolated from control and dy/dy mouse skeletal muscle and the density of dystrophin-related protein is also comparable between both membrane preparations. Most importantly, antibodies to the different dystrophin-associated proteins showed approximately equal amounts of these proteins in skeletal muscle membranes from control and dy/dy mouse. These findings demonstrate that dystrophin-associated proteins are not affected by secondary events in necrotic dy/dy muscle which contains dystrophin. Therefore, the reduced expression of dystrophin-associated proteins in skeletal muscle membranes from mdx mice is most likely a primary event following the absence of dystrophin from the membrane cytoskeleton of mdx muscle.

Example 6

Distribution of Dystrophin-Associated Proteins in Normal and Dystrophic Human Tissue The results disclosed in Example 5 demonstrate the absence, or dramatic reduction in the abundance of, dystrophin-associated proteins in tissue samples from dystrophic mice. The present example discloses a similar finding in human tissue samples by immunofluorescence microscopy and immunoblot analysis.

Biopsy Specimens

Skeletal muscle biopsy specimens were obtained from original diagnostic specimens or discarded surgical material with the approval of the institutional review board for medical projects of the University of Iowa Hospitals and Clinics. Normal human skeletal muscle was obtained from the Department of Surgery, University of Iowa Hospitals and clinics during routine surgical procedures involving different muscles from twenty individuals (6–70 years old) who had no clinical history of neuromuscular disorders. The analysis carried out in the present Example comprised skeletal muscle specimens from 12 DMD patients (3–14 years old) of the University of Iowa Hospitals and Clinics.

Cardiac DMD muscle was obtained at Texas Children's Hospital, Baylor College of Medicine from a 12 year old boy. For comparative purposes, a large number of muscle samples from patients afflicted with other neuromuscular disorders were investigated. These samples were obtained from patients seen in the Adult and Pediatric Neuromuscular Clinics at the University of Iowa Hospitals and Clinics. Besides the routine histopathological diagnosis, muscle biopsy specimens from patients afflicted with neuromuscular disorders were tested for dystrophin. Patient biopsy specimens were quick-frozen in liquid nitrogen-cooled isopentane and stored frozen at −80° C. until use.

Immunofluorescence Microscopy

Immunofluorescence microscopy of 7 μm cryosections from human skeletal muscle specimens was performed as previously described for rabbit muscle. Antibodies used in the experiments described in this Example were from various sources. Monoclonal antibody (mAb) IVD31 to 50-DAG, mAb IIH6 to 156-DAG, mAbs VIA42 and XIXC2 to dystrophin were produced and characterized as described previously. The antibodies to dystrophin do not immunologically cross-react with spectrin, α-actin or dystrophin-related protein and furthermore stain exclusively the sarcolemma of normal human and mouse muscle cryosections, but not DMD or mdx mouse muscle cells, which are lacking dystrophin. Therefore the antibodies used in this investigation are specific probes for human dystrophin which is an important prerequisite for the diagnosis of Duchenne muscular dystrophy and related neuromuscular disorders. Highly specific antibodies against the dystrophin-glycoprotein complex were raised in sheep using the purified dystrophin-glycoprotein complex. Antibodies to the individual components of the dystrophin-glycoprotein complex were affinity-purified from individual Immobilon-P transfer membrane strips as described. While satisfactory immunoblot and immunofluorescence staining of muscle membranes and cryosections from normal and mdx mice was obtained with the serum taken after the first booster injection (see Example 5), human muscle membranes and cryosections were labeled much more strongly by sheep serum taken after a further booster injection with purified dystrophin-glycoprotein complex. Rabbit antibodies to the last 12 amino acids of the C-terminus of dystrophin-related protein (DRP) were previously characterized and do not immunologically cross-react with dystrophin. Monoclonal antibody SB-SP-1 to spectrin was purchased from Sigma Chemical Company.

Depending on the secondary antibodies used, cryosections of skeletal muscle were pre-incubated for 20 min with 5% normal goat serum in PBS (50 mM sodium phosphate, pH 7.4, 0.9% NaCl) or 5% normal rabbit serum in PBS supplemented with 5% bovine serum albumin. Subsequently cryosections were treated in a 1-h incubation at 37° C. with different dilutions of primary antibody. After washing in PBS sections were labeled at 37° C. with 1:200 diluted affinity-purified fluorescein-labeled goat anti-mouse IgG (Boehringer-Mannheim) and subsequently examined in a Zeiss Axioplan fluorescence microscope. In the case of primary sheep antibodies, cryosections were washed in PBS and then incubated for 30 min at 37° C. with 1:500 diluted biotinylated rabbit anti-sheep IgG (Vector Laboratories). Finally, after washing in PBS cryosections were labeled for 30 min at 37° C. with 1:1000 diluted fluorescein-conjugated avidin (Sigma Chemical Company). For labeling of skeletal muscle specimens with wheat germ agglutinin (WGA) cryosections were incubated with 1:1,000 diluted fluorescein-conjugated WGA (Sigma Chemical Company) for 30 min in the presence and absence of 0.3 M N-acetyl-glucosamine.

Prior to the characterization of dystrophin-associated proteins in DMD patients, all human skeletal muscle cryosections used in this investigation were characterized by labeling with antibodies to dystrophin and spectrin, as well as stained with wheat germ agglutinin. In contrast to dystrophin, which is completely missing in DMD skeletal muscle, it was found that the membrane cytoskeletal protein spectrin labels evenly the cell periphery of skeletal muscle fibers from DMD patients. Because this investigation evaluates the status of sarcolemmal glycoproteins the overall wheat germ agglutinin (WGA) staining of different muscle specimens was also examined. Both normal human and DMD skeletal muscle exhibited strong WGA-labeling of the cell periphery, which could be specifically eliminated by pre-incubation with the competitive sugar N-acetyl-glucosamine. In addition to muscle cell surface staining, normal and especially DMD skeletal muscle showed strong lectin binding to the endomysial and perimysial connective tissue. These findings indicate that the majority of WGA-binding components of the skeletal muscle cell periphery are not affected in DMD. This is important in analyzing of the status of dystrophin-associated glycoproteins in DMD muscle. In addition, it was previously shown that no general depletion of plasma membrane glycoproteins occurs in DMD skeletal muscle.

Sheep antibodies to the individual components of the dystrophin-glycoprotein complex, the specificity of which was previously characterized in normal and mdx mouse muscle, were used to evaluate the status of dystrophin-associated proteins in muscle biopsy specimens from DMD patients. Immunofluorescence staining revealed restricted labeling of dystrophin-associated proteins to the cell periphery of normal human muscle fibers. Skeletal muscle cryosections exhibited no staining of the interior of myofibers suggesting a specific association of dystrophin-associated proteins with the sarcolemma membrane of human skeletal muscle. This was previously established for mouse and rabbit skeletal muscle using subcellular fractionation studies and immunofluorescence microscopy. In order to reliably compare all muscle biopsy specimens, cryosections were all placed on the same microscopy slide, labeled with the same concentration of primary and secondary antibodies and were treated in an identical way during all incubation and washing steps. Undiluted affinity-purified sheep antibodies in combination with a biotin-streptavidin system were used for immunodetection. Photographs were taken under identical conditions with the same exposure time so that a direct comparison of immunofluorescence staining intensity could be undertaken. The immunofluorescence analysis of the DMD skeletal muscle specimen reveals the general loss of dystrophin-associated glycoproteins in all 12 DMD patients investigated. Histological examination of DMD skeletal muscle, stained with hematoxylin and eosin, showed severe dystrophic degeneration with a rounded contour of muscle cells, central nucleation, a marked variability of fiber size diameter, scattered necrotic muscle fibers and increased interstitial fibrosis typical for DMD muscle. While the cell periphery of DMD skeletal muscle specimens exhibits normal amounts of spectrin, strong staining for WGA in interstitial connective tissue and a complete lack of dystrophin, it exhibits a drastic loss of 156-DAG, 59-DAP, 50-DAG, 43-DAG and 35-DAG. This was observed in all DMD muscle fibers and did not correlate with the severity of degeneration of individual skeletal muscle fibers. However it should be noted that immunofluorescence staining is not only reduced, but the muscle cell periphery is discontinuously labeled in a patchy fashion. In stark contrast to DMD, dystrophin-associated proteins exhibited normal immunofluorescence labeling of the skeletal muscle cell periphery from patients suffering from limb girdle dystrophy, congenital muscular dystrophy and spinal muscular atrophy. These results demonstrate that a deficiency in dystrophin in human DMD skeletal muscle is accompanied by a specific and substantial reduction in all of the dystrophin-associated proteins.

The results obtained with affinity-purified sheep antibodies to 50-DAG were confirmed by immunofluorescence microscopy with monoclonal antibody $IVD3_1$ against 50-DAG. A 1:100 dilution of $IVD3_1$ hybridoma supernatant produced satisfactory results. Biopsy specimens from DMD patients of varying ages exhibited very low levels of immunofluorescence staining intensity for 50-DAG when directly compared to normal age-matched human muscle. Similar to the results obtained with affinity-purified sheep antibodies, immunofluorescence staining with mAb IVD31 varied in the degree of reduction between individual DMD cases. Besides drastic reduction of immunofluorescence staining intensity, labeling of 50-DAG was observed to be discontinuous in the skeletal muscle cell periphery of DMD patients.

To investigate the status of 50-DAG in necrotic muscle fibers which show no deficiency in dystrophin, specimens from a variety of other neuromuscular disorders were labeled with mAb $IVD3_1$. 50-DAG was found in normal amounts in the cell periphery of muscles from patients afflicted with limb girdle dystrophy, congenital muscular dystrophy and spinal muscular atrophy. Biopsy specimens from two patients suffering from facioscapulohumeral muscular dystrophy and a patient afflicted with Friedreich's ataxia also exhibited normal immunofluorescence labeling of the muscle cell periphery for 50-DAG. These are important findings because they suggest that dystrophin-associated glycoproteins are not severely affected by secondary effects in muscle fiber degeneration. The loss of dystrophin-associated proteins appears to be directly related to a deficiency in the cytoskeletal component dystrophin and was observed in all DMD skeletal muscle fibers independent of the severity of muscle degeneration.

Immunoblot analysis of total human muscle membranes

In order to quantitate the remaining amounts of dystrophin-associated proteins in DMD skeletal and cardiac muscle membranes, immunoblot analysis of total muscle membranes was carried out. Total SDS muscle extracts are routinely used to evaluate the status of the high molecular weight component dystrophin and 156 kDa dystrophin-associated protein in patients. In contrast, total SDS-extracts are not suitable for the study of low molecular weight proteins due to the high density of low molecular weight muscle proteins. Therefore a total membrane fraction of skeletal and cardiac muscle was used to investigate the low molecular weight components of the dystrophin-glycoprotein complex. In addition, an obvious difficulty in studying dystrophin-associated glycoproteins in DMD muscle membranes was the very restricted amount of muscle tissue obtainable from diagnostic biopsies. This problem was overcome by acquiring 2–5 grams of DMD skeletal muscle during spinal fusion surgery. After arrival in the laboratory the tissue was washed in ice-cold phosphate-buffered saline and then immediately processed for centrifugation. The starting material for preparations of cardiac membranes was approximately 1 g of human heart samples.

Control cardiac muscle included explanted heart tissue from a transplant patient and a cardiac autopsy specimen from another individual obtained shortly after death. Muscle samples were homogenized and centrifuged in 7.5 volumes of 20 mM sodium pyrophosphate, 20 mM sodium phosphate monohydrate, 1 mM MgCl2, 0.303 M sucrose, 0.5 mM EDTA, pH 7.0 at 1,100 ×g as described in Example 5. All buffers used were supplemented with a protease inhibitor cocktail to prevent protein degradation. To obtain total membranes, supernatants were filtered through cheese cloth and centrifuged at 135,000 ×g for 37 min. Samples were stored in small aliquots at −135° C. until use. Protein concentration was determined using bovine serum albumin as standard. Membrane proteins were fractionated on 3–12% gradient SDS polyacrylamide gels and transferred to nitrocellulose membranes. Immunoblot staining with antibodies and densitometric scanning of radioactively labeled immunoblots was performed as described previously.

DMD skeletal muscle membranes exhibited increased amounts of dystrophin-related protein but lacked dystrophin. Staining with peroxidase-conjugated lectins (wheat germ agglutinin, concanavalin A, jacalin) did not show differences in the major glycoprotein composition of both membrane preparations. Coomassie-blue staining revealed a comparable overall protein composition of normal and DMD skeletal muscle membranes. However, all of the dystrophin-associated proteins were found to be reduced in DMD skeletal muscle membranes when compared to a membrane preparation from age-matched normal human muscle. Densitometric scanning of identical immunoblots which were labeled with $^{125}$I-labeled Protein-A revealed an approximately 90% reduction for all of the dystrophin-associated proteins in DMD skeletal muscle membranes. The reduction of dystrophin-associated proteins in muscle membranes from DMD patients observed in immunoblotting confirms the finding of a lower density of all of the dystrophin-associated proteins in DMD skeletal muscle cryosections. The fact that dystrophin-associated proteins are detectable in the DMD muscle cell periphery by immunofluorescence microscopy and in DMD muscle membranes by immunoblotting suggests that remaining dystrophin-associated proteins are not present in the cytoplasm but are localized to the sarcolemma membrane and are not degraded.

After establishing the reduction of dystrophin-associated proteins in cryosections and total membranes from DMD skeletal muscle, the status of the individual components of the dystrophin-glycoprotein complex in cardiac DMD muscle was also investigated. Antibodies to dystrophin-associated proteins did not exhibit satisfactory immunofluorescence labeling of human cardiac muscle thus we were not able to investigate their status in cardiac DMD cryosections.

Total membranes from normal human and DMD cardiac specimens were separated by 3–12% SDS-PAGE and analyzed by immunoblotting. Normal human cardiac muscle contains all of the components of the dystrophin-glycoprotein complex as previously found for rabbit skeletal muscle. Cardiac DMD muscle membranes, which completely lacked dystrophin, exhibited near to normal amounts of dystrophin-related protein. By contrast all of the dystrophin-associated proteins were greatly reduced and this is analogous to the findings in skeletal muscle membranes from DMD patients. Densitometric scanning of $^{125}$I-labeled Protein-A immunoblots showed approximately 90% reduction for all of the dystrophin-associated proteins in human cardiac DMD muscle. Immunoblot analysis of two patients afflicted with inherited cardiomyopathy showed similar amounts of all of the components of the dystrophin-glycoprotein complex when directly compared to normal human cardiac muscle. In summary, immunoblotting of total muscle membranes enabled the quantitation of the remaining amounts of the individual components of the dystrophin-glycoprotein complex in skeletal and cardiac DMD muscle. The immunoblot data agrees with the results from immunofluorescence microscopy that all of the dystrophin-associated proteins are dramatically reduced in DMD muscle.

Example 7

Primary Structure of the 43 kDa and 156 kDa Dystrophin-Associated Proteins

The primary sequence of two dystrophin-associated proteins has been established by cDNA cloning and DNA sequencing. In this Example, it is shown that the transmembrane 43 kDa and extracellular 156 kDa dystrophin-associated glycoproteins are encoded by a single mRNA and that the extracellular 156 kDa DAG binds laminin.

Cloning and primary sequence analysis of a precursor protein for the 43/156 kDa DAG Affinity purified guinea pig polyclonal antibodies to the 43 kDa DAG were prepared as described by Ervasti and Campbell, *Cell* 66:1121–1131 (1991)) and used to screen 2×10$^6$ clones of λgt11 expression library. Clone R43-A with a length of 600 base pairs was isolated from a random primed adult rabbit skeletal muscle λgt11 library by immunoscreening. An oligo-dT primed rabbit skeletal muscle cDNA library in λ zapII (Stratagene) was screened at high stringency with a $^{32}$P-labelled cDNA insert from the R43-A clone (random primed labelling kit, Boehringer Mannheim Biochemicals). Clone R43-B overlaps R43-A and extends ~1 kb in the 5' direction. Further clones were isolated from λgt11 libraries: R43-D—random primed λgt11 library, R43-C—oligo-dT primed λgt11 library. To isolate cDNA extending to the 5'-end of mRNA (clone R43-E), a rabbit skeletal muscle cDNA library was constructed using random primed cDNA with λgt11 vector (Stratagene). All cDNA inserts were sequenced either on an Applied Biosystems Incorporated Automatic Sequencer or manually by the dideoxy chain termination method. Sequences were analyzed with the Genetics Computer Group Inc. (Wisconsin package) and PCGene (Intelligenetics) Software.

The 4200 nucleotide cDNA shown in the SEQ ID NO: 1 sequence contains a 2685 nucleotide open reading frame (beginning at nucleotide 170) coding for a polypeptide of 895 amino acids with a calculated molecular mass of 97,029. This polypeptide is referred to herein as dystroglycan. The first 29 amino acids of the open reading frame are predominantly hydrophobic and likely represent a signal peptide. Hydropathy analysis identified a single continuous region of 24 amino acids close to the C-terminal showing characteristics of a transmembrane domain. Four potential N-linked glycosylation sites and numerous potential phosphorylation sites are found in the 97 kDa polypeptide. Finally, no significant sequence homology was detected in the NBRF database between any known proteins and the predicted amino acid sequence of the 97 kDa polypeptide.

Biochemical characterization of the dystrophin-glycoprotein complex has demonstrated that the 43 kDa DAG has hydrophobic properties characteristic of a transmembrane protein and contains Asn-linked oligosaccharides. These properties are consistent with the predicted sequence of the C-terminal half of the 97 kDa polypeptide which contains a potential transmembrane domain and three out of four potential sites for N-glycosylation. The C-terminal origin of 43 kDa DAG was confirmed using an antibody raised in a rabbit against a synthetic peptide corresponding to the 15 C-terminal amino acid residues of the deduced sequence. This anti-peptide antibody specifically recognized the 43 kDa DAG. In addition, peptide sequence determined directly from the 43 kDa DAG matched 783–793 residues of the deduced amino acid sequence of the 97 kDa polypeptide.

N-terminal domain of the 97 kDa precursor encodes 156 kDa DAG

In order to identify the N-terminal domain of the 97 kDa precursor polypeptide, antibodies to different regions of the 97 kDa precursor polypeptide were produced by expressing several overlapping cDNAs encoding different regions in the 97 kDa precursor polypeptide. A set of pGEX vectors (Smith and Johnson, *Gene* 67:31–40, (1988)) were used to express various fragments of DNA for 97 kDa precursor protein as *E. coli* fusion proteins. Fusion protein-A (FP-A) contains residues 665–856 corresponding to the cDNA R43-A found in the expression library with affinity-purified antiserum against 43 kDa DAG. Fusion protein-C (FP-C) contains residues 857–895 which are the C-terminal 38 amino acids of the 97 kDa precursor polypeptide, and does not overlap with FP-A. Fusion protein-B (FP-B) contains residues 367–863 and thus overlaps with FP-A and FP-C, and has a portion of the N-terminal region of the 97 kDa precursor, which is not present in the mature 43 kDa DAG. Fusion protein-D (FP-D) contains residues 62–438 and thus contains only the N-terminal region of the 97 kDa precursor polypeptide. The correct construction of the recombinant plasmids was verified by restriction mapping. To Construct FP-A, the EcoRI insert from R43-A clone with the size of 0.6 kb was cloned into the EcoRI site of pGEX-1. FP-B was constructed by ligation EcoRI insert from R43-B clone (1.5 kb) into the EcoRI site of pGEX-2T. FP-C was made by ligation into the BamHI site of pGEX-1 the BamHI fragment of cDNA R43-C, containing C-terminal sequence with stop codon, representing last 38 amino acids. For the FP-D construct, EcoRI insert (1.2 kb) from R43-D was inserted into pGEX-2T vector digested with EcoRI.

Each recombinant molecule was introduced in *E. coli* DH5a cells. Overnight cultures were diluted 1:10, incubated for one hour and induced for 2 hours with 1 mM IPTG. Cells were resuspended in PBS and sonicated. Fusion proteins were purified from supernatant by affinity chromatography on glutathione-Sepharose (Pharmacia) and eluted with 5 mM glutathione. Dystrophin-glycoprotein complex was isolated as described Lesot et al. (*Cell* 66:1121–1131 (1991)). Sheep polyclonal antibodies to the purified DGC were produced as described Ohlendieck and Campbell (*J. Cell Biol.* 115:1685–1694 (1991)) and anti-fusion protein antibodies were affinity purified from polyclonal antiserum. A peptide representing the 15 carboxyl-terminus amino acids of the 97 kDa cDNA (PKNMTPYRSPPPYVP) (SEQ ID NO: 15) was obtained from the HHMI Peptide Facility (Washington University, St. Louis) as the N-terminal p-benzoylbenzoyl-peptide photoprobe. Peptide was conjugated to keyhole limpet hemocyanin, mixed with Freund's complete adjuvant and injected into a rabbit as immunogen. SDS-PAGE was carried out on 3–12% gradient gels in the presence of 1% 2-mercaptoethanol and transferred to nitrocellulose for immunoblot analysis.

Affinity-purified antibodies were then tested using each fusion protein and purified DGC. Consistent with the C-terminal domain encoding the 43 kDa DAG, antibodies to FP-A and FP-C specifically stained both bands of 43 kDa DAG doublet. However, antibodies to FP-B stained the 43 kDa DAG and the 156 kDa DAG components of DGC. Thus, a second product of 97 kDa precursor polypeptide appears to be the 156 kDa DAG. In accordance with this supposition, antibodies to FP-D stain only 156 kDa DAG. Therefore, posttranslational processing of 97 kDa precursor polypeptide gives rise to two components of DGC: 43 kDa DAG and 156 kDa DAG. Biochemical studies have demonstrated that 156 kDa DAG is not an integral membrane protein and contains N-linked and O-linked glycosylation. These properties are consistent with the predicted N-terminal half of the 97 kDa precursor which does not possess any hydrophobic region, has one potential N-linked glycosylation site and many potential O-glycosylation sites.

Expression of 43/156 kDa DAG in muscle and non-muscle tissues

Tissue distribution of 43/156 kDa DAG was examined by Northeastern blot analysis. Total RNA was isolated by homogenization in RNAzol (Cinna/Biotecx, TX) followed by chloroform extraction. Poly(A) RNA was enriched by oligo-dT cellulose chromatography and resolved on 1.2% agarose gels containing 5% formaldehyde. RNA was transferred to Genescreen Nylon Membranes (NEN Research Products, MA). Prehybridization was performed at 42° C. in 5×SSC, 5×Denhardt's solution, 50% formamide, 10% dextran sulfate and 100 µg/ml of salmon sperm DNA. Probes were hybridized overnight at 42° C. at a specific activity of at least $1\times10^6$ cpm/ml. Membranes were washed at 62° C. in 2×SSC, 0.1% SDS and were exposed to film (X-OMAT AR, Kodak) at −80° C.

A prominent 5.8 kb transcript was detected in mRNA from rabbit skeletal muscle, cardiac muscle and lung. A weaker hybridizing transcript of the same size was found in brain. Northern blot analysis with total RNA from variety of tissues: liver, kidney, diaphragm and stomach also detected a 5.8 kb mRNA in all these tissues. Thus, the 5.8 kb transcript for the 43/156 kDa DAG is present in various muscle and non-muscle tissues, most likely originating from the same gene.

Identification of the 43/156 kDa DAG in muscle and non-muscle tissues was performed using immunoblots of membranes from different tissues and affinity-purified antibodies to FP-B (43/156 kDa specific). Total membranes were prepared from tissues homogenized in 7.5 volumes of homogenization buffer (20 mM sodium pyrophosphate, 20 mM sodium phosphate monohydrate, 1 mM $MgCl_2$, 0.3 M sucrose, 0.5 mM EDTA, pH 7.0) using a Polytron PTS-10-S probe (Kinematic GmbH, Luzern, Switzerland) in the presence of a protease inhibitor cocktail. Homogenates were centrifuged for 15 min at 1100×g and the supernatant filtered through cheese cloth. The supernatants of four repeated homogenizations were combined and centrifuged for 35 min at 140,000×g. The final membrane preparations were KCl-washed as previously described. Immunoblot analysis was performed as previously using 250 µg of skeletal muscle membranes and 500 µg of non-muscle membranes.

The 43 kDa DAG was detected in isolated membranes from skeletal muscle, brain, cardiac muscle and lung. The 156 kDa DAG was detected in skeletal and cardiac muscle membranes, but was slightly lower in molecular weight in cardiac membranes. In brain and lung membranes the molecular weight of the "156 kDa" DAG reactive protein was ~120 kDa. The variability in molecular weight for the "156 kDa" reactive protein is maybe due to differential glycosylation of the core protein in muscle versus non-muscle tissues. Since the extracellular 156 kDa dystroglycan component differs in molecular weight among various tissues, the extracellular component has been named "α-dystroglycan" and the transmembrane component has been named "β-dystroglycan" to avoid confusion.

mRNA and protein expression in dystrophic muscle

RNA blot analysis of skeletal muscle mRNA from control and mdx mice of different ages using cDNA probe R43-B to 43/156 kDa mRNA revealed no reduction of 43/156 kDa DAG mRNA in mdx mice vs control mice. However, as previously observed, the 43 kDa DAG is greatly reduced in mdx skeletal muscle membranes. Thus, the absence of dystrophin causes no change in the mRNA for the 43/156 kDa DAG but leads to dramatic reductions in the amount of the 43 kDa DAG and 156 kDa DAG in skeletal muscle. Analysis of mRNA from control and DMD skeletal muscle also showed no difference in 43/156 kDa DAG mRNA expression. In agreement with findings in mdx mouse muscle, indirect immunofluorescence analysis of cryosections from normal and DMD skeletal muscle with 156 kDa specific (anti FP-D) and 43 kDa specific (anti FP-A) antibodies demonstrated a drastically reduced density of 43 kDa DAG and 156 kDa DAG in skeletal muscle of a DMD patient. Thus, 43/156 kDa DAG encoding gene is transcribed and specific mRNA is still present at the normal level in dystrophic muscle, but the 43 kDa DAG and 156 kDa DAG are greatly reduced in dystrophic muscle.

Since the 43/156 kDa DAG is expressed in non-muscle tissues we also examined expression of 43 kDa DAG in non-muscle tissues of control and mdx mice. The 156 kDa DAG could not be tested because polyclonal antibodies to the protein core of rabbit 156 kDa DAG described above do not cross react with the 156. DAG in mouse muscle. Immunoblot analysis of brain and kidney membranes from control and mdx mice, stained with polyclonal anti FP-A antibodies (43 kDa specific), revealed no reduction in the amount of 43 kDa DAG in these mdx tissues. Thus, the dramatic reduction of the 43 kDa DAG that is found in mdx mice appears to be restricted to skeletal muscle and is not found in non-muscle tissues.

156 kDa DAG binds laminin

To test for the association of the 156 DAG with the extracellular matrix, rabbit skeletal muscle surface membranes and pure DGC were electrophoretically separated, transferred to the nitrocellulose membranes and overlaid with $^{125}$I-labeled laminin. More specifically, rabbit skeletal muscle crude membranes, sarcolemma membranes and dystrophin-glycoprotein complex were electrophoretically separated on 3–12% SDS polyacrylamide gels in the presence of 1% 2-mercaptoethanol and transferred to nitrocellulose. Purified laminin mouse EHS (Sigma) was iodinated with $^{125}$I Na using a lactoperoxdase/glucose oxidase reaction by the Diabetes, Endocrinology Research Center at the University of Iowa. The $^{[125I]}$-laminin overlay procedure of Smalheiser and Schwartz (Proc. Natl. Acad. Sci. USA 84, 6457–6461, (1987)) was performed as described except that nitrocellulose transfers were blocked with 5% nonfat dry milk in 150 mM NaCl, 50 mM sodium phosphate, pH 7.5. To test for co-immunoprecipitation of laminin and the 156 Ka dystrophin-associated glycoprotein, pH 12 extracts (Ervasti et al., Nature 343, 315–319 (1990)) of rabbit skeletal muscle surface membranes were incubated for 24 h at 4° C. with gentle mixing buffer A (0.14 M NaCl, 1 mM $CaCl_2$, 1 mM $MgCl_2$, 10 mM triethanolasine-HCl, pH 7.6) in the absence or presence of 50 µg of purified mouse EHS laminin (Sigma), then incubated for an additional 24 h at 4° C. with 100 ml of either protein A-Sepharose or anti-laminin/protein A-Sepharose which had been equilibrated with 3% BSA in buffer A and washed four times with buffer A. The Sepharose was pelleted by a brief centrifugation, the supernatant (void) decanted and the Sepharose washed three times with buffer A. Equivalent volumes of the resulting voids and washed Sepharose pellets were analyzed by SDS-polyacrylamide gel electrophoresis and immunoblotting using monoclonal antibody IIH6 which is specific for the 156 kDa DAG.

A single laminin binding band, corresponding to the 156 kDa DAG was detected in surface membranes and purified DGC. Binding of $^{125}$I-laminin to the 156 DAG was significantly decreased by a 1000-fold excess of unlabeled laminin demonstrating the specificity of $^{125}$I-laminin binding to the 156 kDa DAG. $^{125}$I-Fibronectin did not label the 156 kDa DAG or any other component of the DGC, nor did a 1000-fold excess of nonradioactive fibronectin have any effect on the binding of $^{125}$I-laminin to the 156 kDa DAG. The interaction of 156 kDa DAG with laminin was also shown by co-immunoprecipitation of laminin and 156 kDa DAG. Anti-laminin antibodies did not precipitate the 156 kDa DAG from alkaline extracts of rabbit skeletal muscle surface membranes. This result was consistent with the observation that the surface membranes used were devoid of laminin, merosin, or S-laminin as detected on immunoblots using specific antibodies. However, anti-laminin antibodies effectively precipitated the 156 kDa DAG from alkaline extracts which had been preincubated with exogenously added laminin. These results suggest that the 156 kDa DAG specifically binds laminin and may mediate interaction of DGC to extracellular matrix.

Example 8

Human Dystroglycan cDNA

Cloning and Analysis of Human Dystroglycan cDNA

The rabbit specific insert from clone R43-B (corresponding to the 156/43 coding region) was used to probe a human skeletal muscle library in λgt10. Screening of 106 clones was performed with a $^{32}$P-labeled cDNA insert from R43-B rabbit clone (random primed labeling kit, Boehringer Mannheim). Hybridization was performed in 2×Pipes, 50% deionized formamide, 0.5% SDS, 100 µg/ml denatured salmon sperm DNA with 10$^6$ counts/ml of probe at 42° C. overnight. Washes were done in 0.1×SSC, 0.1% SDS at 65° C. The first human clone isolated was designated HD-1 (~2.6 kb).

By several rounds of screening the cDNA library with human-specific probes corresponding to the 5' or 3' end of HD-1, several additional clones were isolated. Four overlapping clones (designated HD-1 to HD-4) covering the entire mRNA were completely sequenced. The full-length human cDNA consists of 5510 nucleotides (SEQ ID NO: 7), of which 2685 nucleotides represent an open reading frame. A polyadenylation sequence and poly(A) tail were also identified. The deduced amino acid sequence (SEQ ID NOS: 7 and 8) predicts a polypeptide of a calculated Mr of 97,552 with a signal sequence of 27 amino acids, a single transmembrane domain close to the C-terminal region, four potential N-glycosylation sites and many potential sites for O-glycosylation.

Conservation of dystroglycan between species

Alignment of amino acid sequences for human and rabbit dystroglycan demonstrate that both proteins contain 895 amino acids with overall sequence identity of 93%. Ninety percent of the amino acid substitutions are conservative. The transmembrane domain of human dystroglycan is identical to that of rabbit dystroglycan. The intracellular C-terminal region of human and rabbit dystroglycan is highly conserved and is enriched in proline (23%). Both proteins have identical consensus sites for N-glycosylation and have high content of threonine and serine as potential sites for O-glycosylation. High homology between rabbit and human dystroglycan suggests its functional importance, especially in terms of carbohydrate chain attachment sites, since carbohydrates may play an important role in laminin binding.

To characterize further the conservation of dystroglycan among mammalian species, Southern hybridization was performed on DNA isolated from a variety of species (including marmoset, pig, hamster, rat mouse, sheep, cow, rabbit, cat and dog) using the human HD-2 cDNA and high stringency conditions. The same conditions were used for all Southern blots as described above strong hybridization signals of similar intensities were detected on all DNA preparations.

Dystroglycan is encoded by a single gene

The human gene for dystroglycan was characterized by genomic Southern analysis. DNA isolated from lymphocytes of peripheral blood from two individuals (DNA1 and DNA2) was digested with EcoRI, HindIII, KpnI and PstI and transferred to nitrocellulose. The blot was probed with $^{32}$P-labeled HD-2 cDNA. Prehybridization was done in 6×SSC, 5×Denhardt's solution, 10% dextran sulfate, 1% SDS and 100 mg/ml salmon sperm DNA at 65° C. For overnight hybridization at 65° C., 2×10$^6$ cpm/ml of $^{32}$P-labelled HD-2 cDNA was used. Washes were performed as follows: twice in 2×SSC, 0.5% SDS for 10 minutes at room temperature, once in 1×SSC, 1% SDS for 15 minutes at 65° C., twice in 0.1×SSC, 1% SDS for 15 minutes at 65° C. The blot was exposed to X-ray film at −80° C.

The patterns of hybridization with DNA1 and DNA2 digested with HindIII, KpnI, PstI were identical. Hybridization with EcoRI digested samples showed one 12 kb EcoRI band in DNA1, but two EcoRI fragments (9 kb and 3 kb) in DNA2, suggesting EcoRI polymorphism. The simple predictable hybridization pattern suggests the existence of a single gene for human dystroglycan.

Genomic organization of human dystroglycan

Two independent libraries were constructed from partially EcoRI-digested human DNA1 and DNA2 using the EMBL3 vector. Approximately 2×10$^6$ independent clones were obtained. Libraries were screened with $^{32}$P-labeled cDNA HD-1. Several hybridizing clones were isolated and characterized. Two clones, G1 and G2 originating from DNA1 and DNA2 respectively, were chosen for further analysis. Restriction analysis demonstrated several EcoRI fragments within each recombinant phage, including 12 kb in G1 and 9 kb in G2 which were detected previously by Southern blot hybridization. Southern blot analysis using HD-2 cDNA as a probe identified these fragments specifically. The 12 kb and 9 kb EcoRI inserts were subcloned into pUC19 for further analysis and a physical map of these fragments was generated. Based on this map, the 12 kb EcoRI fragment was digested into small subclones and partially sequenced. The combination of sequencing, hybridization and PCR analysis of cloned genomic fragments and comparison with cDNA sequence resulted in the proposed genomic structure of the 12 kb EcoRI-fragment shown in FIG. 1. Interestingly, the majority of coding sequence of human dystroglycan (2.4 kb out of 2.7 kb) together with part of 3'-untranslated region is organized in one large exon, which starts at nucleotide 681 of the DNA sequence shown in SEQ ID NO: 7. The rest of the 3'-untranslated region is organized in other exons and needs further characterization. Upstream of this exon a large intron was identified which spans more than 6 kb of genomic sequence. The polymorphic EcoRI site was mapped downstream of the coding region. To isolate a genomic DNA fragment containing exon sequence encoding the initiator methionine, the genomic library constructed from DNA1 was screened with $^{32}$P-labeled cDNA representing the first 280 nucleotides of coding sequence as well as the 5' untranslated region. Southern blot analysis of EcoRI-digested DNA1 and DNA2 with the above probe showed specific hybridization to a 6.5 kb EcoRI-fragment. This 6.5 kb genomic EcoRI-fragment (clone G3) was isolated, mapped and partially sequenced. The exon, encoding part of the 5'-untranslated region and 285 nucleotides of coding sequence, including the initiating methionine codon was identified. The exon(s) containing the rest of the 5'-untranslated region, transcription initiation site and upstream region were not analyzed. Clones G1 and G3 do not overlap in their intronic sequence, suggesting that the intron is more than 10 kb in size. Thus, the human dystroglycan coding sequence is organized into two exons, a small first exon separated from a large second exon by a large intron.

Tissue-specific expression of human dystroglycan

The tissue-specific expression of dystroglycan was examined by northern blot analysis. Radioactively labeled cDNA HD-2, which is specific to exon 2, was hybridized to 2 µg mRNA from human adult muscle (skeletal and cardiac) and non-muscle tissues (brain, lung, liver, kidney and pancreas). The mRNA blot was prehybridized at 42° C. in 5×SSC, 5×Denhardt's solution, 50% formamide, 10% dextran sulphate and 100 mg/ml of salmon sperm DNA. The membrane was hybridized with $^{32}$P-labeled HD-2 cDNA overnight at 42° C. at a 1×10$^6$ c.p.m./ml. Membranes were washed at 62° C. in 2×SSC, 0.1% SDS and were exposed to film (X-OMAT AR, Kodak) at −80° C. A band of 5.8 kb was detected in all tissues examined. The mRNA is most abundant in skeletal muscle and heart and less abundant in non-muscle tissues. mRNA from several fetal tissues was probed with exon 1 sequence. Interestingly, the same size dystroglycan specific transcript was detected in all tissues examined, which demonstrates that dystroglycan is expressed in fetal and adult muscle and non-muscle tissues. Since the 5.8 kb band is detected in all tissues examined by using probes specific for exon 1 or exon 2, it can be concluded that dystroglycan transcripts are identical in these tissues. In addition, RT-PCR was used to amplify skeletal-muscle specific exon 1 from adult brain and cardiac RNA using two sets of primers. The first set contained a sense primer upstream of ATG codon and an antisense primer corresponding to the end of exon 1. The second set contained the same sense primer and antisense primer, corresponding to the beginning of the exon 2. First strand cDNA was synthesized from 0.5 mg of either human brain or cardiac mRNA. RNA was preheated at 70° C. for 2 minutes and incubated in 50 mM Tris-HCl, 75 mM KCl, 3 mM MgCl2, 0.5 mM each dNTP, 20 pmole random hexamer primer, 1 unit/ml RNase inhibitor and 200 units/mg RNA M-MLV Reverse transcriptase at 42° C. for 1 hour in total volume of 100 ml. For each amplification 5 ml of 1st-strand cDNA was used. PCR was carried out by 25 cycles of denaturation at 94° C. (1 min), annealing at 65° C. (1 min), extension at 72° C. (1 min) under conditions recommended by the manufacturer (Perkin Elmer Cetus). The identical amplification products of predicted size based on the skeletal muscle cDNA were detected in brain and heart for each set of primers. This further demonstrates that tissue specific isoforms do not differ by the primary structure.

Chromosomal localization of human dystroglycan

The chromosomal localization of the dystroglycan gene was first determined by Southern blot analysis of a panel of human/hamster cell hybrids using a radiolabeled dystroglycan cDNA probe. Radioactively labeled dystroglycan cDNA was hybridized to a Southern blot of Bgl II-digested genomic DNA from normal human and Chinese hamster controls and 11 human x Chinese hamster somatic cell hybrid lines derived from six independent fusion experiments (see Franke et al., *Cold Spring Harbor Symp. Quant. Biol.* 51:855–866 (1986)). Prehybridization and hybridization solutions consisted of 4×SSC/5×Denhardt's solution/100 mM Na$_2$HPO4, 1% SDS and 0.1 mg/ml salmon sperm DNA. Hybridization, post-hybridization washes and film exposure were as described.

A 10 kb Bgl II human specific fragment was detected. This fragment was seen in the normal human control and in all hybrids which retained an intact copy of human chromosome 3. All other chromosomes were excluded by at least four discordant hybrids. One hybrid in the mapping panel contained an isochromosome of the long arm of human chromosome 3 [i(3q)] which spontaneously arose in the subcloning of this hybrid. The 10 kb human-specific Bgl II fragment was not detected in this hybrid. Therefore, the dystroglycan gene locus was localized to the short arm of chromosome 3.

This regional assignment was confirmed and further defined by fluorescence in situ hybridization (FISH). A plasmid containing a genomic 9 kb insert (clone G2) specific for dystroglycan was biotin-11-dUTP labeled by nick-translation (Boehringer Mannheim) and hybridized to human metaphase chromosomes prepared by a 17 hr synchronization with methotrexate and a 5 hr release with BrdU and standard cytogenetic methods. This procedure generates an R-banding pattern when chromosomes are counterstained with propidium iodide. Hybridization solution consisted of 6.5 ng/µl labeled probe, 200 ng/ml each of human placental and salmon sperm DNA as competitors, 50% formamide, 10% dextran sulfate and 2×SSC. FISH was carried out essentially as previously described using a biotin/avidin/FITC detection system (see Milatovich et al., *Genomics* 11:1040–1048 (1991)). The location of fluorescent signals was recorded with reference to the R-banding pattern on chromosomes. Metaphase spreads were examined using a Zeiss Axiophot microscope equipped with epifluorescence. Images were captured using a cooled charge coupled device (CCD) camera (PM512, Photometrics) and a Macintosh computer using the GeneJoin program (developed by Tim Rand, Yale University). These PICT images were made into color slides and converted into photographs. Specific signals were observed on at least one chromosome 3 homolog at band p21. Seven of these 11 metaphases with specific signals had both chromosome 3 homologs labeled, and no other chromosomes had specific signals. The somatic cell hybrid analysis and in situ hybridization discovered only one site of specific hybridization, which further supports the conclusion that DAG1 is a single copy gene.

Example 9

Dystrophin-Associated Protein in Autosomal Muscular Dystrophy Affected Tissue

Autosomal muscular dystrophy is a form of muscular dystrophy resulting from a mutation which maps to an autosome. It has been determined that in most cases of autosomal muscular dystrophy, dystrophin is present in affected tissue at near normal levels. This example discloses, however, that in muscle tissue from an individual afflicted with autosomal muscular dystrophy, levels of all of the dystrophin-associated proteins are substantially reduced.

Muscle biopsy tissue from an individual afflicted with autosomal Fukuyama congenital muscular dystrophy (FCMD) was prepared in sections as described, for instance, in Examples 4 and 5. The tissue samples were contacted with affinity purified sheep primary antibodies followed by fluorescein labeled secondary antibodies as described previously. Tissue samples from normal human muscle and Duchenne muscle were similarly treated as control samples.

Dystrophin and all of the dystrophin-associated glycoproteins were found to be present in normal tissue, but absent or substantially reduced in DMD muscle. However, in FCMD tissue immunostaining for all of the dystrophin-associated glycoproteins was diminished while dystrophin was not substantially reduced.

Example 10

Reduction in Level of 50 kDa Dystrophin-Associated Protein in Severe Childhood Autosomal Recessive Muscular Dystrophy In a first experiment, the pattern of expression of dystrophin and dystrophin-associated proteins in biopsied skeletal muscle was analyzed by immunohistochemical techniques. Skeletal muscle biopsy samples were obtained from a 5-year old male with SCARMD, a 10-year old male with SCARMD, an 11-year old female with SCARMD and an 11-year old male with SCARMD. The diagnosis of SCARMD was made based on the following: 1) DMD-like phenotype affecting both males and females, 2) mode of inheritance compatible with an autosomal recessive disease, 3) North African patients, 4) elevated serum creatine kinase level and 5) normal expression of dystrophin in biopsied skeletal muscle analyzed by both immunohistochemistry and immunoblotting (Khurana et al., Neuromusc. Dis. 1: 185–194 (1991)). Control samples included a biopsy sample from a 16-year old male with no pathological changes in skeletal muscle and an 8-year old male with DMD.

Serial transverse cryosections were immunostained with VIA4$_2$, a monoclonal antibody against dystrophin, and affinity-purified sheep polyclonal antibodies against 156 kDa, 59 kDa, 50 kDa, 43 kDa and 35 kDa dystrophin-associated proteins as described above.

In normal skeletal muscle, antibodies against dystrophin and dystrophin-associated proteins stained the sarcolemma. In related experiments, no abnormality of these proteins was observed in biopsy samples from individuals afflicted with the following neuromuscular diseases: limb-girdle muscular dystrophy, myotonic dystrophy, faciosacpulohumeral muscular dystrophy, oculopharyngeal muscular dystrophy, non-Fukuyama type congenital muscular dystrophy, congenital fiber type disproportion, spinal muscular atrophy and amyotrophic lateral sclerosis. In DMD patients, dystrophin was absent and the immunostaining for all of the dystrophin-associated proteins was substantially reduced in the sacrolemma, except at the neuromuscular junction and in the sarcolemma of intrafusal muscle fibers.

However, in all four SCARMD patients including two siblings, immunostaining for the 50 kDa dystrophin-associated protein was substantially reduced in the sarcolemma of all muscle fibers including the neuromuscular junction and the sarcolemma of intrafusal muscle fibers, while immunostaining for dystrophin, 156 kDa, 59 kDa and 43 kDa was preserved. The loss of 50 kDa dystrophin-associated protein in SCARMD patients was more severe than in DMD patients. Immunostaining for 35 kDa dystrophin-associated protein in SCARMD patients was reduced compared with normal control but was not so severely reduced as in DMD patients.

Loss of the 50 kDa dystrophin-associated protein in the sarcolemma of SCARMD patients was confirmed using three other specific antibodies against the 50 kDa dystrophin-associated protein. These antibodies included a IVD3$_1$ (a monoclonal antibody against the 50 kDa dystrophin-associated protein), a sheep polyclonal antibody affinity-purified against the 50 kDa dystrophin-associated protein peptide disclosed in SEQ ID NO:2 and an affinity-purified guinea pig polyclonal antibody.

In a second experiment, designed to confirm the deficiency of the 50 kDa dystrophin-associated protein in SCARMD patients, immunoblot analysis of skeletal muscle biopsy SDS extracts was performed. Biopsy samples were obtained from a 5-year old male with SCARMD, a 41-year old female with facioscapulohumeral muscular dystrophy, a 10-year old male with no pathological changes in the skeletal muscle and an 11-year old female with SCARMD. Cryosections from skeletal muscle biopsy specimens were homogenized in 50 volumes of SDS-extraction buffer (80 mM Tris HCl (pH 6.8), 10% SDS, 0.115 M sucrose, 1% β-mercaptoethanol, 1 mM PMSF, 1 mM benzamidine and 1 mM EDTA) and incubated at 50° C. for 10 minutes. After centrifugation, 10 μl of samples were separated on a 3–12% polyacrylamide gel. The gel was stained with Coomassie blue and the density of the myosin heavy chain (MHC) band was measured using a computing laser densitometer (Model 300S; Molecular Dynamics, Sunnyvale, Calif.). Based on this result, samples were run on a 3–12% polyacrylamide gel so that the amount of MHC was equal for all specimens. Transfer to the nitrocellulose membrane and immunostaining with antibodies were performed as described above.

The antibodies used in the staining procedure included polyclonal antibodies against the last 10 amino acids of dystrophin (ANTI-DYS), a monoclonal antibody against the 156 kDa dystrophin-associated protein (IIH6) and a mixture of affinity-purified sheep polyclonal antibodies against the 59 kDa, 50 kDa and 43 kDa dystrophin-associated proteins. The affinity purified sheep polyclonal antibody against the 35 kDa dystrophin-associated protein was not strong enough to stain the 35 kDa dystrophin-associated protein in crude muscle extracts.

While dystrophin, 156 kDa dystrophin-associated protein, 59 kDa dystrophin-associated protein and 43 kDa dystrophin-associated protein were detected, 50 kDa dystrophin-associated protein was undetectable in all four SCARMD patients.

Example 11

Determination of 50 kDa Dystrophin-Associated Protein Antigenic Peptide Sequence The components of the purified dystrophin glycoprotein complex were separated by polyacrylamide gel electrophoresis followed by transfer to nitrocellulose paper to form a protein transfer blot. The 50 kDa species was separated from other components of the protein transfer blot, and subjected to trypsin digestion using standard protocols. Digestion products were separated by reverse phase HPLC and subjected to protein sequence analysis. Five peptide sequences were determined through this set of experiments. These sequences are provided as SEQ ID NOS:2–6.

One peptide sequence, Pro Arg Pro Leu Ser Thr Leu Pro Met Phe (SEQ ID NO:2) was chemically synthesized and attached to a solid support to generate an affinity matrix. An affinity column was prepared using this matrix and a polyclonal antibody preparation, prepared by immunizing animals with purified dystrophin-glycoprotein complex, was passed over the column. Polyclonal antibodies specifically reactive with this peptide were isolated using this affinity purification method. Thus, the peptide sequence identified represents an immunogenic epitope of the 50 kDa dystrophin-associated protein.

Peptides identified in this manner can be used to immunize animals to generate antibodies specifically reactive with a single epitope of the 50 kDa protein. In addition, degenerate probes can be designed which can then be used in combination with conventional molecular biological techniques to isolate the gene which encodes the 50 kDa dystrophin-associated protein.

Example 12

Isolation of DNA Encoding Rabbit and Human 50 kDa Dystrophin-Associated Protein Affinity-purified antibodies against 50 kDa dystrophin-associated glycoprotein were used to screen a rabbit skeletal muscle cDNA expression library in λgt11. An initial clone was found to contain regions of identity with sequences obtained from two proteolytic fragments of 50 kDa dystrophin-associated glycoprotein. This cDNA molecule was used as a probe for homology screening of rabbit and human skeletal muscle cDNA libraries to obtain full-length 50 kDa dystrophin-associated glycoprotein cDNA clones.

A 1474-bp rabbit cDNA molecule was obtained which contained a single open reading frame of 1161 bp encoding 387 amino acids as shown in SEQ ID NOS. 9 and 10. The assigned initiating residue was the first methionine following the first termination codon upstream of an open reading frame encoding five regions of homology to 50 kDa dystrophin-associated glycoprotein protein sequence. Nine of ten nucleotides surrounding the first methionine match those of the vertebrate consensus site for initiation of translation. A full-length human 50 kDa dystrophin-associated glycoprotein cDNA clone has also been obtained and is shown in SEQ ID NO. 11. The human and rabbit 50 kDa dystrophin-associated glycoprotein nucleotide sequences are 74.6% identical overall.

The rabbit cDNA, sequence has been confirmed to encode 50 kDa dystrophin-associated glycoprotein by several methods. First, protein sequences were obtained from five distinct proteolytic fragments of 50 kDa dystrophin-associated glycoprotein, and all five are present in the deduced amino acid sequence of this clone. Second, antibodies affinity purified against a synthetic peptide corresponding to amino acids 354 to 363 of rabbit 50 kDa dystrophin-associated glycoprotein from sheep anti-DGC serum recognized the 50-kDa component of purified DGC. Third, polyclonal antiserum generated against a synthetic peptide comprised of the 15 C-terminal amino acids of the deduced rabbit 50 kDa dystrophin-associated glycoprotein amino acid sequence recognizes the 50-kDa component of the purified DGC. Fourth, antibodies which were affinity purified against fusion protein H (FP-H) from anti-DGC guinea pig serum or FP-G from anti-50 kDa dystrophin-associated protein sheep serum recognized the 50-kDa component of purified DGC.

Human and rabbit 50 kDa dystrophin-associated glycoprotein deduced amino acid sequences are 86% identical overall (compare, for example SEQ ID NOS: 10 and 12). The 50 kDa dystrophin-associated glycoprotein is predicted to contain a 17-amino-acid hydrophobic signal sequence, suggesting that the N-terminal 290 amino acids of the 50 kDa dystrophin-associated glycoprotein are extracellular. The 50 kDa dystrophin-associated glycoprotein has a single hydrophobic, putative membrane-spanning domain followed by a 76-amino-acid intracellular C-terminal domain. Two consensus sites for N-linked glycosylation are present in the putative extracellular domain, which is consistent with biochemical evidence that 50 kDa dystrophin-associated glycoprotein is N-glycosylated in vivo. Given that rabbit skeletal muscle 50 kDa dystrophin-associated glycoprotein is N-glycosylated, the finding that all N-linked glycosylation sites within the 50 kDa dystrophin-associated glycoprotein sequence lie N-terminal to the membrane spanning domain is further evidence that the N-terminus must be extracellular. Two consensus sites for phosphorylation were identified, one for by casein kinase II and one for calmodulin kinase. It is not known if 50 kDa dystrophin-associated glycoprotein is phosphorylated in vivo. Five extracellular cysteines are conserved between rabbit and human 50 kDa dystrophin-associated glycoprotein. The binding of the anti-50 kDa dystrophin-associated glycoprotein monoclonal antibody IVD3$_1$ on immunoblots requires nonreducing conditions, suggesting that at least one intramolecular disulfide bond is present in vivo. Based on the almost perfect conservation of amino acids surrounding four of these cysteines [$(CX_{12}CX_9CX_{12}C)$, amino acids 199–245], it is possible that disulfide bond formation may be important to this protein's function.

The primary structure of 50 kDa dystrophin-associated glycoprotein yields few clues to its function. The disruption of the DGC due to a lack of 50 kDa dystrophin-associated glycoprotein in the cardiomyopathic hamster demonstrates that this protein plays an important role in holding the complex together. However, it is possible that 50 kDa dystrophin-associated glycoprotein has functions other than a structural one. Further biochemical characterization of the DGC in general and 50 kDa dystrophin-associated glycoprotein in particular is required to elucidate other possible functions of this protein.

Northern blot analysis revealed that 50 kDa dystrophin-associated glycoprotein is exclusively expressed in striated muscles. Expression of 50 kDa dystrophin-associated glycoprotein mRNA is highest in skeletal muscle, cardiac muscle, and diaphragm. Lower amounts of 50 kDa dystrophin-associated glycoprotein transcripts were detected in bladder and small intestine, indicating that 50 kDa dystrophin-associated glycoprotein may be expressed in smooth muscle cells in these tissues. However, immunohistochemistry or in situ hybridization will be required to precisely identify the cell type of origin. 50 kDa dystrophin-associated glycoprotein cDNA hybridized primarily to a band of approximately 1.5 kb, suggesting that use of alternative splice sites or alternative sites for initiation and termination of transcription occurs rarely, if at all.

Example 13

Isolation of DNA Encoding 59 kDa Dystrophin-Associated Protein

Affinity-purified antibodies against 59 kDa dystrophin-associated glycoprotein were used to screen a rabbit skeletal muscle cDNA expression library in λgt11. An initial clone was found to contain regions of identity with sequences obtained from a proteolytic fragment of 59 kDa dystrophin-associated glycoprotein. This cDNA molecule was used as a probe for homology screening of rabbit skeletal muscle cDNA libraries to obtain full-length 59 kDa dystrophin-associated glycoprotein cDNA clones. The nucleic acid sequence encoding the rabbit 59 kDa dystrophin-associated glycoprotein is shown in SEQ ID NO. 13.

A labeled DNA probe corresponding to a portion of SEQ ID NO. 13 was used to mRNA blots from human skeletal muscle cells by Northern blot analysis. A single, strongly cross-hybridizing species was identified demonstrating that the human counterpart of the rabbit 59 kDa dystrophin-associated glycoprotein is sufficiently homologous to facilitate its isolation by hybridization and standard cloning techniques.

Equivalents

Those skilled in the art will recognize or be able to ascertain, using no more than routine experimentation, many equivalents to the specific embodiments of the invention described herein. Such equivalents are intended to be encompassed by the claims which follow.

We claim:

1. A method for producing a polyclonal antibody which binds specifically to the 43 kDa dystrophin-associated protein, the molecular weight of the protein being determined by electrophoretic separation under denaturing conditions, transfer to a solid support and staining with wheat germ agglutinin, the method comprising:

a) providing the peptide PKNMTPYRSPPPYVP (SEQ ID NO: 15);

b) administering the peptide to a mammal under conditions appropriate for the stimulation of an immune response; and c) isolating the polyclonal antibody from the mammal.

2. The method of claim 1 wherein the peptide is produced synthetically.

3. A method for producing a monoclonal antibody which binds specifically to the 43 kDa dystrophin-associated protein, the molecular weight of the protein being determined by electrophoretic separation under denaturing conditions, transfer to a solid support and staining with wheat germ agglutinin, the method comprising:

a) providing the peptide PKNMTPYRSPPPYVP (SEQ ID NO: 15);

b) administering the peptide to a mammal under conditions appropriate for the stimulation of an immune response;

c) isolating antibody producing cells from the mammal;

d) fusing the antibody producing cells with immortalizing cells to produce a hybridoma cell line; and e) screening the resulting hybridoma cell line to identify cell lines secreting antibody having the desired specificity.

4. The method of claim 3 wherein the peptide is produced synthetically.

5. An immunogenic peptide PKNMTPYRSPPPYVP (SEQ ID NO: 15) which, in the immunization of a mammal, stimulates the production of antibodies which bind specifically to the 43 kDa dystrophin-associated protein, the molecular weight of the protein being determined by electrophoretic separation under denaturing conditions, transfer to a solid support and staining with wheat germ agglutinin.

6. The immunogenic peptide of claim 5, which is produced synthetically.

\* \* \* \* \*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 4200 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 170..2855

( x i ) SEQUENCE DESCRIPTION: SEQ ID NO:1:

```
GGCTGCTTTT CAGGAAGATA AAGCTTTTAA GGCTGCCTAA CACTAGAAGG AGAGGCTCTC        60

GATGCTCTGG GATGGAGCAG GTGTGCAGAG GGTGAGGACC CGGCTCTGGG ATCAAGTCAC       120

TTGCTTGCTT CCTTAGCAAG ATCTTCGGCT TGAGCGAACT TGGCCTGGG ATG AGG           175
                                                       Met Arg
                                                        1

ATG TCT GTG GGC CTT TCA CTG CTG CTC CCC TTG TGG GGG AGG ACA TTT         223
Met Ser Val Gly Leu Ser Leu Leu Leu Pro Leu Trp Gly Arg Thr Phe
         5              10                 15

CTC CTC CTC CTC TGT GTG GCC GTG GCT CAG TCC CAT TGG CCC AGC GAA         271
Leu Leu Leu Leu Cys Val Ala Val Ala Gln Ser His Trp Pro Ser Glu
        20                  25                 30

CCC TCG GAG GCT GTC AGG GAC TGG GAG AAC CAG CTG GAG GCG TCC ATG         319
Pro Ser Glu Ala Val Arg Asp Trp Glu Asn Gln Leu Glu Ala Ser Met
 35                 40                  45                  50

CAC TCT GTG CTC TCA GAC CTG CAC GAA GCC CTT CCC ACA GTG GTT GGC         367
His Ser Val Leu Ser Asp Leu His Glu Ala Leu Pro Thr Val Val Gly
                55                  60                  65

ATT CCT GAT GGC ACG GCT GTT GTT GGG CGC TCG TTT CGA GTG ACC ATT         415
Ile Pro Asp Gly Thr Ala Val Val Gly Arg Ser Phe Arg Val Thr Ile
            70                  75                  80

CCA ACA GAT TTA ATT GGC TCC AGT GGA GAA GTC ATC AAG GTA TCC ACG         463
Pro Thr Asp Leu Ile Gly Ser Ser Gly Glu Val Ile Lys Val Ser Thr
        85                  90                  95

GCA GGG AAG GAG GTT TTG CCA TCG TGG CTG CAT TGG GAT CCA CAG AGC         511
Ala Gly Lys Glu Val Leu Pro Ser Trp Leu His Trp Asp Pro Gln Ser
    100                 105                 110

CAC ACC CTG GAG GGC CTT CCG CTG GAC ACG GAC AAG GGT GTG CAT TAC         559
His Thr Leu Glu Gly Leu Pro Leu Asp Thr Asp Lys Gly Val His Tyr
115                 120                 125                 130

ATC TCA GTG AGC GCT GCA CAG CTG GAT GCC AAC GGA AGC CAC ATC CCT         607
Ile Ser Val Ser Ala Ala Gln Leu Asp Ala Asn Gly Ser His Ile Pro
```

|   |   |   |   |   |   |   |   |   |   |   |   |   |   |   |   |      |
|---|---|---|---|---|---|---|---|---|---|---|---|---|---|---|---|------|
|   |   |   | 135 |   |   |   |   | 140 |   |   |   |   | 145 |   |   |      |
| CAG | ACC | TCC | AGT | GTG | TTC | TCC | ATC | GAG | GTC | TAC | CCC | GAA | GAC | CAC | AGT | 655  |
| Gln | Thr | Ser | Ser<br>150 | Val | Phe | Ser | Ile | Glu<br>155 | Val | Tyr | Pro | Glu | Asp<br>160 | His | Ser |      |
| GAG | CCG | CAG | TCT | GTG | CGG | GCG | GCC | TCT | CCA | GAC | CTG | GGC | GAG | GCG | GCG | 703  |
| Glu | Pro | Gln<br>165 | Ser | Val | Arg | Ala | Ala<br>170 | Ser | Pro | Asp | Leu | Gly<br>175 | Glu | Ala | Ala |      |
| GCG | TCT | GCC | TGT | GCT | GCC | GAG | GAG | CCG | GTG | ACC | GTC | TTG | ACC | GTG | ATT | 751  |
| Ala | Ser<br>180 | Ala | Cys | Ala | Ala<br>185 | Glu | Glu | Pro | Val | Thr<br>190 | Val | Leu | Thr | Val | Ile |      |
| CTG | GAT | GCC | GAT | CTC | ACC | AAG | ATG | ACT | CCG | AAG | CAG | AGG | ATC | GAC | CTC | 799  |
| Leu<br>195 | Asp | Ala | Asp | Leu | Thr<br>200 | Lys | Met | Thr | Pro | Lys<br>205 | Gln | Arg | Ile | Asp | Leu<br>210 |      |
| CTG | CAC | AGG | ATG | CAG | AGC | TTC | TCG | GAG | GTG | GAG | CTC | CAC | AAC | ATG | AAG | 847  |
| Leu | His | Arg | Met | Gln<br>215 | Ser | Phe | Ser | Glu | Val<br>220 | Glu | Leu | His | Asn | Met<br>225 | Lys |      |
| TTG | GTG | CCG | GTG | GTG | AAT | AAC | AGA | CTG | TTT | GAT | ATG | TCT | GCC | TTC | ATG | 895  |
| Leu | Val | Pro | Val<br>230 | Val | Asn | Asn | Arg | Leu<br>235 | Phe | Asp | Met | Ser | Ala<br>240 | Phe | Met |      |
| GCC | GGC | CCC | GGA | AAC | GCC | AAA | AAG | GTG | GTA | GAG | AAC | GGG | GCC | CTG | CTC | 943  |
| Ala | Gly | Pro<br>245 | Gly | Asn | Ala | Lys | Lys<br>250 | Val | Val | Glu | Asn | Gly<br>255 | Ala | Leu | Leu |      |
| TCC | TGG | AAG | CTG | GGC | TGC | TCC | CTG | AAC | CAG | AAC | AGT | GTG | CCT | GAC | ATT | 991  |
| Ser | Trp<br>260 | Lys | Leu | Gly | Cys | Ser<br>265 | Leu | Asn | Gln | Asn | Ser<br>270 | Val | Pro | Asp | Ile |      |
| CGC | GGC | GTG | GAG | GCC | CCT | GCC | AGG | GAG | GGC | ACT | ATG | TCT | GCC | CAG | CTT | 1039 |
| Arg<br>275 | Gly | Val | Glu | Ala | Pro<br>280 | Ala | Arg | Glu | Gly | Thr<br>285 | Met | Ser | Ala | Gln | Leu<br>290 |      |
| GGC | TAC | CCT | GTG | GTG | GGT | TGG | CAC | ATT | GCC | AAC | AAG | AAG | CCA | CCT | CTC | 1087 |
| Gly | Tyr | Pro | Val | Val<br>295 | Gly | Trp | His | Ile | Ala<br>300 | Asn | Lys | Lys | Pro | Pro<br>305 | Leu |      |
| CCC | AAG | CGT | ATC | CGA | AGG | CAG | ATC | CAT | GCC | ACA | CCC | ACA | CCT | GTC | ACT | 1135 |
| Pro | Lys | Arg | Ile<br>310 | Arg | Arg | Gln | Ile | His<br>315 | Ala | Thr | Pro | Thr | Pro<br>320 | Val | Thr |      |
| GCC | ATT | GGG | CCC | CCA | ACC | ACG | GCC | ATC | CAG | GAG | CCG | CCG | TCC | AGG | ATC | 1183 |
| Ala | Ile | Gly<br>325 | Pro | Pro | Thr | Thr | Ala<br>330 | Ile | Gln | Glu | Pro | Pro<br>335 | Ser | Arg | Ile |      |
| GTG | CCT | ACC | CCC | ACT | TCT | CCA | GCC | ATT | GCT | CCT | CCC | ACA | GAG | ACG | ATG | 1231 |
| Val | Pro | Thr<br>340 | Pro | Thr | Ser | Pro<br>345 | Ala | Ile | Ala | Pro | Pro<br>350 | Thr | Glu | Thr | Met |      |
| GCT | CCT | CCA | GTC | AGG | GAT | CCT | GTT | CCT | GGG | AAG | CCC | ACG | GTC | ACC | ACT | 1279 |
| Ala | Pro<br>355 | Pro | Val | Arg | Asp | Pro<br>360 | Val | Pro | Gly | Lys | Pro<br>365 | Thr | Val | Thr | Thr<br>370 |      |
| CGG | ACT | CGA | GGT | GCC | ATT | ATT | CAG | ACC | CCA | ACC | CTA | GGC | CCC | ATC | CAG | 1327 |
| Arg | Thr | Arg | Gly | Ala<br>375 | Ile | Ile | Gln | Thr | Pro<br>380 | Thr | Leu | Gly | Pro | Ile<br>385 | Gln |      |
| CCC | ACT | CGG | GTG | TCA | GAC | GCT | GGC | ACC | GTA | GTT | TCT | GGC | CAG | ATT | CGT | 1375 |
| Pro | Thr | Arg | Val<br>390 | Ser | Asp | Ala | Gly | Thr<br>395 | Val | Val | Ser | Gly | Gln<br>400 | Ile | Arg |      |
| GCA | ACG | GTG | ACC | ATT | CCT | GGC | TAC | GTG | GAG | CCC | ACA | GCA | GTT | GCC | ACC | 1423 |
| Ala | Thr | Val<br>405 | Thr | Ile | Pro | Gly | Tyr<br>410 | Val | Glu | Pro | Thr | Ala<br>415 | Val | Ala | Thr |      |
| CCT | CCC | ACA | ACT | ACA | ACC | AAA | AAG | CCA | CGA | GTG | TCC | ACA | CCA | AAA | CCA | 1471 |
| Pro | Pro | Thr<br>420 | Thr | Thr | Thr | Thr<br>425 | Lys | Lys | Pro | Arg | Val<br>430 | Ser | Thr | Pro | Lys | Pro |      |
| GCA | ACG | CCT | TCA | ACG | GAC | TCC | TCA | GCC | ACC | ACG | ACT | CGC | AGG | CCA | ACC | 1519 |
| Ala | Thr<br>435 | Pro | Ser | Thr | Asp<br>440 | Ser | Ser | Ala | Thr | Thr<br>445 | Thr | Arg | Arg | Pro | Thr<br>450 |      |
| AAG | AAG | CCA | CGG | ACA | CCC | AGG | CCG | GTG | CCA | CGG | GTC | ACC | ACT | AAA | GCT | 1567 |
| Lys | Lys | Pro | Arg | Thr | Pro | Arg | Pro | Val | Pro | Arg | Val | Thr | Thr | Lys | Ala |      |

|     |     |     |     |     |     |     | 455 |     |     |     |     | 460 |     |     |     |     | 465 |     |     |      |
|-----|-----|-----|-----|-----|-----|-----|-----|-----|-----|-----|-----|-----|-----|-----|-----|-----|-----|-----|-----|------|

```
CCC  ATC  ACC  AGG  CTG  GAG  ACG  GCC  TCC  CCA  CCT  ACT  CGT  ATC  CGC  ACC       1615
Pro  Ile  Thr  Arg  Leu  Glu  Thr  Ala  Ser  Pro  Pro  Thr  Arg  Ile  Arg  Thr
               470                      475                      480

ACC  ACC  AGC  GGG  GTG  CCC  CGC  GGG  GGA  GAA  CCC  AAC  CAG  CGC  CCA  GAG       1663
Thr  Thr  Ser  Gly  Val  Pro  Arg  Gly  Gly  Glu  Pro  Asn  Gln  Arg  Pro  Glu
               485                      490                      495

CTC  AAG  AAC  CAC  ATC  GAC  AGG  GTG  GAC  GCC  TGG  GTC  GGC  ACC  TAC  TTT       1711
Leu  Lys  Asn  His  Ile  Asp  Arg  Val  Asp  Ala  Trp  Val  Gly  Thr  Tyr  Phe
               500                      505                      510

GAG  GTG  AAG  ATC  CCA  TCT  GAT  ACC  TTC  TAC  GAC  AAG  GAG  GAT  ACC  ACC       1759
Glu  Val  Lys  Ile  Pro  Ser  Asp  Thr  Phe  Tyr  Asp  Lys  Glu  Asp  Thr  Thr
515                 520                      525                      530

ACC  GAC  AAG  CTC  AAG  CTG  ACC  CTG  AAG  CTG  CGA  GAG  CAG  CAG  CTG  GTG       1807
Thr  Asp  Lys  Leu  Lys  Leu  Thr  Leu  Lys  Leu  Arg  Glu  Gln  Gln  Leu  Val
               535                      540                      545

GGC  GAG  AAG  TCC  TGG  GTG  CAG  TTC  AAC  AGC  AAC  AGC  CAG  CTC  ATG  TAT       1855
Gly  Glu  Lys  Ser  Trp  Val  Gln  Phe  Asn  Ser  Asn  Ser  Gln  Leu  Met  Tyr
               550                      555                      560

GGC  CTG  CCC  GAC  AGC  AGC  CAC  GTG  GGC  AAA  CAC  GAG  TAT  TTC  ATG  CAT       1903
Gly  Leu  Pro  Asp  Ser  Ser  His  Val  Gly  Lys  His  Glu  Tyr  Phe  Met  His
               565                      570                      575

GCC  ACA  GAC  AAG  GGA  GGC  CTG  TCC  GCC  GTG  GAT  GCC  TTT  GAG  ATC  CAT       1951
Ala  Thr  Asp  Lys  Gly  Gly  Leu  Ser  Ala  Val  Asp  Ala  Phe  Glu  Ile  His
               580                      585                      590

GTC  CAC  AAG  CGC  CCT  CAA  GGG  GAC  AAA  GCT  CCT  GCT  CGT  TTC  AAA  GCC       1999
Val  His  Lys  Arg  Pro  Gln  Gly  Asp  Lys  Ala  Pro  Ala  Arg  Phe  Lys  Ala
595                 600                      605                      610

AAG  TTC  GTG  GGT  GAC  CCA  GCG  CCA  GTG  GTG  AAT  GAC  ATC  CAC  AAG  AAG       2047
Lys  Phe  Val  Gly  Asp  Pro  Ala  Pro  Val  Val  Asn  Asp  Ile  His  Lys  Lys
               615                      620                      625

ATT  GCC  CTG  GTG  AAG  AAG  CTG  GCC  TTT  GCC  TTT  GGG  GAT  CGC  AAT  TGC       2095
Ile  Ala  Leu  Val  Lys  Lys  Leu  Ala  Phe  Ala  Phe  Gly  Asp  Arg  Asn  Cys
               630                      635                      640

AGC  ACC  GTC  ACC  CTG  CAG  AAC  ATC  ACC  CGC  GGC  TCC  ATT  GTG  GTG  GAG       2143
Ser  Thr  Val  Thr  Leu  Gln  Asn  Ile  Thr  Arg  Gly  Ser  Ile  Val  Val  Glu
               645                      650                      655

TGG  ACC  AAC  AAC  ACA  CTG  CCG  CTG  GAG  CCC  TGC  CCC  AAG  GAG  CAG  ATC       2191
Trp  Thr  Asn  Asn  Thr  Leu  Pro  Leu  Glu  Pro  Cys  Pro  Lys  Glu  Gln  Ile
660                 665                      670

ACG  GGG  CTG  AGC  CGC  AGG  ATC  GCC  GAG  GAC  AAC  GGG  CAG  CCT  CGG  CCA       2239
Thr  Gly  Leu  Ser  Arg  Arg  Ile  Ala  Glu  Asp  Asn  Gly  Gln  Pro  Arg  Pro
675                 680                      685                      690

GCC  TTC  ACC  AAT  GCC  CTG  GAG  CCT  GAC  TTT  AAG  GCC  ACG  AGC  ATC  GCC       2287
Ala  Phe  Thr  Asn  Ala  Leu  Glu  Pro  Asp  Phe  Lys  Ala  Thr  Ser  Ile  Ala
                         695                      700                      705

ATA  ACG  GGC  TCT  GGC  AGT  TGT  CGG  CAC  TTG  CAG  TTT  ATC  CCC  GTG  GCA       2335
Ile  Thr  Gly  Ser  Gly  Ser  Cys  Arg  His  Leu  Gln  Phe  Ile  Pro  Val  Ala
               710                      715                      720

CCG  CCT  GGG  ATC  CCG  TCC  TCG  GTG  ACA  CCA  CCC  ACG  GAG  GTG  CCA  GAC       2383
Pro  Pro  Gly  Ile  Pro  Ser  Ser  Val  Thr  Pro  Pro  Thr  Glu  Val  Pro  Asp
               725                      730                      735

AGG  GAC  CCC  GAG  AAG  AGC  AGT  GAG  GAT  GAC  GTC  TAC  CTA  CAC  ACA  GTC       2431
Arg  Asp  Pro  Glu  Lys  Ser  Ser  Glu  Asp  Asp  Val  Tyr  Leu  His  Thr  Val
740                 745                      750

ATT  CCG  GCT  GTG  GTG  GTG  GCG  GCC  ATC  CTG  CTC  ATT  GCT  GGC  ATC  ATT       2479
Ile  Pro  Ala  Val  Val  Val  Ala  Ala  Ile  Leu  Leu  Ile  Ala  Gly  Ile  Ile
755                 760                      765                      770

GCC  ATG  ATC  TGC  TAC  CGC  AAG  AAG  CGG  AAG  GGC  AAG  CTC  ACC  CTG  GAG       2527
Ala  Met  Ile  Cys  Tyr  Arg  Lys  Lys  Arg  Lys  Gly  Lys  Leu  Thr  Leu  Glu
```

-continued

```
                    775                         780                         785
     GAC CAG GCC ACC TTC ATC AAG AAG GGG GTG CCC ATC ATC TTT GCA GAC              2575
     Asp Gln Ala Thr Phe Ile Lys Lys Gly Val Pro Ile Ile Phe Ala Asp
                 790                         795                     800

GAG CTG GAC GAC TCC AAG CCC CCG CCC TCC TCC AGC ATG CCG CTG ATC              2623
     Glu Leu Asp Asp Ser Lys Pro Pro Pro Ser Ser Ser Met Pro Leu Ile
                     805                         810                 815

CTG CAG GAG GAG AAG GCT CCC CTT CCC CCC CCA GAG TAT CCC AGC CAG              2671
     Leu Gln Glu Glu Lys Ala Pro Leu Pro Pro Pro Glu Tyr Pro Ser Gln
             820                         825                     830

AGC GTG CCC GAG ACC ACG CCT CTG AAC CAG GAC ACT GTG GGG GAG TAC              2719
     Ser Val Pro Glu Thr Thr Pro Leu Asn Gln Asp Thr Val Gly Glu Tyr
     835                         840                     845                 850

ACG CCC CTT CGG GAT GAG GAT CCC AAC GCG CCT CCC TAC CAG CCC CCC              2767
     Thr Pro Leu Arg Asp Glu Asp Pro Asn Ala Pro Pro Tyr Gln Pro Pro
                         855                     860                     865

CCA CCC TTC ACA GCC CCG ATG GAG GGC AAG GGC TCC CGT CCC AAG AAC              2815
     Pro Pro Phe Thr Ala Pro Met Glu Gly Lys Gly Ser Arg Pro Lys Asn
                 870                     875                     880

ATG ACC CCT TAC CGG TCA CCC CCT CCT TAT GTT CCC CCT T AACCCACAAG             2865
     Met Thr Pro Tyr Arg Ser Pro Pro Pro Tyr Val Pro Pro
                 885                     890                 895

CGCCTGGGTG GAGGCAGGGT AGGGCAGGGG CCTGGGGACA ACACAGTGTT GTCTGTGGAG            2925
     CCCGGTGGCC CGCAGACCAT CGCCCACTGG GCGCTGACAC CAGACCTAGC ACACACTGGC            2985
     ACACGGGGCC TGGACAAGCC CGCCCTCTCT GGTCCTCCCA AACCCCAAAG CAGCTGGAGA            3045
     GACTTGGGG  ACTTTTTTA  TTTTTATTTT TTGCCTAACA GCTTTTGTT  TGTTCATAGA            3105
     AAATCCTTCG CTGCGTTTTG ATGGCTGGCT CTGGAAGCAC CATTTGGAGT AGAGGTAGAG            3165
     GGAGGGAGCG AGGAGCCGTG GGTGAACTCG CAGGCAGTGC TGGGCAGCCC CCCGGCTCTC            3225
     TGCGTTTTGC CTTTAACACT AACTGTACTG TTTTTTCTAT TCACGTGTGT CTAGCTGCAG            3285
     GATGTAACAT GGAAAACAGT AGCTAAAGAT TAAATTCAAA GGACTTTCAG AAGTTAAGGT            3345
     TAAGTTTTTA CATTTAATCT GCTGTTTACC TAAACTTGTA TGTATAATTT TTGGGTGGGT            3405
     ATGGGAATT  GCTTTGCTAA AAATAAGCTC CCAGGGTGTT TCAAACTTAA GAGAAGACCA            3465
     AGGGACAGTA TTTTTTATCA AAGGAATCCT ATTTTTCAC  ACTATGTCAA CTTGGTTGCT            3525
     CTGATATCCC AGAGCCCGAT CGGGGGCCTC CTGGCCCTGG CTCAGGGGCC AGGGTCCTGG            3585
     TGCTGGGTTT GCTCTCCTGC TGTTGGCAGG AGTTGGAAGC TGGAGGGGCC TCTCGGGCCG            3645
     TGGACATCCC CACCTCCACC CCATGCATGC TAGTGGCCCA CCACCAAGGG GTCTTCATTT            3705
     CCATGGGAAA GGGACTCCAA GAGGCAGTGG TGGCCGTGGC CCCCACCCCG GGTGCTCCAA            3765
     GGTGGGCCAG CTGCTCGTGG GGGCCCCTGG GGAGGTTGAG GGACTCGACC ACATCGACCT            3825
     GTTTCCTTTC ACCTTTTATT TTTTTTTTC  CCCACCCCTC CTAAAAGGAT TATCACGGTT            3885
     TTTGAAACAC TCAGTGGGGG ACATTTGGT  GAAGATGCAA  TATTTTTATG TCATGTGATG           3945
     CTCTTTCCTC ACTTGACCTT GGCCACTTTG TCCCAACAGT CCACAGCCCC GCCCCGATCC            4005
     ACCCCATCCC TCTTCTCTGG CGCTCCCGTC CCAGGCCTTG GGCCTGAACG ACTGGAAAAG            4065
     GCCTGGTTGG CTGGGAGGA  GTGCCACCAA TAGTTCATAG TAAACAATCT GTGGGCTCTC            4125
     AAAGCTAATT TTTACTAAA  GTTTTTATAC AGCCTCAAAT TGTTTTATTA AAAAATAGAT            4185
     TAAAAATGGT GATGC                                                            4200
```

( 2 ) INFORMATION FOR SEQ ID NO:2:

( i ) SEQUENCE CHARACTERISTICS:

( A ) LENGTH: 10
( B ) TYPE: amino acid
( D ) TOPOLOGY: linear ( i i ) MOLECULE TYPE: Peptide ( x i ) SEQUENCE DESCRIPTION: SEQ ID NO:2:

Pro Arg Pro Leu Ser Thr Leu Pro Met Phe    10

( 2 ) INFORMATION FOR SEQ ID NO:3:

( i ) SEQUENCE CHARACTERISTICS:
( A ) LENGTH: 9
( B ) TYPE: amino acid
( D ) TOPOLOGY: linear ( i i ) MOLECULE TYPE: Peptide ( x i ) SEQUENCE DESCRIPTION: SEQ ID NO:3:

His Asp Val Glu Glu Val Leu Pro Pro ( 2 ) INFORMATION FOR SEQ ID NO:4:

( i ) SEQUENCE CHARACTERISTICS:
( A ) LENGTH: 14
( B ) TYPE: amino acid
( D ) TOPOLOGY: linear ( i i ) MOLECULE TYPE: Peptide ( x i ) SEQUENCE DESCRIPTION: SEQ ID NO:4:

Glu Val Pro Arg Pro Leu Ser Thr Leu Pro Met Phe Asn Val ( 2 ) INFORMATION FOR SEQ ID NO:5:

( i ) SEQUENCE CHARACTERISTICS:
( A ) LENGTH: 7
( B ) TYPE: amino acid
( D ) TOPOLOGY: linear ( i i ) MOLECULE TYPE: Peptide ( x i ) SEQUENCE DESCRIPTION: SEQ ID NO:5:

Phe Val His Thr Leu Glu Pro ( 2 ) INFORMATION FOR SEQ ID NO:6:

( i ) SEQUENCE CHARACTERISTICS:
( A ) LENGTH: 9
( B ) TYPE: amino acid
( D ) TOPOLOGY: linear ( i i ) MOLECULE TYPE: Peptide ( x i ) SEQUENCE DESCRIPTION: SEQ ID NO:6:

Leu Ala Thr Ser Xaa Ile Gln Met Val ( 2 ) INFORMATION FOR SEQ ID NO:7:

( i ) SEQUENCE CHARACTERISTICS:
( A ) LENGTH: 5510 base pairs
( B ) TYPE: nucleic acid
( C ) STRANDEDNESS: double
( D ) TOPOLOGY: linear ( i i ) MOLECULE TYPE: cDNA ( i v ) ANTI-SENSE: NO ( i x ) FEATURE:

(A) NAME/KEY: CDS
(B) LOCATION: 395..3079

(xi) SEQUENCE DESCRIPTION: SEQ ID NO:7:

```
GGGCCAGTCG GCGCCGCGCG GAGCTGGCCG CTGGATTGGC TGCAACACTC GCGTGTCAGG      60

CGGTTGCTAG GCTCCGGCCG CGCGCCCCGC CCTTGCGCTC AGCGCCCTCT CACCGCCCGG     120

TACGTGCTCG CGCGAAGGCT GCGGCGCGGC GCTCGCGCCT CTTAGGCTTG GCGGTGGCGG     180

CGGCGGCAGC TTCGCGCCGA ATCCCCGGGG AGCGGCGGTG GCGGCGTCCT GGGGCCAGGA     240

GGAGCGAACA CCTGCCGCGG TCCTCCCGCC GGCGCTGGGC TCTGTGTGCT CCGGGATGGA     300

GCAGGTGTGC AGAGGGTGAG AACCCAGCTC TGGGACCAAG TCACTTGCTT CCTTACTTAG     360

CAAGACTATC GACTTGAGCA AACTTGGACC TGG ATG AGG ATG TCT GTG GGC           412
                                     Met Arg Met Ser Val Gly
                                      1               5
```

| | | | | | | | | | | | | | | | | |
|---|---|---|---|---|---|---|---|---|---|---|---|---|---|---|---|---|
| CTC | TCG | CTG | CTG | CTG | CCC | CTC | TGG | GGG | AGG | ACC | TTT | CTC | CTC | CTG | CTC | 460 |
| Leu | Ser | Leu | Leu | Leu | Pro | Leu | Trp | Gly | Arg | Thr | Phe | Leu | Leu | Leu | Leu | |
| | | 10 | | | | | 15 | | | | | 20 | | | | |

```
TCT GTG GTT ATG GCT CAG TCC CAC TGG CCC AGT GAA CCC TCA GAG GCT        508
Ser Val Val Met Ala Gln Ser His Trp Pro Ser Glu Pro Ser Glu Ala
         25                   30                  35

GTC AGG GAC TGG GAA AAC CAG CTT GAG GCA TCC ATG CAC TCA GTG CTC        556
Val Arg Asp Trp Glu Asn Gln Leu Glu Ala Ser Met His Ser Val Leu
     40                  45                  50

TCA GAC CTC CAC GAG GCT GTT CCC ACA GTG GTT GGC ATT CCT GAT GGC        604
Ser Asp Leu His Glu Ala Val Pro Thr Val Val Gly Ile Pro Asp Gly
 55                  60                  65                  70

ACG GCT GTC GTC GGG CGC TCA TTT CGA GTG ACC ATT CCA ACA GAT TTG        652
Thr Ala Val Val Gly Arg Ser Phe Arg Val Thr Ile Pro Thr Asp Leu
                 75                  80                  85

ATT GCC TCC AGT GGA GAT ATC ATC AAG GTA TCA GCG GCA GGG AAG GAG        700
Ile Ala Ser Ser Gly Asp Ile Ile Lys Val Ser Ala Ala Gly Lys Glu
                 90                  95                 100

GCT TTG CCA TCT TGG CTG CAC TGG GAC TCA CAG AGC CAC ACC CTG GAG        748
Ala Leu Pro Ser Trp Leu His Trp Asp Ser Gln Ser His Thr Leu Glu
            105                 110                 115

GGC CTC CCC CTT GAC ACT GAT AAG GGT GTG CAT TAC ATT TCA GTG AGC        796
Gly Leu Pro Leu Asp Thr Asp Lys Gly Val His Tyr Ile Ser Val Ser
        120                 125                 130

GCT ACA CGG CTG GGG GCC AAC GGG AGC CAC ATC CCC CAG ACC TCC AGT        844
Ala Thr Arg Leu Gly Ala Asn Gly Ser His Ile Pro Gln Thr Ser Ser
135                 140                 145                 150

GTG TTC TCC ATC GAG GTC TAC CCT GAA GAC CAC AGT GAT CTG CAG TCG        892
Val Phe Ser Ile Glu Val Tyr Pro Glu Asp His Ser Asp Leu Gln Ser
                155                 160                 165

GTG AGG ACA GCC TCC CCA GAC CCT GGT GAG GTG GTA TCA TCT GCC TGT        940
Val Arg Thr Ala Ser Pro Asp Pro Gly Glu Val Val Ser Ser Ala Cys
            170                 175                 180

GCT GCG GAT GAA CCT GTG ACT GTT TTG ACG GTG ATT TTG GAT GCC GAC        988
Ala Ala Asp Glu Pro Val Thr Val Leu Thr Val Ile Leu Asp Ala Asp
        185                 190                 195

CTC ACC AAG ATG ACC CCA AAG CAA AGG ATT GAC CTC CTG CAC AGG ATG       1036
Leu Thr Lys Met Thr Pro Lys Gln Arg Ile Asp Leu Leu His Arg Met
200                 205                 210

CGG AGC TTC TCA GAA GTA GAG CTT CAC AAC ATG AAA TTA GTG CCG GTG       1084
Arg Ser Phe Ser Glu Val Glu Leu His Asn Met Lys Leu Val Pro Val
215                 220                 225                 230

GTG AAT AAC AGA CTA TTT GAC ATG TCG GCC TTC ATG GCT GGC CCG GGA       1132
Val Asn Asn Arg Leu Phe Asp Met Ser Ala Phe Met Ala Gly Pro Gly
                235                 240                 245
```

| | | | | | | | | | | | | | | | | |
|---|---|---|---|---|---|---|---|---|---|---|---|---|---|---|---|---|
| AAT | CCA | AAA | AAG | GTG | GTG | GAG | AAT | GGG | GCC | CTT | CTC | TCC | TGG | AAG | CTG | 1180 |
| Asn | Pro | Lys | Lys | Val | Val | Glu | Asn | Gly | Ala | Leu | Leu | Ser | Trp | Lys | Leu | |
| | | 250 | | | | | 255 | | | | | 260 | | | | |
| GGC | TGC | TCC | CTG | AAC | CAG | AAC | AGT | GTG | CCT | GAC | ATT | CAT | GGT | GTA | GAG | 1228 |
| Gly | Cys | Ser | Leu | Asn | Gln | Asn | Ser | Val | Pro | Asp | Ile | His | Gly | Val | Glu | |
| | | 265 | | | | 270 | | | | | 275 | | | | | |
| GCC | CCT | GCC | AGG | GAG | GGC | GCA | ATG | TCT | GCT | CAG | CTT | GGC | TAC | CCT | GTG | 1276 |
| Ala | Pro | Ala | Arg | Glu | Gly | Ala | Met | Ser | Ala | Gln | Leu | Gly | Tyr | Pro | Val | |
| | 280 | | | | | 285 | | | | | 290 | | | | | |
| GTG | GGT | TGG | CAC | ATC | GCC | AAT | AAG | AAG | CCC | CCT | CTT | CCC | AAA | CGC | GTC | 1324 |
| Val | Gly | Trp | His | Ile | Ala | Asn | Lys | Lys | Pro | Pro | Leu | Pro | Lys | Arg | Val | |
| 295 | | | | | 300 | | | | | 305 | | | | | 310 | |
| CGG | AGG | CAG | ATC | CAT | GCT | ACA | CCC | ACA | CCT | GTC | ACT | GCC | ATT | GGG | CCC | 1372 |
| Arg | Arg | Gln | Ile | His | Ala | Thr | Pro | Thr | Pro | Val | Thr | Ala | Ile | Gly | Pro | |
| | | | | 315 | | | | | 320 | | | | | 325 | | |
| CCA | ACC | ACG | GCT | ATC | CAG | GAG | CCC | CCA | TCC | AGG | ATC | GTG | CCA | ACC | CCC | 1420 |
| Pro | Thr | Thr | Ala | Ile | Gln | Glu | Pro | Pro | Ser | Arg | Ile | Val | Pro | Thr | Pro | |
| | | | 330 | | | | | 335 | | | | | 340 | | | |
| ACA | TCT | CCA | GCC | ATT | GCT | CCT | CCA | ACA | GAG | ACC | ATG | GCT | CCT | CCA | GTC | 1468 |
| Thr | Ser | Pro | Ala | Ile | Ala | Pro | Pro | Thr | Glu | Thr | Met | Ala | Pro | Pro | Val | |
| | | 345 | | | | | 350 | | | | | 355 | | | | |
| AGG | GAT | CCT | GTT | CCT | GGG | AAA | CCC | ACG | GTC | ACC | ATC | CGG | ACT | CGA | GGC | 1516 |
| Arg | Asp | Pro | Val | Pro | Gly | Lys | Pro | Thr | Val | Thr | Ile | Arg | Thr | Arg | Gly | |
| | 360 | | | | | 365 | | | | | 370 | | | | | |
| GCC | ATT | ATT | CAA | ACC | CCA | ACC | CTA | GGC | CCC | ATC | CAG | CCT | ACT | CGG | GTG | 1564 |
| Ala | Ile | Ile | Gln | Thr | Pro | Thr | Leu | Gly | Pro | Ile | Gln | Pro | Thr | Arg | Val | |
| 375 | | | | | 380 | | | | | 385 | | | | | 390 | |
| TCA | GAA | GCT | GGC | ACC | ACA | GTT | CCT | GGC | CAG | ATT | CGC | CCA | ACG | ATG | ACC | 1612 |
| Ser | Glu | Ala | Gly | Thr | Thr | Val | Pro | Gly | Gln | Ile | Arg | Pro | Thr | Met | Thr | |
| | | | | 395 | | | | | 400 | | | | | 405 | | |
| ATT | CCT | GGC | TAT | GTG | GAG | CCT | ACT | GCA | GTT | GCT | ACC | CCT | CCC | ACA | ACC | 1660 |
| Ile | Pro | Gly | Tyr | Val | Glu | Pro | Thr | Ala | Val | Ala | Thr | Pro | Pro | Thr | Thr | |
| | | | 410 | | | | | 415 | | | | | 420 | | | |
| ACC | ACC | AAG | AAG | CCA | CGA | GTA | TCC | ACA | CCA | AAA | CCA | GCA | ACG | CCT | TCA | 1708 |
| Thr | Thr | Lys | Lys | Pro | Arg | Val | Ser | Thr | Pro | Lys | Pro | Ala | Thr | Pro | Ser | |
| | | 425 | | | | | 430 | | | | | 435 | | | | |
| ACT | GAC | TCC | ACC | ACC | ACC | ACG | ACT | CGC | AGG | CCA | ACC | AAG | AAA | CCA | CGG | 1756 |
| Thr | Asp | Ser | Thr | Thr | Thr | Thr | Thr | Arg | Arg | Pro | Thr | Lys | Lys | Pro | Arg | |
| | 440 | | | | | 445 | | | | | 450 | | | | | |
| ACA | CCC | CGG | CCA | GTG | CCC | CGG | GTC | ACC | ACC | AAA | GTT | TCC | ATC | ACC | AGA | 1804 |
| Thr | Pro | Arg | Pro | Val | Pro | Arg | Val | Thr | Thr | Lys | Val | Ser | Ile | Thr | Arg | |
| 455 | | | | 460 | | | | | 465 | | | | | 470 | | |
| TTG | GAA | ACT | GCC | TCA | CCG | CCT | ACT | CGT | ATT | CGC | ACC | ACC | ACC | AGT | GGA | 1852 |
| Leu | Glu | Thr | Ala | Ser | Pro | Pro | Thr | Arg | Ile | Arg | Thr | Thr | Thr | Ser | Gly | |
| | | | | 475 | | | | | 480 | | | | | 485 | | |
| GTG | CCC | CGT | GGC | GGA | GAA | CCC | AAC | CAG | CGC | CCA | GAG | CTC | AAG | AAC | CAT | 1900 |
| Val | Pro | Arg | Gly | Gly | Glu | Pro | Asn | Gln | Arg | Pro | Glu | Leu | Lys | Asn | His | |
| | | | 490 | | | | | 495 | | | | | 500 | | | |
| ATT | GAC | AGG | GTA | GAT | GCC | TGG | GTT | GGC | ACC | TAC | TTT | GAG | GTG | AAG | ATC | 1948 |
| Ile | Asp | Arg | Val | Asp | Ala | Trp | Val | Gly | Thr | Tyr | Phe | Glu | Val | Lys | Ile | |
| | | 505 | | | | | 510 | | | | | 515 | | | | |
| CCG | TCA | GAC | ACT | TTC | TAT | GAC | CAT | GAG | GAC | ACC | ACC | ACT | GAC | AAG | CTG | 1996 |
| Pro | Ser | Asp | Thr | Phe | Tyr | Asp | His | Glu | Asp | Thr | Thr | Thr | Asp | Lys | Leu | |
| | 520 | | | | | 525 | | | | | 530 | | | | | |
| AAG | CTG | ACC | CTG | AAA | CTG | CGG | GAG | CAG | CAG | CTG | GTG | GGC | GAG | AAG | TCC | 2044 |
| Lys | Leu | Thr | Leu | Lys | Leu | Arg | Glu | Gln | Gln | Leu | Val | Gly | Glu | Lys | Ser | |
| 535 | | | | | 540 | | | | | 545 | | | | | 550 | |
| TGG | GTA | CAG | TTC | AAC | AGC | AAC | AGC | CAG | CTC | ATG | TAT | GGC | CTT | CCC | GAC | 2092 |
| Trp | Val | Gln | Phe | Asn | Ser | Asn | Ser | Gln | Leu | Met | Tyr | Gly | Leu | Pro | Asp | |
| | | | | 555 | | | | | 560 | | | | | 565 | | |

```
AGC AGC CAC GTG GGC AAA CAC GAG TAT TTC ATG CAT GCC ACA GAC AAG    2140
Ser Ser His Val Gly Lys His Glu Tyr Phe Met His Ala Thr Asp Lys
            570                 575                 580

GGG GGC CTG TCG GCT GTG GAT GCC TTC GAG ATC CAC GTC CAC AGG CGC    2188
Gly Gly Leu Ser Ala Val Asp Ala Phe Glu Ile His Val His Arg Arg
            585                 590                 595

CCC CAA GGG GAT AGG GCT CCT GCA AGG TTC AAG GCC AAG TTT GTG GGT    2236
Pro Gln Gly Asp Arg Ala Pro Ala Arg Phe Lys Ala Lys Phe Val Gly
600                 605                 610

GAC CCG GCA CTG GTG TTG AAT GAC ATC CAC AAG AAG ATT GCC TTG GTA    2284
Asp Pro Ala Leu Val Leu Asn Asp Ile His Lys Lys Ile Ala Leu Val
615                 620                 625                 630

AAG AAA CTG GCC TTC GCC TTT GGA GAC CGA AAC TGT AGC ACC ATC ACC    2332
Lys Lys Leu Ala Phe Ala Phe Gly Asp Arg Asn Cys Ser Thr Ile Thr
                635                 640                 645

CTG CAG AAT ATC ACC CGG GGC TCC ATC GTG GTG GAA TGG ACC AAC AAC    2380
Leu Gln Asn Ile Thr Arg Gly Ser Ile Val Val Glu Trp Thr Asn Asn
            650                 655                 660

ACA CTG CCC TTG GAG CCC TGC CCC AAG GAG CAG ATC GCT GGG CTG AGC    2428
Thr Leu Pro Leu Glu Pro Cys Pro Lys Glu Gln Ile Ala Gly Leu Ser
            665                 670                 675

CGC CGG ATC GCT GAG GAT GAT GGA AAA CCT CGG CCT GCC TTC TCC AAC    2476
Arg Arg Ile Ala Glu Asp Asp Gly Lys Pro Arg Pro Ala Phe Ser Asn
680                 685                 690

GCC CTA GAG CCT GAC TTT AAG GCC ACA AGC ATC ACT GTG ACG GGC TCT    2524
Ala Leu Glu Pro Asp Phe Lys Ala Thr Ser Ile Thr Val Thr Gly Ser
695                 700                 705                 710

GGC AGT TGT CGG CAC CTA CAG TTT ATC CCT GTG GTA CCA CCC AGG AGA    2572
Gly Ser Cys Arg His Leu Gln Phe Ile Pro Val Val Pro Pro Arg Arg
                715                 720                 725

GTG CCC TCA GAG GCG CCG CCC ACA GAA GTG CCT GAC AGG GAC CCT GAG    2620
Val Pro Ser Glu Ala Pro Pro Thr Glu Val Pro Asp Arg Asp Pro Glu
            730                 735                 740

AAG AGC AGT GAG GAT GAT GTC TAC CTG CAC ACA GTC ATT CCG GCC GTG    2668
Lys Ser Ser Glu Asp Asp Val Tyr Leu His Thr Val Ile Pro Ala Val
            745                 750                 755

GTG GTC GCA GCC ATC CTG CTC ATT GCT GGC ATC ATT GCC ATG ATC TGC    2716
Val Val Ala Ala Ile Leu Leu Ile Ala Gly Ile Ile Ala Met Ile Cys
760                 765                 770

TAC CGC AAG AAG CGG AAG GGC AAG CTT ACC CTT GAG GAC CAG GCC ACC    2764
Tyr Arg Lys Lys Arg Lys Gly Lys Leu Thr Leu Glu Asp Gln Ala Thr
775                 780                 785                 790

TTC ATC AAG AAG GGG GTG CCT ATC ATC TTT GCA GAC GAA CTG GAC GAC    2812
Phe Ile Lys Lys Gly Val Pro Ile Ile Phe Ala Asp Glu Leu Asp Asp
                795                 800                 805

TCC AAG CCC CCA CCC TCC TCC AGC ATG CCA CTC ATT CTG CAG GAG GAG    2860
Ser Lys Pro Pro Pro Ser Ser Ser Met Pro Leu Ile Leu Gln Glu Glu
            810                 815                 820

AAG GCT CCC CTA CCC CCT CCT GAG TAC CCC AAC CAG AGT GTG CCC GAG    2908
Lys Ala Pro Leu Pro Pro Pro Glu Tyr Pro Asn Gln Ser Val Pro Glu
            825                 830                 835

ACC ACT CCT CTG AAC CAG GAC ACC ATG GGA GAG TAC ACG CCC CTG CGG    2956
Thr Thr Pro Leu Asn Gln Asp Thr Met Gly Glu Tyr Thr Pro Leu Arg
840                 845                 850

GAT GAG GAT CCC AAT GCG CCT CCC TAC CAG CCC CCA CCG CCC TTC ACA    3004
Asp Glu Asp Pro Asn Ala Pro Pro Tyr Gln Pro Pro Pro Pro Phe Thr
855                 860                 865                 870

GTA CCC ATG GAG GGC AAG GGC TCC CGT CCC AAG AAC ATG ACC CCA TAC    3052
Val Pro Met Glu Gly Lys Gly Ser Arg Pro Lys Asn Met Thr Pro Tyr
                875                 880                 885
```

```
CGG TCA CCT CCT CCC TAT GTC CCA CCT TAACCCGCAA GCGCCTGGGT        3099
Arg Ser Pro Pro Pro Tyr Val Pro Pro
            890             895

GGAGGCAGGG TAGGGCAGGG CCCTGGAGAC GACATGGTGT TGTCTGTGGA GACCGGTGGC 3159
CTGCAGACCA TTGCCCACCG GGAGCCGACA CCTGACCTAG CACACACTGA CACAGGGGCC 3219
TGGACAAGCC CGCCCTCTCT GGTCCTCCCA AACCCCAAAG CAGCTGGAGA GACTTTGGGG 3279
ACTTTTTTAT TTTTATTTTT TGCCTAACAG CTTTGGTTT GTTCATAGAG AACTCTTCGC 3339
TTCATTTTTG ATGGCTGGCT CTGAAAGCAC CATGTGGAGT GGAGGTGGAG GGACCGAGGA 3399
ACCATGAATG AACTCGCAGG CAGTGCCGGG CGGCCCCCTG GCTCTCTGCG TTTTGCCTTT 3459
AACACTAACT GTACTGTTTT TTCTATTCAC GTGTGTCTAG CTGCAGGATG TAACATGAA 3519
AACAGTAACT AAAGATTAAA TTCAAGGAC TTTCAGAAGT TAAGGTTAAG TTTTACGTT 3579
TAATCTGCTG TTTACCTAAA CTTGTATGTA TAATTTTTGG GTGGGTATGG GGAATTGCTT 3639
TGCTAAAAAT AAGCTCCCAG GGTGTTTCAA ACTTAGAGAA GACCAAGGGA CAGTATTTTT 3699
TATCAAAGGA ATACTATTTT TTCACACTAC GTCAACTTGG TTGCTCTGAT ACCCCAGAGC 3759
CTGATTGGGG GCCTCCCGGC CTGGCTCAC GCCAAGTCCC TGGTGCTGGG TTTGCTCTCC 3819
CGCTGTTGCC AGGGGCTGGA AGCTGGAGGG GTCTCTTGGG CCATGGACAT CCCCACTTCC 3879
AGCCCATGTA CACTAGTGGC CCACGACCAA GGGGTCTTCA TTTCCATGAA AAAGGGACTC 3939
CAAGAGGCAG TGGTGGCTGT GGCCCCCAAC TTTGGTGCTC CAGGGTGGGC CAACTGCTTG 3999
TGGGGGCACC TGGGAGGTCA AAGGTCTCCA CCACATCAAC CTATTTTGTT TTACCCTTTT 4059
TCTGTGCATT GTTTTTTTT TTCCTCCTAA AAGGAATATC ACGGTTTTT GAAACACTCA 4119
GTGGGGGACA TTTTGGTGAA GATGCAATAT TTTTATGTCA TGTGATGCTC TTTCCTCACT 4179
TGACCTTGGC CGCTTTGTCC TAACAGTCCA CAGTCCTGCC CCGACCCACC CCATCCCTTT 4239
TCTCTGGCAC TCCAGTCCAG CTTGGGCCTG AACTACTGGA AAAGGTCTGG CGGCTGGGGA 4299
GGAGTGCCAG CAATAGTTCA TAATAAAAAT CTGTTAGCTC TCAAAGCTAA TTTTTACTA 4359
AAGTTTTTAT ACAGCCTCAA ATTGTTTTAT TAAAAAAAG ATTTAAAATG GTGATGCTTA 4419
CAGCAGTTTG TACGAGCTCT TAAGTGTTGA TTCCATGGAA CTGACGGCTT TGCTTGTTTT 4479
GATTCTTTTC CCCCTACTTT TCCTAATGGT TTAAATTCTG GAATTACACT GGGGTTCTTT 4539
TGCCTTTTTT AGCAGAACAT CCGTCCGTCC ATCTGCATCT CTGTCCCATG ACTCAGGGGC 4599
GCCCACTCTG CTTCGATTCT CCTCCTGTGG AAGAAACCAT TTGAGCATG ACTTTCTTG 4659
ATGTCTGAAG CGTTATTTTG GGTACTTTTT AGGGAGGAAT GCCTTTCGCA ATAATGTATC 4719
CATTCCCCTG ATTGAGGGTG GGTGGGTGGA CCCAGGCTCC CTTTGCACAC AGAGCAGCTA 4779
CTTCTAAGCC ATATCGACTG TTTTGCAGAG GATTTGTGTG TCCTCCCTCA GGAGGGGAGG 4839
CCTGGTAGGA GGGGGGGAGA GTTCTCTGTC CTACTGCTCT CAAGAGGGCA TTTCCCCTTG 4899
CGCCTTCTCC CACAGGGCCC AGCCCCTCTC CCCTGCCCAA GTCCCCAGGG GGTACTCTGG 4959
AGTGAGCAGT CCCCCTGTGG GGGAGCCTGT AAATGCGGGC TCAGTGGACC ACTGGTGACT 5019
GGGCTCATGC CTCCAAGTCA GAGTTTCCCC TGGTGCCCCA GAGACAGGAG CACAAGTGGG 5079
ATCTGACCTG GTGAGATTAT TTCTGATGAC CTCATCAAAA AATAAACAAT TCCCAATGTT 5139
CCAGGTGAGG GCTTTGAAAG GCCTTCCAAA CAGCTCCGTC GCCCTAGCA ACTCCACCAT 5199
TGGGCACTGC CATGCAGAGA CGTGGCTGGC CCAGAATGGC CTGTTGCCAT AGCAACTGGA 5259
GGCGATGGGG CAGTGAACAG AATAACAACA GCAACAATGC CTTTGCAGGC AGCCTGCTCC 5319
CCTGAGCGCT GGGCTGGTGA TGGCCGTTGG ACTCTGTGAG ATGGAGAGCC AATCTCACAT 5379
```

```
TCAAGTGTTC ACCAACCACT GATGTGTTTT TATTTCCTTC TATATGATTT TAAGATGTGT   5439

TTTCTGCATT CTGTAAAGAA ACATATCAAA CTAAATAAAA GCAGTGTCTT TATTAAAAAA   5499

AAAAAAAAAA A                                                       5510
```

( 2 ) INFORMATION FOR SEQ ID NO:8:

( i ) SEQUENCE CHARACTERISTICS:
        ( A ) LENGTH: 895 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Arg Met Ser Val Gly Leu Ser Leu Leu Leu Pro Leu Trp Gly Arg
 1               5                  10                  15

Thr Phe Leu Leu Leu Leu Ser Val Val Met Ala Gln Ser His Trp Pro
            20                  25                  30

Ser Glu Pro Ser Glu Ala Val Arg Asp Trp Glu Asn Gln Leu Glu Ala
        35                  40                  45

Ser Met His Ser Val Leu Ser Asp Leu His Glu Ala Val Pro Thr Val
    50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
                85                  90                  95

Ser Ala Ala Gly Lys Glu Ala Leu Pro Ser Trp Leu His Trp Asp Ser
            100                 105                 110

Gln Ser His Thr Leu Glu Gly Leu Pro Leu Asp Thr Asp Lys Gly Val
        115                 120                 125

His Tyr Ile Ser Val Ser Ala Thr Arg Leu Gly Ala Asn Gly Ser His
    130                 135                 140

Ile Pro Gln Thr Ser Ser Val Phe Ser Ile Glu Val Tyr Pro Glu Asp
145                 150                 155                 160

His Ser Asp Leu Gln Ser Val Arg Thr Ala Ser Pro Asp Pro Gly Glu
                165                 170                 175

Val Val Ser Ser Ala Cys Ala Ala Asp Glu Pro Val Thr Val Leu Thr
            180                 185                 190

Val Ile Leu Asp Ala Asp Leu Thr Lys Met Thr Pro Lys Gln Arg Ile
        195                 200                 205

Asp Leu Leu His Arg Met Arg Ser Phe Ser Glu Val Glu Leu His Asn
    210                 215                 220

Met Lys Leu Val Pro Val Val Asn Asn Arg Leu Phe Asp Met Ser Ala
225                 230                 235                 240

Phe Met Ala Gly Pro Gly Asn Pro Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
        275                 280                 285

Gln Leu Gly Tyr Pro Val Val Gly Trp His Ile Ala Asn Lys Lys Pro
    290                 295                 300

Pro Leu Pro Lys Arg Val Arg Arg Gln Ile His Ala Thr Pro Thr Pro
305                 310                 315                 320

Val Thr Ala Ile Gly Pro Pro Thr Thr Ala Ile Gln Glu Pro Pro Ser
```

-continued

|     |     |     |     | 325 |     |     |     |     | 330 |     |     |     |     | 335 |     |
| --- | --- | --- | --- | --- | --- | --- | --- | --- | --- | --- | --- | --- | --- | --- | --- |
| Arg | Ile | Val | Pro | Thr | Pro | Thr | Ser | Pro | Ala | Ile | Ala | Pro | Pro | Thr | Glu |
|     |     |     | 340 |     |     |     |     | 345 |     |     |     | 350 |     |     |     |
| Thr | Met | Ala | Pro | Pro | Val | Arg | Asp | Pro | Val | Pro | Gly | Lys | Pro | Thr | Val |
|     |     | 355 |     |     |     |     | 360 |     |     |     |     | 365 |     |     |     |
| Thr | Ile | Arg | Thr | Arg | Gly | Ala | Ile | Ile | Gln | Thr | Pro | Thr | Leu | Gly | Pro |
|     | 370 |     |     |     |     | 375 |     |     |     |     | 380 |     |     |     |     |
| Ile | Gln | Pro | Thr | Arg | Val | Ser | Glu | Ala | Gly | Thr | Thr | Val | Pro | Gly | Gln |
| 385 |     |     |     |     | 390 |     |     |     |     | 395 |     |     |     |     | 400 |
| Ile | Arg | Pro | Thr | Met | Thr | Ile | Pro | Gly | Tyr | Val | Glu | Pro | Thr | Ala | Val |
|     |     |     |     | 405 |     |     |     |     | 410 |     |     |     |     | 415 |     |
| Ala | Thr | Pro | Pro | Thr | Thr | Thr | Thr | Lys | Lys | Pro | Arg | Val | Ser | Thr | Pro |
|     |     |     | 420 |     |     |     |     | 425 |     |     |     |     | 430 |     |     |
| Lys | Pro | Ala | Thr | Pro | Ser | Thr | Asp | Ser | Thr | Thr | Thr | Thr | Thr | Arg | Arg |
|     |     | 435 |     |     |     |     | 440 |     |     |     |     | 445 |     |     |     |
| Pro | Thr | Lys | Lys | Pro | Arg | Thr | Pro | Arg | Pro | Val | Pro | Arg | Val | Thr | Thr |
|     | 450 |     |     |     |     | 455 |     |     |     |     | 460 |     |     |     |     |
| Lys | Val | Ser | Ile | Thr | Arg | Leu | Glu | Thr | Ala | Ser | Pro | Pro | Thr | Arg | Ile |
| 465 |     |     |     |     | 470 |     |     |     |     | 475 |     |     |     |     | 480 |
| Arg | Thr | Thr | Thr | Ser | Gly | Val | Pro | Arg | Gly | Gly | Glu | Pro | Asn | Gln | Arg |
|     |     |     |     | 485 |     |     |     |     | 490 |     |     |     |     | 495 |     |
| Pro | Glu | Leu | Lys | Asn | His | Ile | Asp | Arg | Val | Asp | Ala | Trp | Val | Gly | Thr |
|     |     |     |     | 500 |     |     |     |     | 505 |     |     |     |     | 510 |     |
| Tyr | Phe | Glu | Val | Lys | Ile | Pro | Ser | Asp | Thr | Phe | Tyr | Asp | His | Glu | Asp |
|     |     | 515 |     |     |     |     | 520 |     |     |     |     | 525 |     |     |     |
| Thr | Thr | Thr | Asp | Lys | Leu | Lys | Leu | Thr | Leu | Lys | Leu | Arg | Glu | Gln | Gln |
|     | 530 |     |     |     |     | 535 |     |     |     |     | 540 |     |     |     |     |
| Leu | Val | Gly | Glu | Lys | Ser | Trp | Val | Gln | Phe | Asn | Ser | Asn | Ser | Gln | Leu |
| 545 |     |     |     |     | 550 |     |     |     |     | 555 |     |     |     |     | 560 |
| Met | Tyr | Gly | Leu | Pro | Asp | Ser | Ser | His | Val | Gly | Lys | His | Glu | Tyr | Phe |
|     |     |     |     | 565 |     |     |     |     | 570 |     |     |     |     | 575 |     |
| Met | His | Ala | Thr | Asp | Lys | Gly | Gly | Leu | Ser | Ala | Val | Asp | Ala | Phe | Glu |
|     |     |     | 580 |     |     |     |     | 585 |     |     |     |     | 590 |     |     |
| Ile | His | Val | His | Arg | Arg | Pro | Gln | Gly | Asp | Arg | Ala | Pro | Ala | Arg | Phe |
|     |     |     |     | 595 |     |     |     |     | 600 |     |     |     |     | 605 |     |
| Lys | Ala | Lys | Phe | Val | Gly | Asp | Pro | Ala | Leu | Val | Leu | Asn | Asp | Ile | His |
|     | 610 |     |     |     |     | 615 |     |     |     |     | 620 |     |     |     |     |
| Lys | Lys | Ile | Ala | Leu | Val | Lys | Lys | Leu | Ala | Phe | Ala | Phe | Gly | Asp | Arg |
| 625 |     |     |     |     | 630 |     |     |     |     | 635 |     |     |     |     | 640 |
| Asn | Cys | Ser | Thr | Ile | Thr | Leu | Gln | Asn | Ile | Thr | Arg | Gly | Ser | Ile | Val |
|     |     |     |     | 645 |     |     |     |     | 650 |     |     |     |     | 655 |     |
| Val | Glu | Trp | Thr | Asn | Asn | Thr | Leu | Pro | Leu | Glu | Pro | Cys | Pro | Lys | Glu |
|     |     |     | 660 |     |     |     |     | 665 |     |     |     |     | 670 |     |     |
| Gln | Ile | Ala | Gly | Leu | Ser | Arg | Arg | Ile | Ala | Glu | Asp | Gly | Lys | Pro |     |
|     |     |     | 675 |     |     |     |     | 680 |     |     |     |     | 685 |     |     |
| Arg | Pro | Ala | Phe | Ser | Asn | Ala | Leu | Glu | Pro | Asp | Phe | Lys | Ala | Thr | Ser |
|     | 690 |     |     |     |     | 695 |     |     |     |     | 700 |     |     |     |     |
| Ile | Thr | Val | Thr | Gly | Ser | Gly | Ser | Cys | Arg | His | Leu | Gln | Phe | Ile | Pro |
| 705 |     |     |     |     | 710 |     |     |     |     | 715 |     |     |     |     | 720 |
| Val | Val | Pro | Pro | Arg | Arg | Val | Pro | Ser | Glu | Ala | Pro | Pro | Thr | Glu | Val |
|     |     |     |     | 725 |     |     |     |     | 730 |     |     |     |     | 735 |     |
| Pro | Asp | Arg | Asp | Pro | Glu | Lys | Ser | Ser | Glu | Asp | Asp | Val | Tyr | Leu | His |
|     |     |     | 740 |     |     |     |     | 745 |     |     |     |     | 750 |     |     |

| | | | | | | | | | | | | | | |
|---|---|---|---|---|---|---|---|---|---|---|---|---|---|---|
| Thr | Val | Ile | Pro | Ala | Val | Val | Ala | Ala | Ile | Leu | Leu | Ile | Ala | Gly |
| | | 755 | | | | 760 | | | | 765 | | | | |
| Ile | Ile | Ala | Met | Ile | Cys | Tyr | Arg | Lys | Lys | Arg | Lys | Gly | Lys | Leu | Thr |
| | 770 | | | | 775 | | | | 780 | | | | | |
| Leu | Glu | Asp | Gln | Ala | Thr | Phe | Ile | Lys | Lys | Gly | Val | Pro | Ile | Ile | Phe |
| 785 | | | | | 790 | | | | | 795 | | | | | 800 |
| Ala | Asp | Glu | Leu | Asp | Asp | Ser | Lys | Pro | Pro | Pro | Ser | Ser | Ser | Met | Pro |
| | | | | 805 | | | | | 810 | | | | | 815 | |
| Leu | Ile | Leu | Gln | Glu | Glu | Lys | Ala | Pro | Leu | Pro | Pro | Pro | Glu | Tyr | Pro |
| | | | 820 | | | | | 825 | | | | | 830 | | |
| Asn | Gln | Ser | Val | Pro | Glu | Thr | Thr | Pro | Leu | Asn | Gln | Asp | Thr | Met | Gly |
| | | 835 | | | | | 840 | | | | | 845 | | | |
| Glu | Tyr | Thr | Pro | Leu | Arg | Asp | Glu | Asp | Pro | Asn | Ala | Pro | Pro | Tyr | Gln |
| | 850 | | | | | 855 | | | | | 860 | | | | |
| Pro | Pro | Pro | Pro | Phe | Thr | Val | Pro | Met | Glu | Gly | Lys | Gly | Ser | Arg | Pro |
| 865 | | | | | 870 | | | | | 875 | | | | | 880 |
| Lys | Asn | Met | Thr | Pro | Tyr | Arg | Ser | Pro | Pro | Pro | Tyr | Val | Pro | Pro | |
| | | | | 885 | | | | | 890 | | | | | 895 | |

( 2 ) INFORMATION FOR SEQ ID NO:9:

( i ) SEQUENCE CHARACTERISTICS:
        ( A ) LENGTH: 1472 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 253..1413

( x i ) SEQUENCE DESCRIPTION: SEQ ID NO:9:

```
ATAAGTGTAT  TTGTGGTAGT  TTGGGCTGGG  TGAATTCAGA  CTGGTGTTTG  GCGGTGCAAA      60

CGAGTAGCAT  GGTGTCTGCT  GCATCATGCT  GCCAGGTGAA  GACTGGGTGG  AAACAGTTAA     120

TGATGTTGGT  GATGAGAGAA  GATTGAGATT  ATCCAAAAGG  TTTTCCATGT  TCACAGGAT     180

TGCTTATCTC  AGACAGACTG  GGGAGAGTAG  AAGCCATCTT  GGCAGACGAC  GGTGGGTACA    240

CGCCGGGCAG  CC ATG GCG GCG GCC GCG CTC CTC TGG CTC CCT CTC CTT            288
              Met Ala Ala Ala Ala Leu Leu Trp Leu Pro Leu Leu
                1               5                  10
```

| GTG | GGC | TGC | CTG | GCA | GGC | CCG | GGA | GGC | ACC | GAG | GCC | CAG | CAG | ACC | ACC | 336 |
| Val | Gly | Cys | Leu | Ala | Gly | Pro | Gly | Gly | Thr | Glu | Ala | Gln | Gln | Thr | Thr | |
| | | 15 | | | | | 20 | | | | | 25 | | | | |

| CTG | TAC | CCA | CTT | GTG | GGC | CGC | GTC | TTC | GTG | CAC | ACC | TTG | GAG | CCT | GCG | 384 |
| Leu | Tyr | Pro | Leu | Val | Gly | Arg | Val | Phe | Val | His | Thr | Leu | Glu | Pro | Ala | |
| | 30 | | | | | 35 | | | | | 40 | | | | | |

| AGC | TTC | CTG | CAC | CTC | CCG | GAG | CAC | GCT | GCC | CCA | GCC | ACC | ATC | CCC | GTC | 432 |
| Ser | Phe | Leu | His | Leu | Pro | Glu | His | Ala | Ala | Pro | Ala | Thr | Ile | Pro | Val | |
| 45 | | | | | 50 | | | | | 55 | | | | | 60 | |

| ACC | TAC | CAC | GCC | CAC | CTC | CAA | GGA | CAC | CCA | GAC | CTG | CCT | CGG | TGG | CTC | 480 |
| Thr | Tyr | His | Ala | His | Leu | Gln | Gly | His | Pro | Asp | Leu | Pro | Arg | Trp | Leu | |
| | | | | 65 | | | | | 70 | | | | | 75 | | |

| CGC | TAC | ACC | CAG | CGC | AGC | CCC | CAC | CAC | CCT | GGC | TTC | CTG | TAC | GGC | GCA | 528 |
| Arg | Tyr | Thr | Gln | Arg | Ser | Pro | His | His | Pro | Gly | Phe | Leu | Tyr | Gly | Ala | |
| | | | 80 | | | | | 85 | | | | | 90 | | | |

| GCC | ACC | CCA | GAG | GAT | CGT | GGA | GCG | CAG | GTC | ATC | GAG | GTC | ACC | GCC | TAC | 576 |
| Ala | Thr | Pro | Glu | Asp | Arg | Gly | Arg | Gln | Val | Ile | Glu | Val | Thr | Ala | Tyr | |
| | | 95 | | | | | 100 | | | | | 105 | | | | |

```
AAC CGC GAC AGC TTC GAC ACC GCC GGA CAG AGC CTG GTG CTG CTG ATC        624
Asn Arg Asp Ser Phe Asp Thr Ala Gly Gln Ser Leu Val Leu Leu Ile
    110             115                 120

CGG GAC CCA GAA GGG TCC CCA CTG CCC TAC CAG ACT GAG TTC CTG GTG        672
Arg Asp Pro Glu Gly Ser Pro Leu Pro Tyr Gln Thr Glu Phe Leu Val
125             130                 135                 140

CGT AGC CAC GAT GTG GAA GAG GTG CTG CCC CCG ACA CCC GCC AGC CAC        720
Arg Ser His Asp Val Glu Glu Val Leu Pro Pro Thr Pro Ala Ser His
                145                 150                 155

TTC CTC ACG GCC TTG GCG GGG CTC TGG GAG CCC GGC GAG CTC AAG CTG        768
Phe Leu Thr Ala Leu Ala Gly Leu Trp Glu Pro Gly Glu Leu Lys Leu
        160                 165                 170

CTC AAC ATC ACT TCA GCC TTG GAT CGT GGG GGC CGT GTC CCC CTT CCC        816
Leu Asn Ile Thr Ser Ala Leu Asp Arg Gly Gly Arg Val Pro Leu Pro
            175                 180                 185

ATC GGG GGC CAA AAG GAA GGG GTA TAC ATC AAG GTG GGC TCC GCC TCA        864
Ile Gly Gly Gln Lys Glu Gly Val Tyr Ile Lys Val Gly Ser Ala Ser
        190                 195                 200

CCC TTC TCC ACC TGC CTG AAG ATG GTG GCG TCC CCT GAC AGC CAT GCC        912
Pro Phe Ser Thr Cys Leu Lys Met Val Ala Ser Pro Asp Ser His Ala
205             210                 215                 220

CGC TGT GCC CGG GGC CAG CCT CCG CTT CTG TCC TGC TAC GAC ACC TTG        960
Arg Cys Ala Arg Gly Gln Pro Pro Leu Leu Ser Cys Tyr Asp Thr Leu
                225                 230                 235

GCT CCT CAT TTC CGC GTT GAC TGG TGC AAT GTG TCC CTG GTG GAT ACG       1008
Ala Pro His Phe Arg Val Asp Trp Cys Asn Val Ser Leu Val Asp Thr
            240                 245                 250

TCA GTG CCA GAG CCG GTG GAT GAG GTG CCC ACC CCA GGC GAT GGG ATT       1056
Ser Val Pro Glu Pro Val Asp Glu Val Pro Thr Pro Gly Asp Gly Ile
        255                 260                 265

CTG GAG CAC GAC CCC TTC TTC TGC CCT CCC ACC GAG GCC ACT GCC CGA       1104
Leu Glu His Asp Pro Phe Phe Cys Pro Pro Thr Glu Ala Thr Ala Arg
    270                 275                 280

GAC TTC CTG GCA GAC GCC CTG GTC ACC CTG CTG GTG CCC CTG CTG GTG       1152
Asp Phe Leu Ala Asp Ala Leu Val Thr Leu Leu Val Pro Leu Leu Val
285             290                 295                 300

GCC CTG CTA CTT GCC CTG CTG CTG GCC TAC ATC ATG TGC TGC CGA CGG       1200
Ala Leu Leu Leu Ala Leu Leu Leu Ala Tyr Ile Met Cys Cys Arg Arg
                305                 310                 315

GAG GGG CGG CTG AAG AGA GAT CTG GCC ACT TCT GAC ATC CAG ATG GTC       1248
Glu Gly Arg Leu Lys Arg Asp Leu Ala Thr Ser Asp Ile Gln Met Val
            320                 325                 330

CAC CAT TGC ACC ATC CAC GAG AAC ACG GAG GAG CTA CGG CAG ATG GCA       1296
His His Cys Thr Ile His Glu Asn Thr Glu Glu Leu Arg Gln Met Ala
        335                 340                 345

GCC AGC CGC GAG GTG CCC CGG CCA CTC TTT CCC CTG CCC ATG TTC AAC       1344
Ala Ser Arg Glu Val Pro Arg Pro Leu Phe Pro Leu Pro Met Phe Asn
350                 355                 360

GTG CGC ACG GGT GAG CGG ATG CCT CCT CGG GTG GAC AGC GCC CAG GTG       1392
Val Arg Thr Gly Glu Arg Met Pro Pro Arg Val Asp Ser Ala Gln Val
365             370                 375                 380

CCC CTC ATC CTG GAC CAG CAC TGAGAGCCCA GACAGAGACC GTCTTGGCCA          1443
Pro Leu Ile Leu Asp Gln His
                385

CCTCCCACCT GGTGATTCCA GCTCCTGGT                                        1472
```

( 2 ) INFORMATION FOR SEQ ID NO:10:

( i ) SEQUENCE CHARACTERISTICS:
        ( A ) LENGTH: 387 amino acids
        ( B ) TYPE: amino acid -continued ( D ) TOPOLOGY: linear ( i i ) MOLECULE TYPE: protein ( x i ) SEQUENCE DESCRIPTION: SEQ ID NO:10:

| Met | Ala | Ala | Ala | Ala | Leu | Leu | Trp | Leu | Pro | Leu | Leu | Val | Gly | Cys | Leu |
|---|---|---|---|---|---|---|---|---|---|---|---|---|---|---|---|
| 1 | | | | 5 | | | | | 10 | | | | | 15 | |

| Ala | Gly | Pro | Gly | Gly | Thr | Glu | Ala | Gln | Gln | Thr | Thr | Leu | Tyr | Pro | Leu |
|---|---|---|---|---|---|---|---|---|---|---|---|---|---|---|---|
| | | | 20 | | | | | 25 | | | | | 30 | | |

| Val | Gly | Arg | Val | Phe | Val | His | Thr | Leu | Glu | Pro | Ala | Ser | Phe | Leu | His |
|---|---|---|---|---|---|---|---|---|---|---|---|---|---|---|---|
| | | 35 | | | | | 40 | | | | | 45 | | | |

| Leu | Pro | Glu | His | Ala | Ala | Pro | Ala | Thr | Ile | Pro | Val | Thr | Tyr | His | Ala |
|---|---|---|---|---|---|---|---|---|---|---|---|---|---|---|---|
| | 50 | | | | | 55 | | | | | 60 | | | | |

| His | Leu | Gln | Gly | His | Pro | Asp | Leu | Pro | Arg | Trp | Leu | Arg | Tyr | Thr | Gln |
|---|---|---|---|---|---|---|---|---|---|---|---|---|---|---|---|
| 65 | | | | | 70 | | | | | 75 | | | | | 80 |

| Arg | Ser | Pro | His | His | Pro | Gly | Phe | Leu | Tyr | Gly | Ala | Ala | Thr | Pro | Glu |
|---|---|---|---|---|---|---|---|---|---|---|---|---|---|---|---|
| | | | | 85 | | | | | 90 | | | | | 95 | |

| Asp | Arg | Gly | Arg | Gln | Val | Ile | Glu | Val | Thr | Ala | Tyr | Asn | Arg | Asp | Ser |
|---|---|---|---|---|---|---|---|---|---|---|---|---|---|---|---|
| | | | 100 | | | | | 105 | | | | | 110 | | |

| Phe | Asp | Thr | Ala | Gly | Gln | Ser | Leu | Val | Leu | Leu | Ile | Arg | Asp | Pro | Glu |
|---|---|---|---|---|---|---|---|---|---|---|---|---|---|---|---|
| | | 115 | | | | | 120 | | | | | 125 | | | |

| Gly | Ser | Pro | Leu | Pro | Tyr | Gln | Thr | Glu | Phe | Leu | Val | Arg | Ser | His | Asp |
|---|---|---|---|---|---|---|---|---|---|---|---|---|---|---|---|
| | 130 | | | | | 135 | | | | | 140 | | | | |

| Val | Glu | Glu | Val | Leu | Pro | Pro | Thr | Pro | Ala | Ser | His | Phe | Leu | Thr | Ala |
|---|---|---|---|---|---|---|---|---|---|---|---|---|---|---|---|
| 145 | | | | | 150 | | | | | 155 | | | | | 160 |

| Leu | Ala | Gly | Leu | Trp | Glu | Pro | Gly | Glu | Leu | Lys | Leu | Leu | Asn | Ile | Thr |
|---|---|---|---|---|---|---|---|---|---|---|---|---|---|---|---|
| | | | | 165 | | | | | 170 | | | | | 175 | |

| Ser | Ala | Leu | Asp | Arg | Gly | Gly | Arg | Val | Pro | Leu | Pro | Ile | Gly | Gly | Gln |
|---|---|---|---|---|---|---|---|---|---|---|---|---|---|---|---|
| | | | 180 | | | | | 185 | | | | | 190 | | |

| Lys | Glu | Gly | Val | Tyr | Ile | Lys | Val | Gly | Ser | Ala | Ser | Pro | Phe | Ser | Thr |
|---|---|---|---|---|---|---|---|---|---|---|---|---|---|---|---|
| | | 195 | | | | | 200 | | | | | 205 | | | |

| Cys | Leu | Lys | Met | Val | Ala | Ser | Pro | Asp | Ser | His | Ala | Arg | Cys | Ala | Arg |
|---|---|---|---|---|---|---|---|---|---|---|---|---|---|---|---|
| | 210 | | | | | 215 | | | | | 220 | | | | |

| Gly | Gln | Pro | Pro | Leu | Leu | Ser | Cys | Tyr | Asp | Thr | Leu | Ala | Pro | His | Phe |
|---|---|---|---|---|---|---|---|---|---|---|---|---|---|---|---|
| 225 | | | | | 230 | | | | | 235 | | | | | 240 |

| Arg | Val | Asp | Trp | Cys | Asn | Val | Ser | Leu | Val | Asp | Thr | Ser | Val | Pro | Glu |
|---|---|---|---|---|---|---|---|---|---|---|---|---|---|---|---|
| | | | | 245 | | | | | 250 | | | | | 255 | |

| Pro | Val | Asp | Glu | Val | Pro | Thr | Pro | Gly | Asp | Gly | Ile | Leu | Glu | His | Asp |
|---|---|---|---|---|---|---|---|---|---|---|---|---|---|---|---|
| | | | 260 | | | | | 265 | | | | | 270 | | |

| Pro | Phe | Phe | Cys | Pro | Pro | Thr | Glu | Ala | Thr | Ala | Arg | Asp | Phe | Leu | Ala |
|---|---|---|---|---|---|---|---|---|---|---|---|---|---|---|---|
| | | 275 | | | | | 280 | | | | | 285 | | | |

| Asp | Ala | Leu | Val | Thr | Leu | Leu | Val | Pro | Leu | Leu | Val | Ala | Leu | Leu | Leu |
|---|---|---|---|---|---|---|---|---|---|---|---|---|---|---|---|
| | 290 | | | | | 295 | | | | | 300 | | | | |

| Ala | Leu | Leu | Leu | Ala | Tyr | Ile | Met | Cys | Cys | Arg | Arg | Glu | Gly | Arg | Leu |
|---|---|---|---|---|---|---|---|---|---|---|---|---|---|---|---|
| 305 | | | | | 310 | | | | | 315 | | | | | 320 |

| Lys | Arg | Asp | Leu | Ala | Thr | Ser | Asp | Ile | Gln | Met | Val | His | His | Cys | Thr |
|---|---|---|---|---|---|---|---|---|---|---|---|---|---|---|---|
| | | | | 325 | | | | | 330 | | | | | 335 | |

| Ile | His | Glu | Asn | Thr | Glu | Glu | Leu | Arg | Gln | Met | Ala | Ala | Ser | Arg | Glu |
|---|---|---|---|---|---|---|---|---|---|---|---|---|---|---|---|
| | | | 340 | | | | | 345 | | | | | 350 | | |

| Val | Pro | Arg | Pro | Leu | Phe | Pro | Leu | Pro | Met | Phe | Asn | Val | Arg | Thr | Gly |
|---|---|---|---|---|---|---|---|---|---|---|---|---|---|---|---|
| | | 355 | | | | | 360 | | | | | 365 | | | |

| Glu | Arg | Met | Pro | Pro | Arg | Val | Asp | Ser | Ala | Gln | Val | Pro | Leu | Ile | Leu |
|---|---|---|---|---|---|---|---|---|---|---|---|---|---|---|---|
| 370 | | | | | 375 | | | | | 380 | | | | | |

| Asp | Gln | His |
|---|---|---|
| 385 | | |

( 2 ) INFORMATION FOR SEQ ID NO:11:

( i ) SEQUENCE CHARACTERISTICS:
        ( A ) LENGTH: 1396 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 4..1164

( x i ) SEQUENCE DESCRIPTION: SEQ ID NO:11:

```
GCC ATG GCT GAG ACA CTC TTC TGG ACT CCT CTC CTC GTG GTT CTC CTG        48
    Met Ala Glu Thr Leu Phe Trp Thr Pro Leu Leu Val Val Leu Leu
    1               5                   10                  15

GCA GGG CTG GGG GAC ACC GAG GCC CAG CAG ACC ACG CTA CAC CCA CTT        96
Ala Gly Leu Gly Asp Thr Glu Ala Gln Gln Thr Thr Leu His Pro Leu
                20                  25                  30

GTG GGC CGT GTC TTT GTG CAC ACC TTG GAC CAT GAG ACG TTT CTG AGC       144
Val Gly Arg Val Phe Val His Thr Leu Asp His Glu Thr Phe Leu Ser
            35                  40                  45

CTT CCT GAG CAT GTC GCT GTC CCA CCC GCT GTC CAC ATC ACC TAC CAC       192
Leu Pro Glu His Val Ala Val Pro Pro Ala Val His Ile Thr Tyr His
        50                  55                  60

GCC CAC CTC CAG GGA CAC CCA GAC CTG CCC CGG TGG CTC CGC TAC ACC       240
Ala His Leu Gln Gly His Pro Asp Leu Pro Arg Trp Leu Arg Tyr Thr
    65                  70                  75

CAG CGC AGC CCC CAC CAC CCC GGC TTC CTC TAC GGC TCT GCC ACC CCA       288
Gln Arg Ser Pro His His Pro Gly Phe Leu Tyr Gly Ser Ala Thr Pro
80                  85                  90                  95

GAA GAT CGT GGG CTC CAG GTC ATT GAG GTC ACA GCC TAC AAT CGG GAC       336
Glu Asp Arg Gly Leu Gln Val Ile Glu Val Thr Ala Tyr Asn Arg Asp
                100                 105                 110

AGC TTT GAT ACC ACT CGG CAG AGG CTG GTG CTG GAG ATT GGG GAC CCA       384
Ser Phe Asp Thr Thr Arg Gln Arg Leu Val Leu Glu Ile Gly Asp Pro
            115                 120                 125

GAA GGC CCC CTG CTG CCA TAC CAA GCC GAG TTC CTG GTG CGC AGC CAC       432
Glu Gly Pro Leu Leu Pro Tyr Gln Ala Glu Phe Leu Val Arg Ser His
        130                 135                 140

GAT GCG GAG GAG GTG CTG CCC TCA ACA CCT GCC AGC CGC TTC CTC TCA       480
Asp Ala Glu Glu Val Leu Pro Ser Thr Pro Ala Ser Arg Phe Leu Ser
    145                 150                 155

GCC TTG GGG GGA CTC TGG GAG CCC GGA GAG CTT CAG CTG CTC AAC GTC       528
Ala Leu Gly Gly Leu Trp Glu Pro Gly Glu Leu Gln Leu Leu Asn Val
160                 165                 170                 175

ACC TCT GCC TTG GAC CGT GGG GGC CGT GTC CCC CTT CCC ATT GAG GGC       576
Thr Ser Ala Leu Asp Arg Gly Gly Arg Val Pro Leu Pro Ile Glu Gly
                180                 185                 190

CGA AAA GAA GGG GTA TAC ATT AAG GTG GGT TCT GCC TCA CCT TTT TCT       624
Arg Lys Glu Gly Val Tyr Ile Lys Val Gly Ser Ala Ser Pro Phe Ser
            195                 200                 205

ACT TGC CTG AAG ATG GTG GCA TCC CCC GAT AGC CAC GCC CGC TGT GCC       672
Thr Cys Leu Lys Met Val Ala Ser Pro Asp Ser His Ala Arg Cys Ala
        210                 215                 220

CAG GGC CAG CCT CCA CTT CTG TCT TGC TAC GAC ACC TTG GCA CCC CAC       720
Gln Gly Gln Pro Pro Leu Leu Ser Cys Tyr Asp Thr Leu Ala Pro His
    225                 230                 235

TTC CGC GTT GAC TGG TGC AAT GTG ACC CTG GTG GAT AAG TCA GTG CCG       768
Phe Arg Val Asp Trp Cys Asn Val Thr Leu Val Asp Lys Ser Val Pro
```

-continued

```
        240                     245                       250                         255
GAG  CCT  GCA  GAT  GAG  GTG  CCC  ACC  CCA  GGT  GAT  GGG  ATC  CTG  GAG  CAT     816
Glu  Pro  Ala  Asp  Glu  Val  Pro  Thr  Pro  Gly  Asp  Gly  Ile  Leu  Glu  His
               260                      265                      270

GAC  CCG  TTC  TTC  TGC  CCA  CCC  ACT  GAG  GCC  CCA  GAC  CGT  GAC  TTC  TTG     864
Asp  Pro  Phe  Phe  Cys  Pro  Pro  Thr  Glu  Ala  Pro  Asp  Arg  Asp  Phe  Leu
                    275                      280                      285

GTG  GAT  GCT  CTG  GTC  ACC  CTC  CTG  GTG  CCC  CTG  CTG  GTG  GCC  CTG  CTT     912
Val  Asp  Ala  Leu  Val  Thr  Leu  Leu  Val  Pro  Leu  Leu  Val  Ala  Leu  Leu
               290                      295                      300

CTC  ACC  TTG  CTG  CTG  GCC  TAT  GTC  ATG  TGC  TGC  CGG  CGG  GAG  GGA  AGG     960
Leu  Thr  Leu  Leu  Leu  Ala  Tyr  Val  Met  Cys  Cys  Arg  Arg  Glu  Gly  Arg
               305                      310                      315

CTG  AAG  AGA  GAC  CTG  GCT  ACC  TCC  GAC  ATC  CAG  ATG  GTC  CAC  CAC  TGC    1008
Leu  Lys  Arg  Asp  Leu  Ala  Thr  Ser  Asp  Ile  Gln  Met  Val  His  His  Cys
320                      325                      330                      335

ACC  ATC  CAC  GGG  AAC  ACA  GAG  GAG  CTG  CGG  CAG  ATG  GCG  GCC  AGC  CGC    1056
Thr  Ile  His  Gly  Asn  Thr  Glu  Glu  Leu  Arg  Gln  Met  Ala  Ala  Ser  Arg
                         340                      345                      350

GAG  GTG  CCC  CGG  CCA  CTC  TCC  ACC  CTG  CCC  ATG  TTC  AAT  GTG  CAC  ACA    1104
Glu  Val  Pro  Arg  Pro  Leu  Ser  Thr  Leu  Pro  Met  Phe  Asn  Val  His  Thr
               355                      360                      365

GGT  GAG  CGG  CTG  CCT  CCC  CGC  GTG  GAC  AGC  GCC  CAG  GTG  CCC  CTC  ATT    1152
Gly  Glu  Arg  Leu  Pro  Pro  Arg  Val  Asp  Ser  Ala  Gln  Val  Pro  Leu  Ile
          370                      375                      380

CTG  GAC  CAG  CAC  TGACAGCCCA  GCCAGTGGTT  CCAGGTCCAG  CCCTGACTTC               1204
Leu  Asp  Gln  His
          385

ATCCTCCCTT  CTCTGTCCAC  ACCACGAGTG  GCACATCCCA  CCTGCTGATT  CCAGCTCCTG           1264

GCCCTCCTGG  AACCCAGGCT  CTAAACAAGC  AGGGAGAGGG  GGTGGGGTGG  GGTGAGAGTG           1324

TGTGGAGTAA  GGACATTCAG  AATAAATATC  TGCTGCTCTG  CTCACCAAAA  AAAAAAAAAA           1384

AAAAAAAAA   AA                                                                   1396
```

( 2 ) INFORMATION FOR SEQ ID NO:12:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Ala  Glu  Thr  Leu  Phe  Trp  Thr  Pro  Leu  Leu  Val  Val  Leu  Leu  Ala
  1                 5                      10                      15

Gly  Leu  Gly  Asp  Thr  Glu  Ala  Gln  Gln  Thr  Thr  Leu  His  Pro  Leu  Val
               20                      25                      30

Gly  Arg  Val  Phe  Val  His  Thr  Leu  Asp  His  Glu  Thr  Phe  Leu  Ser  Leu
          35                      40                      45

Pro  Glu  His  Val  Ala  Val  Pro  Pro  Ala  Val  His  Ile  Thr  Tyr  His  Ala
     50                      55                      60

His  Leu  Gln  Gly  His  Pro  Asp  Leu  Pro  Arg  Trp  Leu  Arg  Tyr  Thr  Gln
65                      70                      75                      80

Arg  Ser  Pro  His  His  Pro  Gly  Phe  Leu  Tyr  Gly  Ser  Ala  Thr  Pro  Glu
                    85                      90                      95

Asp  Arg  Gly  Leu  Gln  Val  Ile  Glu  Val  Thr  Ala  Tyr  Asn  Arg  Asp  Ser
               100                     105                     110

Phe  Asp  Thr  Thr  Arg  Gln  Arg  Leu  Val  Leu  Glu  Ile  Gly  Asp  Pro  Glu
```

|     |     |     |     | 115 |     |     |     |     | 120 |     |     |     |     | 125 |
| --- | --- | --- | --- | --- | --- | --- | --- | --- | --- | --- | --- | --- | --- | --- |
| Gly | Pro | Leu | Leu | Pro | Tyr | Gln | Ala | Glu | Phe | Leu | Val | Arg | Ser | His | Asp |
|     | 130 |     |     |     | 135 |     |     |     |     | 140 |     |     |     |     |     |
| Ala | Glu | Glu | Val | Leu | Pro | Ser | Thr | Pro | Ala | Ser | Arg | Phe | Leu | Ser | Ala |
| 145 |     |     |     |     | 150 |     |     |     |     | 155 |     |     |     |     | 160 |
| Leu | Gly | Gly | Leu | Trp | Glu | Pro | Gly | Glu | Leu | Gln | Leu | Leu | Asn | Val | Thr |
|     |     |     |     | 165 |     |     |     |     | 170 |     |     |     |     | 175 |     |
| Ser | Ala | Leu | Asp | Arg | Gly | Gly | Arg | Val | Pro | Leu | Pro | Ile | Glu | Gly | Arg |
|     |     |     | 180 |     |     |     |     | 185 |     |     |     |     | 190 |     |     |
| Lys | Glu | Gly | Val | Tyr | Ile | Lys | Val | Gly | Ser | Ala | Ser | Pro | Phe | Ser | Thr |
|     |     | 195 |     |     |     |     | 200 |     |     |     |     | 205 |     |     |     |
| Cys | Leu | Lys | Met | Val | Ala | Ser | Pro | Asp | Ser | His | Ala | Arg | Cys | Ala | Gln |
|     | 210 |     |     |     |     | 215 |     |     |     |     | 220 |     |     |     |     |
| Gly | Gln | Pro | Pro | Leu | Leu | Ser | Cys | Tyr | Asp | Thr | Leu | Ala | Pro | His | Phe |
| 225 |     |     |     |     | 230 |     |     |     | 235 |     |     |     |     |     | 240 |
| Arg | Val | Asp | Trp | Cys | Asn | Val | Thr | Leu | Val | Asp | Lys | Ser | Val | Pro | Glu |
|     |     |     |     | 245 |     |     |     |     | 250 |     |     |     |     | 255 |     |
| Pro | Ala | Asp | Glu | Val | Pro | Thr | Pro | Gly | Asp | Gly | Ile | Leu | Glu | His | Asp |
|     |     |     | 260 |     |     |     |     | 265 |     |     |     |     | 270 |     |     |
| Pro | Phe | Phe | Cys | Pro | Pro | Thr | Glu | Ala | Pro | Asp | Arg | Asp | Phe | Leu | Val |
|     |     | 275 |     |     |     |     | 280 |     |     |     |     | 285 |     |     |     |
| Asp | Ala | Leu | Val | Thr | Leu | Leu | Val | Pro | Leu | Leu | Val | Ala | Leu | Leu | Leu |
|     | 290 |     |     |     |     | 295 |     |     |     |     | 300 |     |     |     |     |
| Thr | Leu | Leu | Leu | Ala | Tyr | Val | Met | Cys | Cys | Arg | Arg | Glu | Gly | Arg | Leu |
| 305 |     |     |     |     | 310 |     |     |     |     | 315 |     |     |     |     | 320 |
| Lys | Arg | Asp | Leu | Ala | Thr | Ser | Asp | Ile | Gln | Met | Val | His | His | Cys | Thr |
|     |     |     |     | 325 |     |     |     |     | 330 |     |     |     |     | 335 |     |
| Ile | His | Gly | Asn | Thr | Glu | Glu | Leu | Arg | Gln | Met | Ala | Ala | Ser | Arg | Glu |
|     |     |     | 340 |     |     |     |     | 345 |     |     |     |     | 350 |     |     |
| Val | Pro | Arg | Pro | Leu | Ser | Thr | Leu | Pro | Met | Phe | Asn | Val | His | Thr | Gly |
|     |     | 355 |     |     |     |     | 360 |     |     |     |     | 365 |     |     |     |
| Glu | Arg | Leu | Pro | Pro | Arg | Val | Asp | Ser | Ala | Gln | Val | Pro | Leu | Ile | Leu |
|     | 370 |     |     |     |     | 375 |     |     |     |     | 380 |     |     |     |     |
| Asp | Gln | His |     |     |     |     |     |     |     |     |     |     |     |     |     |
| 385 |     |     |     |     |     |     |     |     |     |     |     |     |     |     |     |

( 2 ) INFORMATION FOR SEQ ID NO:13:

( i ) SEQUENCE CHARACTERISTICS:
  ( A ) LENGTH: 2389 base pairs
  ( B ) TYPE: nucleic acid
  ( C ) STRANDEDNESS: double
  ( D ) TOPOLOGY: linear ( i i ) MOLECULE TYPE: cDNA ( i x ) FEATURE:
  ( A ) NAME/KEY: CDS
  ( B ) LOCATION: 106..1620

( x i ) SEQUENCE DESCRIPTION: SEQ ID NO:13:

```
CGCGGCTGGC CCAGCGCCCC GCTGCCCTCC GCCCTGGGCC CGGGTCGGAG TGGGCCGGGC    60

AGGCGGGCCG GGGCTCGGTT GCGACCCGGG GGCTCGGTGG CGAAG ATG GCG TCC       114
                                                  Met Ala Ser
                                                    1
```

| GGC | AGG | CGC | GCC | CCG | CGA | ACC | GGA | CTG | CTG | GAG | CTT | CGT | GCC | GGG | ACG | 162 |
| --- | --- | --- | --- | --- | --- | --- | --- | --- | --- | --- | --- | --- | --- | --- | --- | --- |
| Gly | Arg | Arg | Ala | Pro | Arg | Thr | Gly | Leu | Leu | Glu | Leu | Arg | Ala | Gly | Thr |     |
|     | 5   |     |     |     |     | 10  |     |     |     |     | 15  |     |     |     |     |     |

```
GGC GCG GGG GCA GGC GGA GAG CGC TGG CAG CGG GTG TTG GTC AGT CTG        210
Gly Ala Gly Ala Gly Gly Glu Arg Trp Gln Arg Val Leu Val Ser Leu
 20              25                  30                      35

GCG GAG GAC GCG CTG ACC GTG AGC CCC GCC GAC GGC GAG CCA GGC CCC        258
Ala Glu Asp Ala Leu Thr Val Ser Pro Ala Asp Gly Glu Pro Gly Pro
             40                  45                  50

GAG CCC GGC GCT GTG CGG GAG CCC GAG CCC GCA CAG ATC AAC GGC GCC        306
Glu Pro Gly Ala Val Arg Glu Pro Glu Pro Ala Gln Ile Asn Gly Ala
             55                  60                  65

GCT GAG CCG GGC GCG GCG CCC CCG CAG TTG CCC GAG GCG CTG CTG CTC        354
Ala Glu Pro Gly Ala Ala Pro Pro Gln Leu Pro Glu Ala Leu Leu Leu
             70                  75                  80

CAG CGG CGC CGC GTG ACG GTG CGC AAG GCC GAC GCG GGC GGG CTG GGC        402
Gln Arg Arg Arg Val Thr Val Arg Lys Ala Asp Ala Gly Gly Leu Gly
         85                  90                  95

ATC AGC ATC AAA GGA GGC CGG GAG AAC AAG ATG CCC ATC CTC ATT TCC        450
Ile Ser Ile Lys Gly Gly Arg Glu Asn Lys Met Pro Ile Leu Ile Ser
100              105                 110                     115

AAG ATC TTC AAG GGA CTG GCG GCG GAC CAG ACA GAG GCC CTG TTT GTG        498
Lys Ile Phe Lys Gly Leu Ala Ala Asp Gln Thr Glu Ala Leu Phe Val
                 120                 125                 130

GGG GAT GCC ATC CTG TCG GTG AAT GGG GAA GAC TTG TCC TCT GCC ACC        546
Gly Asp Ala Ile Leu Ser Val Asn Gly Glu Asp Leu Ser Ser Ala Thr
                 135                 140                 145

CAC GAT GAA GCA GTG CAG GCC CTG AAG AAG ACG GGC AAG GAG GTG GTG        594
His Asp Glu Ala Val Gln Ala Leu Lys Lys Thr Gly Lys Glu Val Val
             150                 155                 160

CTG GAG GTC AAG TAC ATG AAG GAG GTC TCA CCT TAT TTC AAG AAT TCT        642
Leu Glu Val Lys Tyr Met Lys Glu Val Ser Pro Tyr Phe Lys Asn Ser
165                 170                 175

GCT GGT GGG ACC TCA GTT GGC TGG GAC TCA CCT CCT GCC TCA CCC CTT        690
Ala Gly Gly Thr Ser Val Gly Trp Asp Ser Pro Pro Ala Ser Pro Leu
180                 185                 190                 195

CAG CGG CAG CCT TCG TCC CCC GGG CCC CAA ACC CGG AAC CTC AGC GAG        738
Gln Arg Gln Pro Ser Ser Pro Gly Pro Gln Thr Arg Asn Leu Ser Glu
                 200                 205                 210

GCC AAA CAT GTG CCC CTG AAG ATG GCC TAT GTG TCA AGG AGG TGC ACC        786
Ala Lys His Val Pro Leu Lys Met Ala Tyr Val Ser Arg Arg Cys Thr
             215                 220                 225

CCC TCG GAC CCG GAG CAC AGG TAC CTA GAG ATC TGT TCA GCA GAT GGC        834
Pro Ser Asp Pro Glu His Arg Tyr Leu Glu Ile Cys Ser Ala Asp Gly
             230                 235                 240

CAA GAC ACC ATC TTT CTG AGA GCC AAG GAT GAG GCT AGT GCG AGG TCG        882
Gln Asp Thr Ile Phe Leu Arg Ala Lys Asp Glu Ala Ser Ala Arg Ser
             245                 250                 255

TGG GCC GGT GCC ATC CAA GCC CAG ATC AAC GCT CTG CTG CCC TGG GTC        930
Trp Ala Gly Ala Ile Gln Ala Gln Ile Asn Ala Leu Leu Pro Trp Val
260                 265                 270                 275

AAG GAC GAG CTC CAG GCA CTG CTG GCA GCT TCC AGT CCA GCT GGG AGC        978
Lys Asp Glu Leu Gln Ala Leu Leu Ala Ala Ser Ser Pro Ala Gly Ser
                 280                 285                 290

CAG GAC ATC AAG CAG ATT GGC TGG CTG ACT GAG CAG CTG CCC AGC GGG       1026
Gln Asp Ile Lys Gln Ile Gly Trp Leu Thr Glu Gln Leu Pro Ser Gly
                 295                 300                 305

GGC ACA GCC CCA ACC TTG GCC TTG CTG ACA GAA AAG GAG CTG CTC CTC       1074
Gly Thr Ala Pro Thr Leu Ala Leu Leu Thr Glu Lys Glu Leu Leu Leu
             310                 315                 320

TAC GGT GGT CTC CCC CAG ACC CGG GAG GCC CTG AGC CGG CCG GCC CGT       1122
Tyr Gly Gly Leu Pro Gln Thr Arg Glu Ala Leu Ser Arg Pro Ala Arg
325                 330                 335
```

```
ACT GCC CCG CTC ATC GCC ACG AGG CTG GTG CAC TCG GGC CCC TCG AAG      1170
Thr Ala Pro Leu Ile Ala Thr Arg Leu Val His Ser Gly Pro Ser Lys
340             345                 350                 355

GGC TCC GTG CCC TAC GAT GCA GAG CTC TCC TTT GCC CTG CGC ACG GGC      1218
Gly Ser Val Pro Tyr Asp Ala Glu Leu Ser Phe Ala Leu Arg Thr Gly
                360                 365                 370

ACA CGC CAC GGG GTG GAC ACG CAC CTG TTC AGC GTG GAG TCA CCG CAG      1266
Thr Arg His Gly Val Asp Thr His Leu Phe Ser Val Glu Ser Pro Gln
            375                 380                 385

GAG CTG GCT GCC TGG ACC CGC CAG CTG GTG GAC GGC TGT CAC CGG GCT      1314
Glu Leu Ala Ala Trp Thr Arg Gln Leu Val Asp Gly Cys His Arg Ala
        390                 395                 400

GCC GAG GGT GTG CAG GAG GTG TCT ACA GCC TGC ACG TGG AAT GGC CGC      1362
Ala Glu Gly Val Gln Glu Val Ser Thr Ala Cys Thr Trp Asn Gly Arg
405                 410                 415

CCC TGC AAC CTC TCT GTG CAC ATT GAC AAG GGC TTC ACG CTG TGG GCG      1410
Pro Cys Asn Leu Ser Val His Ile Asp Lys Gly Phe Thr Leu Trp Ala
420                 425                 430                 435

GCT GAG CCT GGC GCC GCC CGA GCC GTG CTC CTC CGA CAG CCC TTC GAG      1458
Ala Glu Pro Gly Ala Ala Arg Ala Val Leu Leu Arg Gln Pro Phe Glu
                440                 445                 450

AAG CTG CAG ATG TCC TCA GAT GAC GGT GCC AGT CTC CTC TTC CTG GAC      1506
Lys Leu Gln Met Ser Ser Asp Asp Gly Ala Ser Leu Leu Phe Leu Asp
            455                 460                 465

TTC GGT GGT GCT GAA GGC GAG ATC CAG CTG GAC CTG CAC TCG TGT CCC      1554
Phe Gly Gly Ala Glu Gly Glu Ile Gln Leu Asp Leu His Ser Cys Pro
        470                 475                 480

AAA ACC ATG GTC TTC ATC ATC CAC TCC TTC CTC TCG GCC AAA GTC ACC      1602
Lys Thr Met Val Phe Ile Ile His Ser Phe Leu Ser Ala Lys Val Thr
485                 490                 495

CGC CTG GGG CTG CTG GCC TAGAAGTCGC CGGATGCACC AGCCCTGAAG             1650
Arg Leu Gly Leu Leu Ala
500                 505

AGGGGTGTC CACCACGTGT CCTGACCTGG CCCTCCACTG ACCACTCACC CCAGGGCTGC     1710

GGGGAGGGAG AGGGGAGGAG TGAGGTGCTC AGAGAGCCAG CCCTTGAGGG AGCCTGGACT    1770

GGTCTGGGGA CGGACTCACT GGACCCTGCC CGTGCTGGGG TGGCCTGCCC GCTGCCCCCT    1830

CCACCAGTGC CTTTTGCAGA GAGAGATTTT ACGTACATAG AAGCCATTCC GAGCCTGGGA    1890

CCTGCCCCCG TGGGGATCCT GACTCCGCAC AGCAGCTGAA CTGCCAGGCC TCCAGGAAGT    1950

CCCCGAGTCG CTCCCAGAGG CCCCTTCCGA AGTCGGAGTC CCCCGGGGTC AGTGGCAGGA    2010

GAAAGAACGG AAGCCTTTTT GCTCATTGTC CCCTCCGTCC CACCACCTTG GCCCTCTGG     2070

TTTCTCTCTT CATCTCTCTC TCTCTCTCTC TCTCTCTCGT TCTTGGATAA ATAAACACCT    2130

GCAAGCACAT AAGCAGCCTG TTCCGGTGTC TGTGGTTTGT GCGCGACCTC TGGGCCCTGT    2190

GCTGGCTCCC GCGGTCCAAG ACGCCCAGGC CAAGGACTGG AGCCCCTCCC CCGGGCAAGA    2250

GCAGACCTTC AACCGGGGCC CCAAAGGCGT GACACTGGCT GCCTGGAGCA GTGTTTGTTG    2310

TCTCGCTGGC TCTGGGCCCC GGGGGTTATT ACCAGCCAGT AGAAGTGTGG TGTGACTCGT    2370

AGATTGTTCT GAGGCGTGA                                                 2389
```

( 2 ) INFORMATION FOR SEQ ID NO:14:

( i ) SEQUENCE CHARACTERISTICS:
        ( A ) LENGTH: 505 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Ala Ser Gly Arg Arg Ala Pro Arg Thr Gly Leu Leu Glu Leu Arg
 1               5                  10                  15

Ala Gly Thr Gly Ala Gly Ala Gly Gly Glu Arg Trp Gln Arg Val Leu
            20                  25                  30

Val Ser Leu Ala Glu Asp Ala Leu Thr Val Ser Pro Ala Asp Gly Glu
        35                  40                  45

Pro Gly Pro Glu Pro Gly Ala Val Arg Glu Pro Glu Pro Ala Gln Ile
    50                  55                  60

Asn Gly Ala Ala Glu Pro Gly Ala Ala Pro Pro Gln Leu Pro Glu Ala
 65                  70                  75                  80

Leu Leu Leu Gln Arg Arg Arg Val Thr Val Arg Lys Ala Asp Ala Gly
            85                  90                  95

Gly Leu Gly Ile Ser Ile Lys Gly Gly Arg Glu Asn Lys Met Pro Ile
            100                 105                 110

Leu Ile Ser Lys Ile Phe Lys Gly Leu Ala Ala Asp Gln Thr Glu Ala
        115                 120                 125

Leu Phe Val Gly Asp Ala Ile Leu Ser Val Asn Gly Glu Asp Leu Ser
    130                 135                 140

Ser Ala Thr His Asp Glu Ala Val Gln Ala Leu Lys Lys Thr Gly Lys
145                 150                 155                 160

Glu Val Val Leu Glu Val Lys Tyr Met Lys Glu Val Ser Pro Tyr Phe
                165                 170                 175

Lys Asn Ser Ala Gly Gly Thr Ser Val Gly Trp Asp Ser Pro Pro Ala
            180                 185                 190

Ser Pro Leu Gln Arg Gln Pro Ser Ser Pro Gly Pro Gln Thr Arg Asn
    195                 200                 205

Leu Ser Glu Ala Lys His Val Pro Leu Lys Met Ala Tyr Val Ser Arg
210                 215                 220

Arg Cys Thr Pro Ser Asp Pro Glu His Arg Tyr Leu Glu Ile Cys Ser
225                 230                 235                 240

Ala Asp Gly Gln Asp Thr Ile Phe Leu Arg Ala Lys Asp Glu Ala Ser
            245                 250                 255

Ala Arg Ser Trp Ala Gly Ala Ile Gln Ala Gln Ile Asn Ala Leu Leu
            260                 265                 270

Pro Trp Val Lys Asp Glu Leu Gln Ala Leu Leu Ala Ala Ser Ser Pro
        275                 280                 285

Ala Gly Ser Gln Asp Ile Lys Gln Ile Gly Trp Leu Thr Glu Gln Leu
    290                 295                 300

Pro Ser Gly Gly Thr Ala Pro Thr Leu Ala Leu Leu Thr Glu Lys Glu
305                 310                 315                 320

Leu Leu Leu Tyr Gly Gly Leu Pro Gln Thr Arg Glu Ala Leu Ser Arg
                325                 330                 335

Pro Ala Arg Thr Ala Pro Leu Ile Ala Thr Arg Leu Val His Ser Gly
            340                 345                 350

Pro Ser Lys Gly Ser Val Pro Tyr Asp Ala Glu Leu Ser Phe Ala Leu
        355                 360                 365

Arg Thr Gly Thr Arg His Gly Val Asp Thr His Leu Phe Ser Val Glu
    370                 375                 380

Ser Pro Gln Glu Leu Ala Ala Trp Thr Arg Gln Leu Val Asp Gly Cys
385                 390                 395                 400

His Arg Ala Ala Glu Gly Val Gln Glu Val Ser Thr Ala Cys Thr Trp
                405                 410                 415
```

| | | | | | | | | | | | | | | |
|---|---|---|---|---|---|---|---|---|---|---|---|---|---|---|
| Asn | Gly | Arg | Pro 420 | Cys | Asn | Leu | Ser | Val 425 | His | Ile | Asp | Lys | Gly 430 | Phe | Thr |
| Leu | Trp | Ala 435 | Ala | Glu | Pro | Gly | Ala 440 | Ala | Arg | Ala | Val | Leu 445 | Leu | Arg | Gln |
| Pro | Phe 450 | Glu | Lys | Leu | Gln | Met 455 | Ser | Ser | Asp | Asp | Gly 460 | Ala | Ser | Leu | Leu |
| Phe 465 | Leu | Asp | Phe | Gly | Gly 470 | Ala | Glu | Gly | Glu | Ile 475 | Gln | Leu | Asp | Leu | His 480 |
| Ser | Cys | Pro | Lys | Thr 485 | Met | Val | Phe | Ile | Ile 490 | His | Ser | Phe | Leu | Ser 495 | Ala |
| Lys | Val | Thr | Arg 500 | Leu | Gly | Leu | Leu | Ala 505 | | | | | | | |

( 2 ) INFORMATION FOR SEQ ID NO:15:

( i ) SEQUENCE CHARACTERISTICS:
        ( A ) LENGTH: 15
        ( B ) TYPE: amino acid
        ( D ) TOPOLOGY: linear ( i i ) MOLECULE TYPE: Peptide ( x i ) SEQUENCE DESCRIPTION: SEQ ID NO:15:

Pro Lys Asn Met Thr Pro Tyr Arg Ser Pro Pro Pro Tyr Val Pro